US011486829B2

(12) United States Patent
Nolan et al.

(10) Patent No.: US 11,486,829 B2
(45) Date of Patent: Nov. 1, 2022

(54) OPTICAL ANALYSES OF PARTICLES AND VESICLES

(71) Applicant: SCINTILLON INSTITUTE FOR BIOMEDICAL AND BIOENERGY RESEARCH, San Diego, CA (US)

(72) Inventors: John P. Nolan, La Jolla, CA (US); Erika Duggan, San Diego, CA (US)

(73) Assignee: Scintillon Institute for Biomedical and Bioenergy Research, San Diego, CA (US)

(*) Notice: Subject to any disclaimer, the term of this patent is extended or adjusted under 35 U.S.C. 154(b) by 317 days.

(21) Appl. No.: 16/534,854

(22) Filed: Aug. 7, 2019

(65) Prior Publication Data

US 2020/0173923 A1 Jun. 4, 2020

Related U.S. Application Data

(62) Division of application No. 15/233,723, filed on Aug. 10, 2016, now Pat. No. 10,429,302.

(60) Provisional application No. 62/203,594, filed on Aug. 11, 2015.

(51) Int. Cl.

| G01N 21/64 | (2006.01) |
|---|---|
| G01N 15/06 | (2006.01) |
| G01N 15/14 | (2006.01) |
| G01N 33/53 | (2006.01) |
| G01N 33/542 | (2006.01) |
| G01N 33/569 | (2006.01) |
| G01N 33/58 | (2006.01) |
| G01N 15/00 | (2006.01) |
| G01N 15/10 | (2006.01) |

(52) U.S. Cl.
CPC ......... *G01N 21/6428* (2013.01); *G01N 15/06* (2013.01); *G01N 15/1429* (2013.01); *G01N 15/1459* (2013.01); *G01N 33/5308* (2013.01); *G01N 33/542* (2013.01); *G01N 33/56983* (2013.01); *G01N 33/582* (2013.01); *G01N 2015/0065* (2013.01); *G01N 2015/0687* (2013.01); *G01N 2015/0693* (2013.01); *G01N 2015/1087* (2013.01); *G01N 2015/1486* (2013.01); *G01N 2015/1488* (2013.01); *G01N 2015/1493* (2013.01); *G01N 2021/6439* (2013.01)

(58) Field of Classification Search
CPC ............... G01N 21/6428; G01N 15/06; G01N 15/14219; G01N 15/1459; G01N 33/5308; G01N 33/542; G01N 33/56983; G01N 33/582; G01N 2015/0065; G01N 2015/0687; G01N 2015/0693; G01N 2015/1087; G01N 2015/1486; G01N 2015/1488; G01N 2015/1493; G01N 2021/6439

See application file for complete search history.

(56) References Cited

U.S. PATENT DOCUMENTS

| 4,078,052 A | 3/1978 | Papahadjopoulos |
| 4,224,179 A | 9/1980 | Schneider |
| 4,235,871 A | 11/1980 | Papahadjopoulos et al. |
| 4,308,166 A | 12/1981 | Marchetti et al. |
| 4,310,506 A | 1/1982 | Baldeschwieler et al. |
| 4,394,372 A | 7/1983 | Taylor |
| 4,485,054 A | 11/1984 | Mezei et al. |
| 4,508,703 A | 4/1985 | Redziniak et al. |
| 4,522,803 A | 6/1985 | Lenk et al. |
| 5,631,018 A | 5/1997 | Zalipsky et al. |
| 10,429,302 B2 | 10/2019 | Nolan et al. |
| 2017/0045451 A1 | 2/2017 | Nolan et al. |

FOREIGN PATENT DOCUMENTS

| WO | WO 2016/154283 A1 | 9/2016 |
| WO | WO 2017/027622 A1 | 2/2017 |

OTHER PUBLICATIONS

Qhobosheane, Monde et al. "Biochemically functionalized silica nanoparticles." The Analyst (2001) 126 1274-1278. (Year: 2001).*
"Invitation to Pay Additional Fees dated Nov. 24, 2016 in International Patent Application No. PCT/US2016/046401, filed on Aug. 10, 2016", 7 pages.
"Office Action dated May 9, 2019 in U.S. Appl. No. 15/233,723, filed Aug. 10, 2016 and published as US 2017-0045451 on Feb. 16, 2017", 8 pages.
"Office Action dated Oct. 1, 2018 in U.S. Appl. No. 15/233,723, filed Aug. 10, 2016 and published as US 2017-0045451 on Feb. 16, 2017", 7 pages.
Akers, et al., "Methods for Quantifying Extracellular Vesicles (EVs) in Clinical Cerebrospinal Fluids (CSF)", ISEV, 2015, abs. P-XI-2.
Arraud, et al., "Fluorescence Triggering: A General Strategy for Enumerating and Phenotyping Extracellular Vesicles by Flow Cytometry", Cytometry Part A., Apr. 9, 2015, 89(2):184-195.
Belas, et al., "Bacterial Bioluminescence: Isolation and Expression of the Luciferase Genes from Vibrio Harveyi", Science, Nov. 19, 1982, 218(4574):791-793.
Chandler, et al., "A New Microparticle Size Calibration Standard for Use in Measuring Smaller Microparticles Using a New Flow Cytometer", Journal of Thrombosis and Haemostasis, Jun. 2011, 9(6):1216-1224.
Chandler, et al., "Measurement of Microvesicle Levels in Human Blood Using Flow Cytometry", Cytometry Part B (Clinical Cytometry), Feb. 3, 2016, 90B:326-336.
Chase, et al., "Resolution of Dimly Fluorescent Particles: A Practical Measure of Fluorescence Sensitivity", Cytometry, 1998, 33:267-279.

(Continued)

*Primary Examiner* — Christopher Adam Hixson
(74) *Attorney, Agent, or Firm* — Grant IP, Inc.

(57) ABSTRACT

This technology relates in part to optical methods for analyzing particles, including nanoparticles, thereby determining their presence, identity, origin, size and/or number in a sample of interest.

26 Claims, 17 Drawing Sheets

(56) References Cited

OTHER PUBLICATIONS

Coumans, et al., "Reproducible Extracellular Vesicle Size and Concentration Determination with Tunable Resistive Pulse Sensing", Journal of Extracellular Vesicles, Dec. 10, 2014, 3:25922.
De Rond, et al., "Comparison of Generic Fluorescent Markers for Detection of Extracellular Vesicles by Flow Cytometry", Clinical Chemistry, 2018, 64(4):680-689.
De Wet, et al., "Firefly Luciferase Gene: Structure and Expression in Mammalian Cells", Molecular and Cellular Biology, Feb. 1987, 7(2):725-737.
Dragovic, et al., "Sizing and Phenotyping of Cellular Vesicles Using Nanoparticle Tracking Analysis", Nanomedicine: Nanotechnology, Biology and Medicine, Dec. 2011, 7(6):780-788.
Escher, et al., "Bacterial Luciferase Alpha Beta Fusion Protein is Fully Active as a Monomer and Highly Sensitive in Vivo to Elevated Temperature", PNAS, Sep. 1989, 86(17):6528-6532.
Foran, et al., "Nucleotide Sequence of the LuxA and LuxB Genes of the Bioluminescent Marine Bacterium Vibrio Fischeri", Nucleic Acids Research, Jan. 25, 1988, 16(2):777.
Gould, et al., "As We Wait: Coping with an Imperfect Nomenclature for Extracellular Vesicles", Journal of Extracellular Vesicles, Feb. 2013, 2:20389.
Greenspan, et al., "Nile Red: A Selective Fluorescent Stain for Intracellular Lipid Droplets", Journal of Cell Biology, Mar. 1, 1985, 100:965-973.
Hoen, et al., "Quantitative and Qualitative Flow Cytometric Analysis of Nanosized Cell-Derived Membrane Vesicles", Nanomedicine: Nanotechnology, Biology and Medicine, Jul. 2011, 8(5):712-720.
Hoffman, et al., "Characterization of Flow Cytometer Instrument Sensitivity", Current Protocols in Cytometry, Apr. 2007, 40(1):1. 20.1-1.20.18.
Kojima, et al., "Exosomes in Postshock Mesenteric Lymph are Key Mediators of Acute Lung Injury Triggering the Macrophage Activation via Toll-Like Receptor 4", FASEB Journal, 2018, 32:97-110.
Kormelink, et al., "Prerequisites for the Analysis and Sorting of Extracellular Vesicle Subpopulations by High-Resolution Flow Cytometry", Cytometry Part A, Feb. 2016, 89(2):135-147.
Kunding, et al., "A Fluorescence-Based Technique to Construct Size Distributions from Single-Object Measurements: Application to the Extrusion of Lipid Vesicles", Biophysical Journal, Aug. 2018, 95(3):1176-1188.
Lacroix, et al., "Standardization of Platelet-Derived Microparticle Enumeration By Flow Cytometry with Calibrated Beads: Results of the International Society on Thrombosis and Haemostasis SSC Collaborative Workshop", Journal of Thrombosis and Haemostasis, Nov. 2010, 8(11):2571-2574.
Lee, et al., "Lipid-Nanostructure Hybrids and Their Applications in Nanobiotechnology", NPG Asia Materials, May 17, 2013, 5: e48.
Lorenz, et al., "Isolation and Expression of a cDNA Encoding Renilia reniformis Luciferase", PNAS, May 1991, 88:4438-4442.
Morales-Kastresana, et al., "Labeling Extracellular Vesicles for Nanoscale Flow Cytometry", Scientific Reports, 2017, 7:1878.
Nolan, et al., "A Trigger Channel Threshold Artifact in Nanoparticle Analysis", Cytometry Part A, Mar. 2013, 83(3):301-305.
Nolan, et al., "Analysis of Individual Extracellular Vesicles by Flow Cytometry", Flow Cytometry Protocols, 2018, 79-92.
Nolan, et al., "Assessment of Cardiovascular Status in Rats Using Nanovesicle Flow Cytometry", ISEV, 2015, abs 0-6A-3.
Nolan, et al., "Development of Brighter Surface Enhanced Raman Scattering Tags for Multiplexed Cytometry", ISAC Program and Abstracts, 2013, 129: abs 111.
Nolan, et al., "Nanoparticle Flow Cytometry of Individual Extracellular Vesicles?", ISAC Program and Abstracts, 2014, 119: abs 129.
Nolan, et al., "Quantitative Real Time Single Cell Spectroscopy in Flow", ISAC Proqram and Abstracts, 2013, 96: abs 22.
Nolan, et al., "Single Cell Analysis Using Surface Enhanced Raman Scattering (SERS) Tags", Methods, Jul. 2012, 57(3):272-279.

Nolan, et al., "Spectral Flow Cytometry of Fluorescent Proteins ISAC Program and Abstracts", 2014, 91: abs 52.
Nolan, et al., "Vesicle Flow Cytometry of Extracellular Vesicles in Cerebral Spinal Fluid", ISEV, 2015, abs. P-XIII-9.
"International Preliminary Report on Patentability dated Feb. 22, 2018 in International Patent Application No. PCT/US2016/046401, filed on Aug. 10, 2016", 13 pages.
"International Search Report and Written Opinion dated Jan. 16, 2017 in International Patent Application No. PCT/US2016/046401, filed on Aug. 10, 2016", 17 pages.
Prasher, et al., "Primary Structure of the Aequorea victoria Green-Fluorescent Protein", Gene, Feb. 15, 1992, 111(2):229-233.
Prasher, et al., "Sequence Comparisons of Complementary DNAs Encoding Aequorin Isotypes", Biochemistry, Mar. 1, 1987, 26(5):1326-1332.
Saugstad, et al., "Analysis of Extracellular RNA in Cerebrospinal Fluid", Journal of Extracellular Vesicles, 2017, 6:1317577.
Schwartz, et al., "Formalization of the MESF unit of fluorescence intensity", Cytometry Part B: Clinical Cytometry, Jan. 2004, 57(1):1-6.
Schwartz, et al., "Standardizing Flow Cytometry: A Classification System of Fluorescence Standards Used for Flow Cytometry", Cytometry, Oct. 1998, 33(2):106-114.
Schwartz, et al., "Standardizing Flow Cytometry: Construction of a Standardized Fluorescence Calibration Plot Using Matching Spectral Calibrators", Cytometry, Mar. 15, 1996, 26(1):22-31.
Stoner, et al., "Flow Cytometric Analysis of Single Lipid Membrane Vesicles", ISAC Program and Abstracts, 2014, 120: abs 85.
Van Der Pol, et al., "Optical and Non-Optical Methods for Detection and Characterization of Microparticles and Exosomes", Journal of Thrombosis and Haemostasis, Dec. 2010, 8(12):2596-2607.
Van Der Pol, E, et al., "Particle Size Distribution of Exosomes and Microvesicles Determined by Transmission Electron Microscopy, Flow Cytometry, Nanoparticle Tracking Analysis, and Resistive Pulse Sensing", Journal of Thrombosis and Haemostasis, Jul. 2014, 12(7):1182-1192.
Van Der Vlist, et al., "Fluorescent Labeling of Nano-Sized Vesicles Released by Cells and Subsequent Quantitative and Qualitative Analysis by High-Resolution Flow Cytometry", Nature Protocols, Jun. 2012, 7(7):1311-1326.
Wang, et al., "Quantitating Fluorescence Intensity from Fluorophores: Practical Use of MESF Values", Journal of Research of NIST, Jul.-Aug. 2002, 107(4):339-353.
Wood, et al., "Evaluating Fluorescence Sensitivity on Flow Cytometers: An Overview", Cytometry, Oct. 1998, 33(2):256-259.
Wood, James C., "Fundamental Flow Cytometer Properties Governing Sensitivity and Resolution", Cytometry, Oct. 1, 1998, 33(2):260-266.
Zhang, et al., "High-Throughput Multiparameter Analysis of Individual Mitochondria", Analytical Chemistry, 2012, 84(15):6421-6428.
Zhu, et al., "Light-Scattering Detection below the Level of Single Fluorescent Molecules for High-Resolution Characterization of Functional Nanoparticles", ACS Nano, Oct. 2014, 8:10998-11006.
Chemburu et al., "Biomimetic Silica Microspheres in Biosensing", Molecules, 2010, 15:1932-1957.
Lauer et al., "Analysis of Cholera Toxin-Ganglioside Interactions by Flow Cytometry", Biochemistry, 2002, 41:1742-1751.
Lauer et al., "Development and Characterization of Ni-NTA-Bearing Microspheres", Cytometry, 2002, 48:136-145.
Song et al., "Detection of Multivalent Interactions through Two-Tiered Energy Transfer", Analytical Biochemistry, 2001, 291:133-141.
Song et al., "Optical Biosensor Based on Fluorescence Resonance Energy Transfer: Ultrasensitive and Specific Detection of Protein Toxins", Journal of the American Chemical Society, 1998, 120:11514-11515.
Song et al., "Optical Signal Transduction Triggered by Protein-Ligand Binding: Detection of Toxins Using Multivalent Binding", Journal of the American Chemical Society, 1998, 120:4873-4874.

* cited by examiner

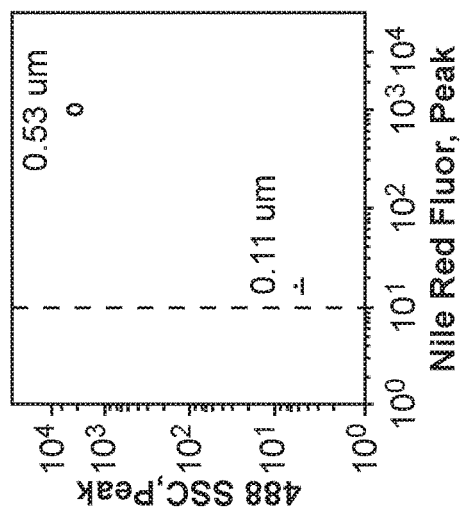
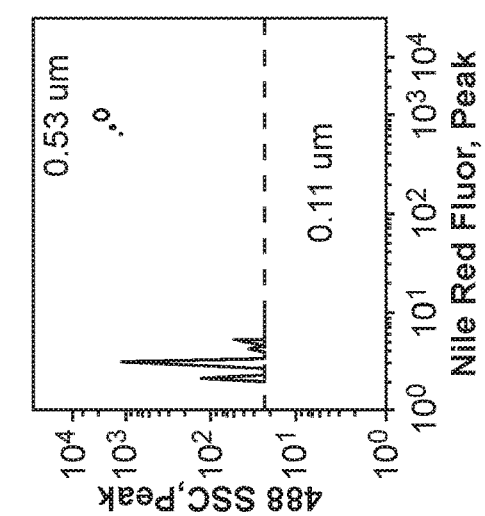
FIG. 1A    FIG. 1B    FIG. 1C
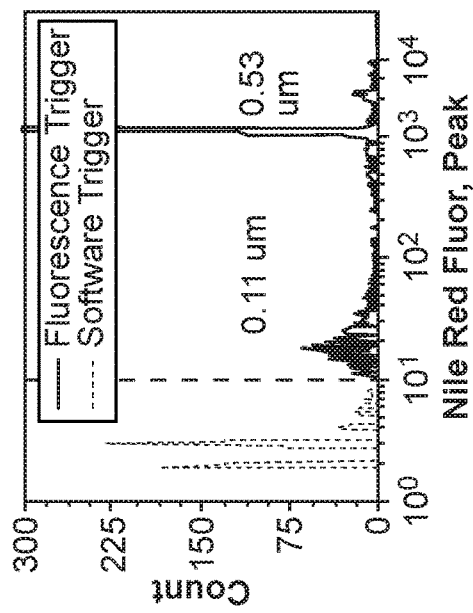
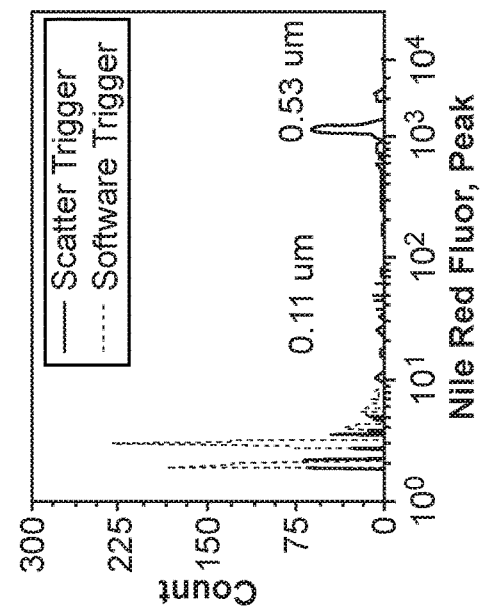
FIG. 1D    FIG. 1E    FIG. 1F

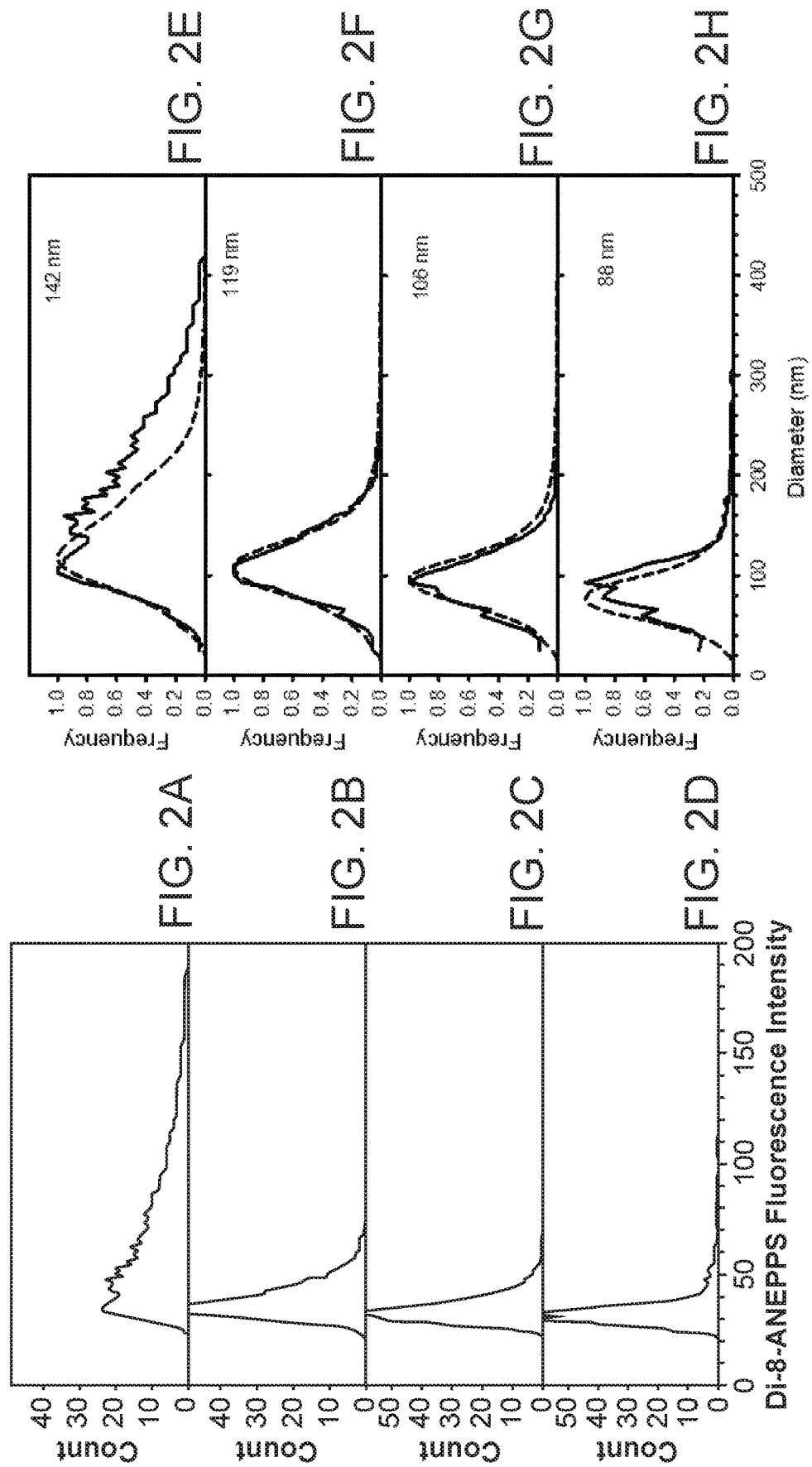

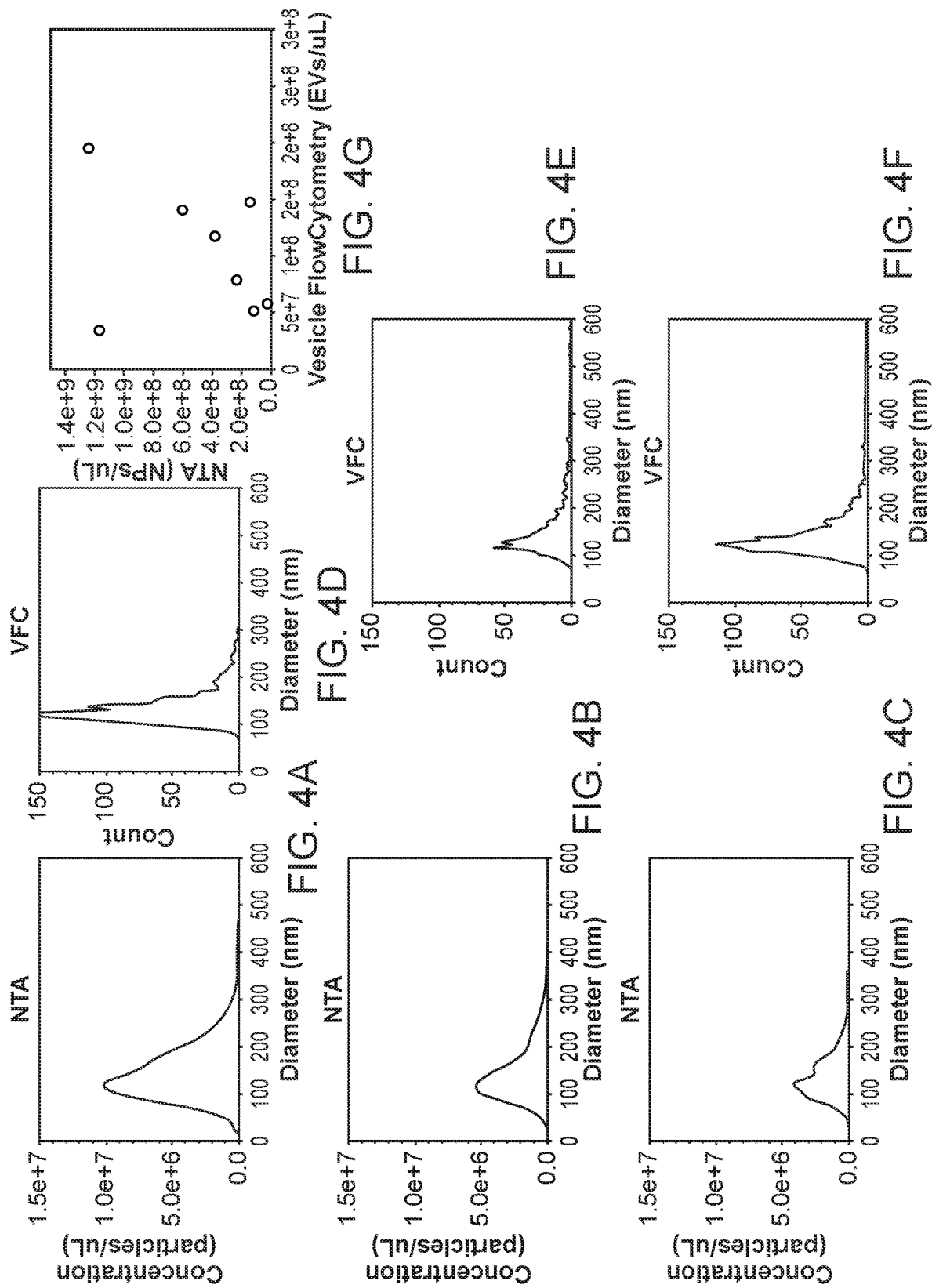

Fig. 11C
PRP supernatant
+CD41-PE
+CD235-APC
+AnnV-PECy7
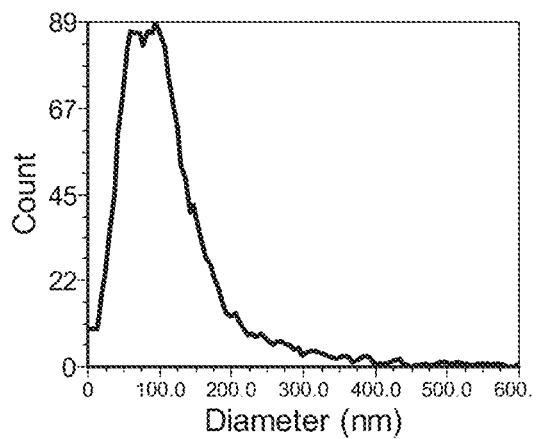
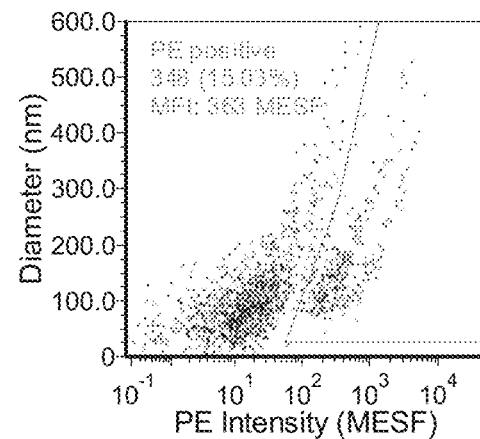
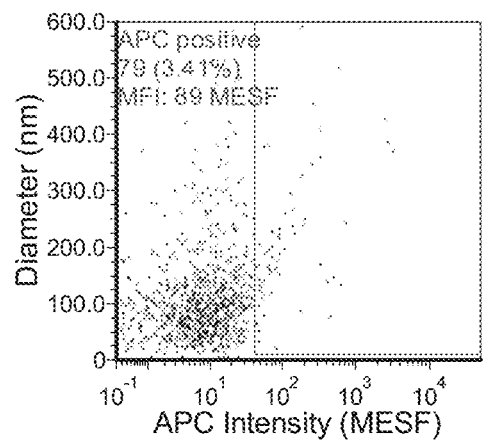
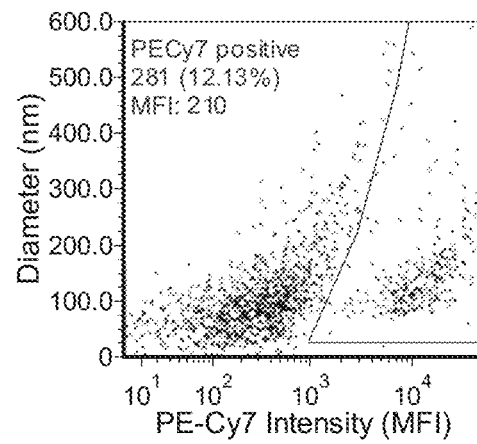

OPTICAL ANALYSES OF PARTICLES AND VESICLES

RELATED PATENT APPLICATIONS

This patent application is a divisional of U.S. patent application Ser. No. 15/233,723 filed on Aug. 10, 2016, naming John P. Nolan and Erika Duggan as inventors, entitled OPTICAL ANALYSES OF PARTICLES AND VESICLES, which claims the benefit of U.S. Provisional Application No. 62/203,594, filed on Aug. 11, 2015, entitled OPTICAL ANALYSES OF PARTICLES AND VESICLES, naming John P. Nolan and Erika Duggan as inventors. The entire content of the foregoing patent application is incorporated herein by reference, including, without limitation, all text, tables and drawings.

The subject matter claimed in this application was made with government support under Grant Number EB003824 awarded by the National Institutes of Health. The United States Government has certain rights in this subject matter.

FIELD

The technology relates in part to optical methods for analyzing particles and vesicles, including membrane vesicles such as liposomes and extracellular vesicles.

BACKGROUND

Optical methods for detecting particles and/or determining their identity, number, size or origin have long been in use. However, the staining of particles using optically detectable labels generally must be accompanied by one or more washing and/or centrifugation procedures to remove background interference from unbound label. Physical separation procedures, such as washing or centrifugation/ultracentrifugation, can lead to inefficiencies as well as inaccuracies in the analyses, especially when analyzing small volumes of sample, due to partial loss of particles during the separation.

In addition, the analyses of small particles, in the range of nanometers in diameter or less (e.g., about 100-200 nm or less), pose hurdles. For example, light scatter-based flow cytometry analyses of extracellular vesicles (EVs), exemplary of which are biological membrane vesicles that are released from cell surfaces (ectosomes), internal stores (exosomes) or as a result of apoptosis or cell death, often provide incorrect estimates of their size and concentration when the vesicles are nanovesicles, due to dim light scatter. Further, detection of the EVs often is triggered by coincidence, i.e., simultaneous detection of the presence of more than one EV in the flow cytometer measurement volume, leading to incorrect concentration, size and fluorescence estimates.

Some optical methods, such as nanoparticle tracking analysis (NTA), also are limited in their ability to measure nanoparticles, due to the particles scattering less light than the limits of detection. In addition, unlike flow cytometry, where the entire sample containing the particles passes through the measurement volume, particles can diffuse in and out of the probe volume during NTA measurements, resulting in over-counting of smaller particles and under-counting of larger particles. Improved optical methods are needed for the detection of particles, including nanoparticles, among which are EVs, which often are 500 nm or less in diameter.

SUMMARY

Provided in certain aspects is a method of analyzing particles in a sample that includes: (a) contacting a sample comprising the particles with one or more optically detectable labels, thereby forming a staining solution, where: (i) the one or more optically detectable labels include a surface area probe or volume probe, where the surface area probe interacts with the particles stoichiometrically with respect to particle surface area or the volume probe interacts with the particles stoichiometrically with respect to particle volume, thereby forming particles that include particle-associated surface area probe or volume probe, where the optical signal from the particle-associated surface area probe or volume probe is proportional to the surface area or volume of the particle, respectively, and/or (ii) the one or more optically detectable labels include a molecular marker-specific probe, where the molecular marker-specific probe interacts with a molecular marker of the particle stoichiometrically with respect to the number of molecules of the molecular marker that are associated with the particle, thereby forming particles that include particle-associated molecular marker-specific probe, where the optical signal from the particle-associated molecular marker-specific probe is proportional to the number of molecules of molecular marker associated with the particle; and (b) without physical separation or isolation of the particles, detecting the optical signal of the one or more particle-associated optically detectable labels generated in (i) and/or (ii), thereby analyzing the particles in the sample.

Also provided in certain aspects is a method of detecting, identifying, quantifying and/or determining the size of at least a first particle species in a sample that includes at two distinct particle species by: (a) contacting a sample containing at least two distinct particle species, where the distinct particle species differ from one another by size and/or by least one molecular marker associated with each particle species, with one or more optically detectable labels comprising a surface area probe or volume probe, where the surface area probe or volume probe interacts with at least a first particle species stoichiometrically with respect to particle surface area or volume, respectively, thereby forming particles that include particle-associated surface area probe or volume probe, where the optical signal from the particle-associated surface area probe or volume probe is proportional to the surface area or volume, respectively, of the first particle species; and/or (b) contacting the sample with one or more optically detectable labels that include a molecular marker-specific probe, where the molecular marker-specific probe interacts with a molecular marker of at least the first particle species stoichiometrically with respect to the number of molecules of the molecular marker that are associated with the particle, thereby forming particles that include particle-associated molecular marker-specific probe, where the optical signal from the particle-associated molecular marker-specific probe is proportional to the number of molecules of the molecular marker that are associated with the first particle species; (c) detecting an optical signal from the particle-associated surface area probe or volume probe and/or detecting an optical signal from the particle-associated molecular marker-specific probe, thereby obtaining an optical signal intensity from the particle-associated surface area probe or volume probe and/or the particle-associated molecular marker-specific probe; (d) based on the optical intensity of the particle-associated surface area probe or volume probe obtained in (c), determining the surface area or volume of at least the first particle species, thereby detecting and/or determining the size of at least the first particle species in the sample; and/or (e) based on the optical intensity of the particle-associated molecular marker-specific probe obtained in (c), determining the type and/or number of molecular markers associated with at least the first particle species, thereby detecting, identifying and/or quantifying at least the first particle species in the sample. In certain aspects of the method, the particle species are nanoparticle species.

The terms "associated," "associated with" or "interact," as used herein interchangeably with "bound" or "containing," e.g., "lipid-containing particle," can refer to a variety of different types of contact between, for example, a particle and its components (lipids, proteins, nucleic acids, carbohydrates, glycoproteins, glycolipids, phospholipids, phosphosphingolipids, etc.) or between a particle and an optically detectable label that can include, but is not limited to, covalent bonds or non-covalent interactions, non-limiting examples of which include van der Waals interactions, hydrogen bonding, ionic interactions, electrostatic interactions and/or hydrophilic or hydrophobic interactions. In embodiments, the molecule that is the probe is also an optically detectable label, e.g., di-8-ANEPPS.

With respect to the interaction of membrane vesicles, liposomes, extracellular vesicles and other lipid bilayer or lipid membrane containing particles, the terms "associated," "associated with" or "interact," as used herein, also can refer to intercalation of the optically detectable label into the membrane, or binding of the optically detectable label to a molecular marker within or at the surface of the membrane vesicles, liposomes, extracellular vesicles and other lipid bilayer or lipid membrane containing particles. The term "free" or "unbound," as used herein, refers to molecules, including optically detectable labels, which are not in contact with the particle. "Free" or "unbound" optically detectable label, e.g., in the staining solution, generally is detected as a background signal or no signal, relative to the higher signal intensity of the optically detectable label when it is associated with a particle (i.e., a particle-associated surface area probe or volume probe, or a particle-associated molecular marker-specific probe).

Any particle in the size range of nm to microns or larger can be analyzed according to the methods provided herein. In certain aspects, the particle is a nanoparticle of less than 1 micron in diameter. In aspects of the methods provided herein, the nanoparticles in the sample include at least one particle with a size of about 500 nm or less in diameter, between about 10 nm to about 200 nm in diameter, between about 50 nm to about 200 nm in diameter, between about 50 nm to about 150 nm in diameter, between about 10 nm to about 500 nm in diameter, between about 50 nm to about 200 nm in diameter, or between about 50 nm to about 150 nm in diameter.

In certain aspects, the concentration of the particles in the sample is adjusted so the particle is optimally stained with, or associated with, or bound to, the optically detectable label. In some aspects, the particle concentration can be adjusted to between about $1\times10^3$ particles/µL to about $1\times10^{15}$ particles/µL; between about $1\times10^4$ particles/µL to about $1\times10^{14}$ particles/µL; between about $1\times10^5$ particles/µL to about $1\times10^{13}$ particles/µL; between about $1\times10^4$ particles/µL to about $1\times10^{12}$ particles/µL; between about $1\times10^6$ particles/µL to about $1\times10^{12}$ particles/µL; between about $1\times10^6$ particles/µL to about $1\times10^{11}$ particles/µL; between about $1\times10^6$ particles/µL to about $1\times10^{10}$ particles/µL; between about $1\times10^7$ particles/µL to about $1\times10^{10}$ particles/µL, between about $1\times10^8$ particles/µL to about $1\times10^{10}$ particles/µL; or about $1\times10^9$ particles/µL.

In certain aspects, the concentration of the particles in the sample is adjusted using a suitable buffer, such as an isotonic buffer, whereby the resulting staining solution contains a buffer. In aspects, the staining solution includes a surfactant, or a mixture of surfactants. Without being bound by theory, the surfactant could, in some embodiments, facilitate staining of the particles in the staining solution, such as the lipid bilayers of membrane vesicles, liposomes or extracellular vesicles. In some aspects, the surfactant can be added to the staining solution in an amount of between about 0.001% to about 0.5%; between about 0.002% to about 0.4%; between about 0.003% to about 0.3%; between about 0.004% to about 0.2%; between about 0.001% to about 0.1%; between about 0.005% to about 0.05%; between about 0.005% to about 0.04%; between about 0.005% to about 0.02%; or about 0.01%. In aspects of the methods provided herein, the surfactant can be a nonionic poloxamer, such as the Synperonics, Pluronics and Kolliphor classes of poloxamers. In some aspects, the surfactant can be a Pluronic poloxamer. In aspects, the Pluronic poloxamer can be Pluronic-127.

In aspects of the methods provided herein, analyzing the particles in the sample can include detecting the particles in the sample. In general, "analyzing the particles," as used herein, refers to the detection and analysis of individual particles in the sample, such as by flow cytometry. As used herein analyzing the particles "in bulk" means that the particles are analyzed as a whole, without resolution of the individual particles from one another, such as, for example, measuring the absorbance of a suspension of particles in a cuvette using a fluorimeter. A bulk analysis can be distinguished, for example, from the detection and analysis of individual particles, such as by flow cytometry. In certain embodiments, a bulk analysis also can include the detection and analysis of individual particles without distinguishing the individual particles from one another, such as identifying EVs in a sample without distinguishing them according to the cells from which they are derived and/or signature markers associated with different EVs. In certain aspects, analyzing the particles in the sample can include determining the surface area or volume of the particle based on the detected optical signal of the particle-associated surface area probe or volume probe, respectively. In some aspects, the size of the particle can be determined based on the surface area or volume. In aspects, determining the size of the particle includes determining the diameter of the particle.

In some aspects of the methods provided herein, analyzing the particles in the sample can include determining the type and/or number of molecular markers associated with the particle based on the detected optical signal of the molecular marker-associated probe. In aspects, the particle can be identified and/or quantified based on the type and/or number of molecular markers associated with the particle.

In certain aspects of the methods provided herein, the surface area probe or volume probe is a fluorescent label. In some aspects, the molecular marker-specific probe is a fluorescent label. Any fluorescent label can be used in the methods provided herein including, but not limited to, a fluorophore, a tandem conjugate between more than one fluorophore, a fluorescent polymer, a fluorescent protein, or a fluorophore conjugated to a molecule that interacts with one or more particles of the sample. In some aspects, the molecule that interacts with one or more particles of the sample includes, but is not limited to, a protein, an antibody, a lectin, a peptide, a nucleic acid, a carbohydrate or a glycan. The molecule can interact with the particle in a manner that is proportional to the surface area or volume of the particle, or can bind or otherwise associate specifically with one or more molecular markers on the particle.

In certain aspects of the methods provided herein, the molecule that interacts with one or more particles of the sample is an antibody, or a molecular marker-binding/associating fragment thereof. Antibodies bind to specific antigens and contain two identical heavy chains and two identical light chains covalently linked by disulfide bonds. Both the heavy and light chains contain variable regions, which bind the antigen, and constant (C) regions. In each chain, one domain (V) has a variable amino acid sequence depending on the antibody specificity of the molecule. The other domain (C) has a rather constant sequence common among molecules of the same class. The domains are numbered in sequence from the amino-terminal end. For example, the IgG light chain includes two immunoglobulin domains linked from N- to C-terminus in the order $V_L$-$C_L$, referring to the light chain variable domain and the light chain constant domain, respectively. The IgG heavy chain includes four immunoglobulin domains linked from the N- to C-terminus in the order $V_H$-$C_H1$-$C_H2$-$C_H3$, referring to the variable heavy domain, contain heavy domain 1, constant heavy domain 2, and constant heavy domain 3. The resulting antibody molecule is a four chain molecule where each heavy chain is linked to a light chain by a disulfide bond, and the two heavy chains are linked to each other by disulfide bonds. Linkage of the heavy chains is mediated by a flexible region of the heavy chain, known as the hinge region. Fragments of antibody molecules can be generated, such as for example, by enzymatic cleavage. For example, upon protease cleavage by papain, a dimer of the heavy chain constant regions, the Fc domain, is cleaved from the two Fab regions (i.e. the portions containing the variable regions).

In humans, there are five antibody isotypes classified based on their heavy chains denoted as delta ($\delta$), gamma ($\gamma$), mu ($\mu$), and alpha ($\alpha$) and epsilon ($\epsilon$), giving rise to the IgD, IgG, IgM, IgA, and IgE classes of antibodies, respectively. The IgA and IgG classes contain the subclasses IgA1, IgA2, IgG1, IgG2, IgG3, and IgG4. Any such antibody that is full length or a portion thereof that is less than full length, e.g., containing a heavy chain, light chain, Fab, $Fab_2$, Fv, or Fc, is contemplated for use in the methods herein. In some aspects, the portion of an antibody can be a single chain variable fragment (scFv) of an antibody. In some embodiments, the antibody is a camelid single domain antibody. In certain aspects, the antibody or portion thereof is conjugated to a fluorophore. In aspects, the antibody is selected from among anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54, anti-CD45 and anti-IgG. In some aspects, the fluorophore is selected from among DyLight488, a Brilliant Violet dye (exemplary of which are BV-421, BV-510, BV-605 and the like), Pacific Blue, Chrome Orange, Brilliant Blue 515, PE, FITC, PE-Cy5.5, PE-Cy7, APC, Alexa647, APC-Alexa700 and APC-Alexa750.

In certain aspects of the methods provided herein, at least one particle of the sample includes a lipid bilayer. In aspects, the particle containing a lipid bilayer can be a membrane vesicle, a lipoprotein, a liposome or an extracellular vesicle.

The optically detectable labels associated with the particles in the samples analyzed according to the methods provided herein can be detected using a number of methods including, but not limited to, visual inspection, microscopy, spectroscopy, fluorescence spectroscopy, fluorescence imaging, imaging flow cytometry or flow cytometry. In certain aspects, the detection is by flow cytometry and the samples are analyzed by flow cytometry.

In aspects, the optically detectable labels used in the analysis by flow cytometry are fluorescent labels. In some aspects, one or more of the particles analyzed according to the methods provided herein includes membrane vesicles, lipoproteins, liposomes, extracellular vesicles or other particles containing a lipid bilayer membrane, or combinations thereof. In aspects, the surface area probe or volume probe that interacts with the particle containing a lipid bilayer membrane is selected from among di-8-ANEPPS, di-4-ANEPPS, F2N12S, FM-143, Cell Mask Orange, Cell Mask Green, Cell Mask Deep Red, a carbocyanine dye or a PKH dye. In some aspects, the surface area probe or volume probe intercalates into the bilayer membrane. In aspects, the surface area probe is di-8-ANEPPS.

In certain aspects of the methods provided herein, the surface area probe or volume probe is added in an amount such that the ratio of the amount surface area probe or volume probe (P) relative to the amount of lipid (L) in the particle, P/L, is adjusted whereby the surface area probe or volume probe interacts with the particles stoichiometrically with respect to particle surface area or volume, respectively. In some aspects, the P/L ratio is between about 0.1 to about 0.25.

In some aspects of the methods provided herein, the molecular marker-specific probe is a fluorophore conjugated to a protein. In some aspects, the protein is selected from among annexin V, cholera toxin B-subunit, anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54 and anti-CD45. In certain aspects, the fluorophore conjugated to the protein conjugates is selected from among Dylight488, a Brilliant Violet dye, Pacific Blue, Chrome Orange, Brilliant Blue 515, PE, rhodamine, FITC, PE-Cy5.5, PE-Cy7, APC, Alexa647, APC-Alexa700 and APC-Alexa750.

In aspects of the methods provided herein, physical separation or isolation of the particles includes filtration, washing the particles or precipitating the particles out of the sample or solution containing the particles. In some aspects, physical separation or isolation of the particles includes centrifugation or ultracentrifugation of the particles.

In aspects of the methods provided herein, the flow cytometer has a configuration whereby light is collected from one side of the flow cell. In some aspects, the flow cytometer has a configuration whereby light is collected from both sides of the flow cell. In certain aspects, the detection range of the flow cytometer is between about 1 fluorescent molecule per particle to about 5, 10, 15, 20, 30, 50, 60, 70, 80, 90, 100, 200, 300, 400, 500, 600, 700, 800, 900, 1000, 1500 or 2000 or more fluorescent molecules per particle. In some aspects, the resolution threshold of the flow cytometer is less than 200 fluorescent molecules per particle. In aspects, the resolution threshold of the flow cytometer is between about 1, 2, 3, 4, 5, 6, 7, 8, 9, 10, 11, 12, 13, 14, 15, 16, 17, 18, 19 or 20 fluorescent molecules per particle to about 50, 100 or 150 fluorescent molecules per particle.

In certain aspects of the methods provided herein, the particle is an extracellular vesicle, and, based on the detected optical signal of the molecular marker-specific probe, the type of molecular marker associated with the extracellular vesicle is determined. In some aspects, the cell and/or tissue of origin of the extracellular vesicle is identified based on the type of molecular marker associated with the extracellular vesicle.

In some aspects of the methods provided herein, one or more optical standard particles can be used to provide improved accuracy in determining the optical intensity of the optically detectable labels associated with the particles. In certain aspects, the optical standard particle can be a particle whose surface area or volume or diameter is predetermined by a method that does not use an optically detectable label, such as NTA, tunable resistive pulse sensing (TRPS), electron microscopy (EM) or other methods. In aspects, the optical standard particle is capable of binding to or otherwise associating with an optically detectable label that is a surface area probe or a volume probe. The optical standard particle can then be contacted with an optically detectable label that is a surface area probe or volume probe and the intensity of the label associated with the optical standard particle obtained, thereby providing a correlation between surface area or volume, respectively, and optical intensity.

In some aspects, the optical standard particle is a particle containing molecular marker molecules that can be bound to or otherwise associated with one or more optically detectable labels that are molecular marker-specific probes. The optical intensity of the molecular marker-specific probe-associated optical standard particle can be standardized against the measured optical intensity of a known external standard, thereby providing a correlation between optical intensity and the number of molecules of molecular marker associated with a particle.

In certain aspects, the optical standard particle is a liposome or other lipid-containing particle. In aspects, the amount of lipid in the lipid-containing optical standard particle is known. In some aspects, the optical standard particle is a silica particle. In aspects, the silica particle includes a lipid bilayer. In some aspects, the optical standard particle is a bead. In some aspects, the bead can capture ligands that can bind to one or more molecular markers associated with a particle. In aspects, the ligand is an antibody. In certain aspects, the ligand is conjugated to an optically detectable label.

In some aspects, the optical standard particle is in a collection or preparation of optical standard particles that include a size distribution of optical reference particles, whereby a regression correlation between a distribution of sizes/surface area and optical intensities of the optical standard particles associated with an optically detectable label can be obtained. In aspects, the optical standard particle is in a collection or preparation of optical standard particles that include a distribution of numbers of molecular markers associated with each particle in the preparation, whereby a regression correlation between a distribution of numbers of molecules of molecular marker per optical standard particle and the optical intensities of the optical standard particles associated with an optically detectable label can be obtained.

In certain aspects, the optical standard particles can be used for the analysis of particles according to the methods provided herein. In some aspects, the analysis is by flow cytometry. In aspects, the optical standard particle is a liposome, or a silica particle that includes a lipid bilayer. In some aspects, the optically detectable label associated with the liposome or the lipid bilayer of the silica particle is di-8-ANEPPS or fluorescently labeled (e.g., with DyLight488) annexin V. In certain aspects, the optical standard particle is a bead that can bind to or otherwise associate with a ligand.

In aspects, the ligand is an antibody. Any antibody as known and as described herein with respect to any aspect of the methods provided herein can be used as a ligand. In some aspects, the antibody is labeled with a fluorophore. In aspects, the antibody is selected from among anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54, anti-CD45 and anti-IgG. In some aspects, the fluorophore is selected from among DyLight488, a Brilliant Violet dye, Pacific Blue, Chrome Orange, Brilliant Blue 515, PE, FITC, PE-Cy5.5, PE-Cy7, APC, Alexa647, APC-Alexa700 and APC-Alexa750.

In certain aspects, the methods provided herein are for simultaneously analyzing a plurality of particles of different size and/or having different molecular markers. In some aspects, the different molecular markers can simultaneously be detected according to the methods provided herein, using optically detectable labels that are distinct from one another for each of the different molecular markers. In aspects, for multispectral analysis of a plurality of particles having a plurality of molecular markers, provided herein is a panel of optical standard particles, each associated with a distinct molecular marker conjugated to a distinct optically detectable label whereby, based on the measured optical intensities of the panel of optical standard particles, the optical intensities of the corresponding optically detectable labels associated with the molecular markers of the particles are measured with improved accuracy (e.g., by facilitating "spectral unmixing"). In some aspects, the analysis is by flow cytometry. In aspects, the panel of optical standard particles includes fluorescent beads. In some aspects, the panel of optical standard particles includes beads that can bind to or otherwise associate with ligands, which in turn can be labeled with a fluorophore. In aspects, the ligand is an antibody. In aspects, the antibody is selected from among anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54, anti-CD45 and anti-IgG. In some aspects, the fluorophore is selected from among DyLight488, a Brilliant Violet dye, Pacific Blue, Chrome Orange, Brilliant Blue 515, PE, FITC, PE-Cy5.5, PE-Cy7, APC, Alexa647, APC-Alexa700 and APC-Alexa750.

The size of an optical standard particle for use in the methods provided herein can be between about 20 nm to about 1, 2, 3, 4, 5, 10 or more microns. In some aspects, the size of the optical standard particle is between about 20 nm to about 5 microns, about 30 nm to about 3 microns, about 40 nm to about 2 microns, about 50 nm to about 1 micron, about 50 nm to about 500 nm, about 50 nm to about 450 nm, about 50 nm to about 400 nm, about 100 nm to about 450 nm, or about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 nm.

In aspects of the methods provided herein, an optical standard particle that is not associated with an optically detectable label can be used, thereby improving accuracy by correcting the background optical signal obtained from the particle alone. In certain aspects, the optical standard particle is a bead. In aspects, the bead is coated with, bound to, or otherwise associated with a molecule. In some aspects, the molecule is a polymer. In certain aspects, the polymer is polyethylene glycol (PEG). In aspects, the polymer is a protein that does not associate with an optically detectable label. In certain aspects, the protein is BSA.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIGS. 1A to 1F show the detection of fluorescently labeled particles by flow cytometry using a fluorescent trigger (FIGS. 1A to 1C) or a side scatter trigger (FIGS. 1D to 1F). FIG. 1A and FIG. 1D depict the 488 SSC peaks corresponding to 0.53 µm and 0.11 µm fluorescent beads. FIG. 1B and FIG. 1E depict the Nile Red fluorescence peaks corresponding to 0.53 µm and 0.11 µm fluorescent beads. FIG. 1C and FIG. 1F depict a plot of the 488 SSC peaks against the Nile Red fluorescence peaks.

FIGS. 2A to 2H show a comparison of size distribution profiles of vesicles using fluorescence intensity histograms obtained by flow cytometry (FIGS. 2A to 2D) or using nanoparticle diameter population histograms obtained by nanoparticle tracking analysis (NTA) (FIGS. 2E to 2H). FIG. 2A and FIG. 2E depict fluorescence intensity histograms of di-8-ANEPPS stained vesicles prepared by extrusion through polycarbonate membrane filters with average pore sizes of 200 nm. FIG. 2B and FIG. 2F depict fluorescence intensity histograms of di-8-ANEPPS stained vesicles prepared by extrusion through polycarbonate membrane filters with average pore sizes of 100 nm. FIG. 2C and FIG. 2G depict fluorescence intensity histograms of di-8-ANEPPS stained vesicles prepared by extrusion through polycarbonate membrane filters with average pore sizes of 80 nm. FIG. 2D and FIG. 2H depict fluorescence intensity histograms of di-8-ANEPPS stained vesicles prepared by extrusion through polycarbonate membrane filters with average pore sizes of 50 nm.

FIGS. 4A to 4F show the measurement of extracellular vesicles (EVs) in rat plasma by NTA (FIGS. 4A to 4C) or fluorescence triggered flow cytometry (FIGS. 4D to 4F), with their diameter calibrated using synthetic liposomes as reference particles. FIG. 4A, FIG. 4B and FIG. 4C depict nanoparticle population size distributions of three different rat plasma samples using NTA. FIG. 4D, FIG. 4E and FIG. 4F depict nanoparticle population size distributions of the three different rat plasma samples using flow cytometry. FIG. 4G shows plasma nanoparticle (EV) concentrations as measured by NTA and flow cytometry for eight animals.

FIG. 5A shows the measurement of surface molecular markers of EVs in control plasma stained with di-8-ANEPPS and DyLight488-Annexin V. FIG. 5B shows the measurement of surface molecular markers of EVs in control plasma stained with di-8-ANEPPS and DyLight488-anti-CD61. FIG. 5C shows the measurement of surface molecular markers of EVs in ionophore-treated platelet rich plasma stained with di-8-ANEPPS and DyLight488-Annexin V. FIG. 5D shows the measurement of surface molecular markers of EVs in ionophore-treated platelet rich plasma stained with di-8-ANEPPS and DyLight488-anti-CD61.

FIGS. 9A to 9E depict measurements performed on synthetic liposomes having known amounts of associated lipid, and FIG. 9F depicts measurements performed on a sample of platelet-poor plasma (PPP). FIG. 9A is a fluorescence spectrum of bulk suspensions of di-8-ANEPPS (500 nM) in buffer alone (HBS; 150 mM NaCl, 10 mM HEPES pH 7.4) or buffer plus two concentrations of synthetic lipid vesicles (50 uM and 3 uM). FIG. 9B is a normalized representation of the measurements depicted in FIG. 9A. FIG. 9C depicts the ratio of intensities at 690 to 610 nm measured at several different probe to lipid ratios. FIG. 9D depicts histograms of the population distributions of the ratio of intensities of the synthetic vesicles measured through the 690/50 nm and 610/20 nm filters (690/610 ratio), for high (0.16) and low (0.01) probe to lipid ratios. FIG. 9E depicts the ratio of intensities at 690 to 610 nm measured by flow cytometry of synthetic vesicle preparations having several different probe to lipid ratios. FIG. 9F depicts the median 690/610 ratio at two dilutions of human PPP.

FIG. 10A depicts buffer alone, FIG. 10B depicts buffer+probe, FIG. 10C depicts a sample preparation containing synthetic vesicles stained with probe, FIG. 10D depicts the sample preparation of FIG. 10C with added detergent (Triton X-100; TX100), FIG. 10E depicts a platelet-free plasma preparation stained with dye.

FIGS. 11A to 11D depict the analysis of EVs in human plasma using multiple markers. FIG. 11A depicts measurements performed on synthetic liposomes, FIG. 11B depicts measurements performed on synthetic liposomes to which detergent is added (Triton X-100; TX100), FIG. 11C depicts measurements performed on platelet-rich plasma (PRP) supernatant and FIG. 11D depicts measurements performed on platelet-rich plasma (PRP) supernatant to which detergent is added (Triton X-100; TX100).

DETAILED DESCRIPTION

Figure 3:
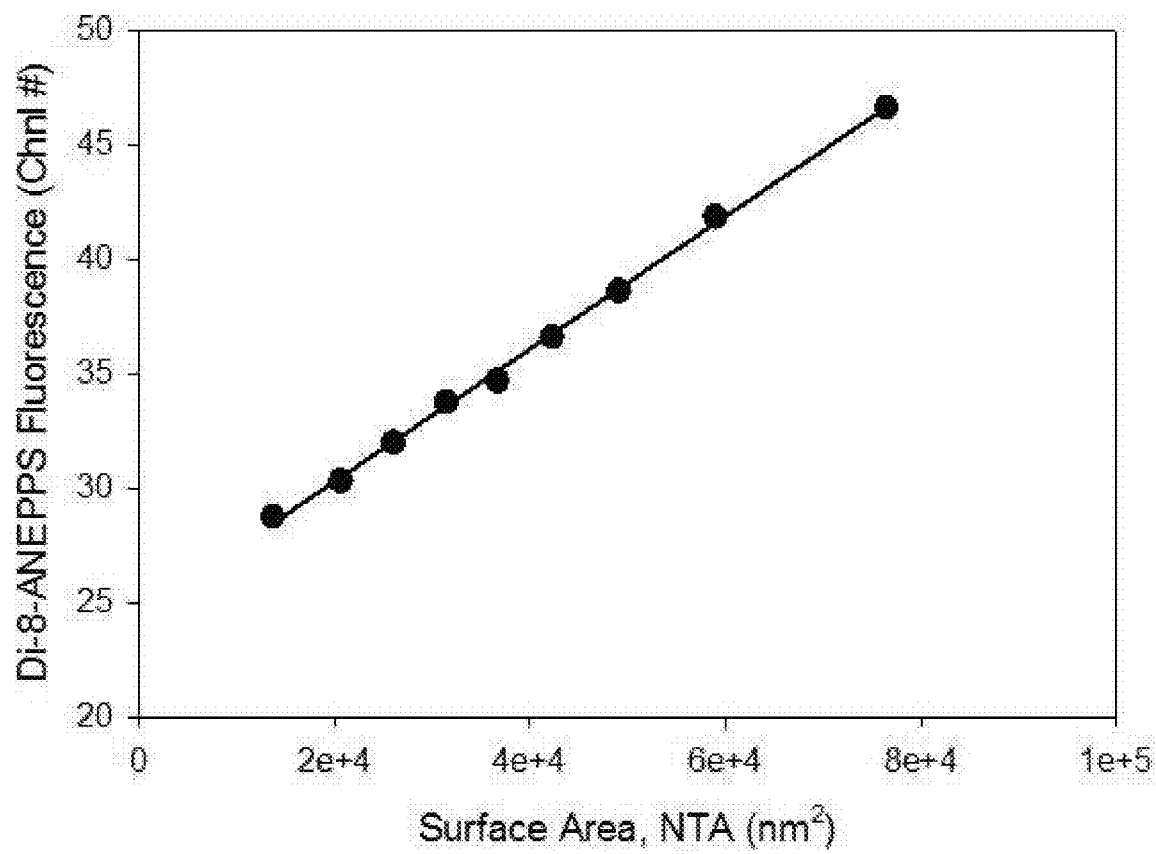
FIG. 3 is a graph depicting the relationship between fluorescence intensity of a fluorescent probe associated with vesicles, and vesicle surface area.
Figure 5A:
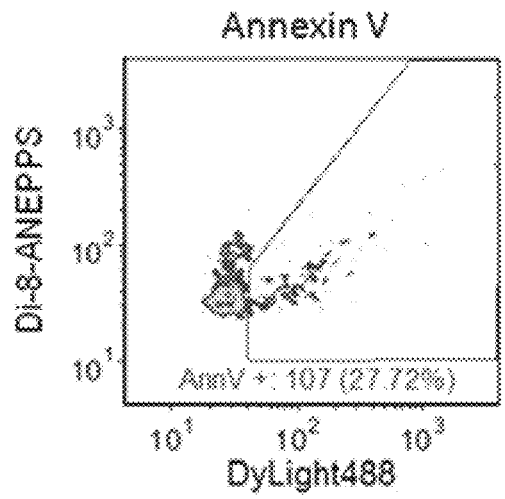
FIGS. 5A to 5D show the measurement of surface molecular markers of EVs in plasma from control plasma or ionophore-treated platelet rich plasma stained with di-8-ANEPPS and DyLight488-Annexin V or Dylight488-anti-CD61.
Figure 5B:
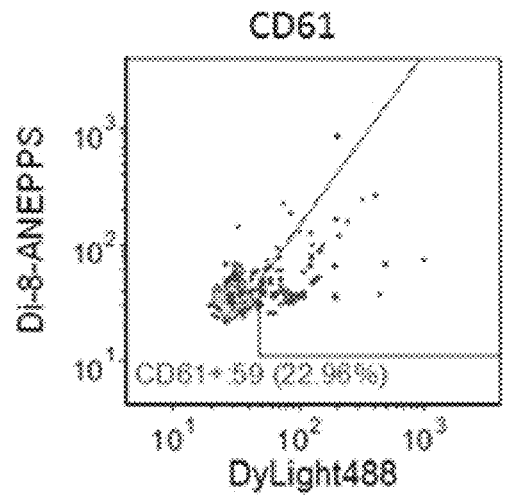
Figure 5C:
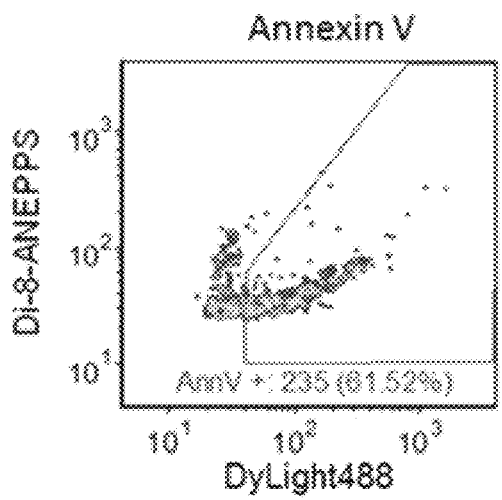
Figure 5D:
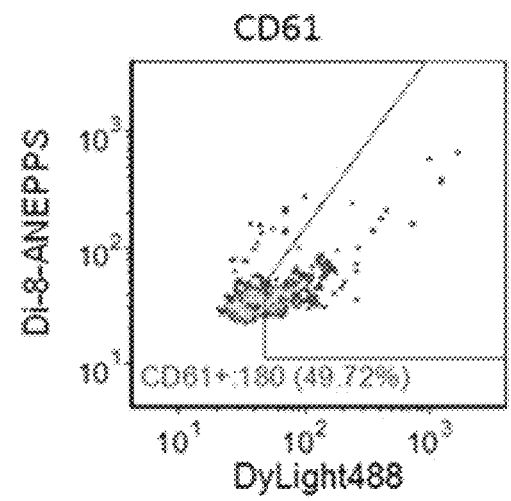

Provided herein are optical methods for analyzing particles or vesicles with improved efficiency and accuracy. The methods provided herein can be used to analyze particles or vesicles of size ranging from about 1 nm in diameter to 100 microns (µm) or more in diameter. The analysis can include, but is not limited to, detection, quantitation, sizing and characterization of the particles, which can include determining the identity, i.e., molecular content and origin of the particles (e.g., cell/tissue of origin of an extracellular vesicle). The improved efficiency and accuracy of the methods provided herein permits the analysis of a wider range of particle sizes, including nanoparticles or nanovesicles of about 200 nm or less in diameter.

Overview of the Methods

Exemplary aspects of the methods provided herein are now described. Samples containing particles of interest, including microparticles, nanoparticles, liposomes, vesicles (unilamellar, multilamellar, e.g.), lipoproteins, endosomes, viruses, viral particles, virus-like particles, apoptotic bodies and/or extracellular vesicles (EVs), are either at a particle concentration or are diluted to a sample particle concentration that facilitates optimal staining with an optically detectable label, detection of the label and analysis. For example, when the analysis is by flow cytometry, the samples are at, or can be diluted to, a final particle concentration of about $1\times10^8$ to about $1\times10^{10}$ particles/μl.

The optimal dilution can, in embodiments, be determined by serial dilution of the sample in the presence of a constant amount of optically detectable label, thereby determining the optimal dilution (particle concentration) for enhanced signal from the label associated with the particles and low to negligible background signal from the unbound or free label. The particle concentration of the diluted sample that produces optimal enhanced signal relative to background noise can independently be measured by a technique not involving contact with the optically detectable label, such as nanoparticle tracking analysis (NTA), transmission electron microscopy (TEM) or resistive pulse spectroscopy (RPS), to determine the equivalent particle concentration of the optimally diluted sample.

For example, when the sample is plasma, the dilution factor for analyzing membrane vesicles (e.g., EVs) in the plasma is high due to the presence of high concentrations of proteins that can non-specifically compete with the vesicles for binding/association of the optically detectable label. In such instances, when the sample is plasma, the dilution factor can be of the order of between 100-fold to 200-fold, or even 300, 400, 500, 600, 700, 800, 900, 1000, 5000, 10,000, 20,000, 30,000, 40,000, 50,000, 60,000, 70,000, 80,000, 90,000, 100,000-fold or more. When the sample is cerebrospinal fluid, which has lower amounts of protein, the dilution factor for the analysis of membrane vesicles in the fluid can be lower, of the order of, for example, 20-fold, or in the range of between 5, 10, 15, 20, 25, 30, 25, 40, 45, 50, 55, 60, 65, 70, 75, 80, 85, 90, 95, 100-fold or higher. In general, depending on the sample, the dilution factor can be anywhere from about 2-fold to about 5, 10, 15, 20, 25, 30, 25, 40, 45, 50, 55, 60, 65, 70, 75, 80, 85, 90, 95, 100, 200, 300, 400, 500, 600, 700, 800, 900, 1000, 5000, 10,000, 20,000, 30,000, 40,000, 50,000, 60,000, 70,000, 80,000, 90,000, 100,000-fold or higher. In certain embodiments, no dilution of the sample may be needed.

In some embodiments, the sample can be treated to remove, in whole or in part, matter other than the particles such as undesired large particulates, cells, cellular debirs or other undissolved subject matter that does not include the particles. For example, to remove large particulates or cellular debris from a biological sample such as blood or plasma or cerebrospinal fluid, the sample can be subjected to centrifugation at 2500 g for one, two, three or more times, each step of centrifugation being performed for about 1 minute to about 20 minutes or more, for about 1, 2, 3, 4, 5, 6, 7, 8, 9, 10, 11, 12, 13, 14, 15, 16, 17, 18, 19 or 20 or more minutes. In some embodiments, the centrifugation is performed two times for about 10 minutes each at 2500 g. In embodiments, the centrifugation is performed prior to dilution for optimal staining with an optically detectable label.

The sample containing an adjusted particle concentration as described above can be stained using one or more optically detectable labels. The optically detectable labels and/or staining conditions are selected such that binding or other association of the labels to the particles is stoichiometric and/or saturable with respect to one or more of: (a) the surface area or volume of the particle; or (b) one or more specific molecular markers to which the optically detectable labels are bound, whereby the optical signal from the label is proportional to the surface area/volume and/or number of molecular markers of the particle, thereby providing information about the size, features and/or origin of the particle. The staining can be performed before, after or contemporaneously with the sample dilution. The optically detectable label can, in some embodiments, be a probe that can intercalate into the particle stoichiometrically with respect to the surface area and/or volume of the particle, thereby producing an optical signal that is proportional to the surface area and/or volume of the particle. For example, in particles that are lipid vesicles (e.g., liposomes or EVs), the fluorescent label di-8-ANEPPS (4-[2-[6-(dioctylamino)-2-naphthalenyl]ethenyl]1-(3-sulfopropyl)-pyridinium) can bind to lipid membranes in a stoichiometric manner that is proportional to the surface area or volume of the liposomes. An exemplary volume probe for use in any of the methods herein is carboxyfluorescein succinimidyl ester (CFSE).

In certain embodiments, the optically detectable label specifically binds or otherwise associates stoichiometrically with respect to one or more molecular components/markers of the particle (molecular marker-specific probe), thereby providing an optical signal that is specific for the marker and permits identification of the type of particle based on the type of detected marker. In embodiments, the molecular marker-specific probe binds or otherwise associates with the molecular marker in a stoichiometric manner proportional to the number of molecules of molecular marker per particle. As used herein, a "molecular marker" is a molecule that is a specific component or ligand of a particular type of particle. The molecular marker can be present anywhere in the interior or on the surface of the particle, or can be associated with the membrane when particle is a vesicle (e.g., membrane vesicles, liposomes, EVs), and detection of the molecular marker can identify the type of particle associated with the molecular marker. In some embodiments, the molecular marker can be present on the surface of the particle. For example, in particles that are lipid vesicles (e.g., liposomes or EVs), annexin V has a specific binding affinity for phosphatidyl serine (PS), which is a surface molecular marker of many cell-derived EVs, membrane vesicles and liposomes. The number of cell-derived EVs or other PS-containing vesicles can be determined by staining with an optically labeled annexin V, e.g., annexin V conjugated to the fluorescent label, Dylight488-succinimidyl ester. As another example, platelet-derived extracellular vesicles (EVs) have CD61 as a molecular marker, which can be detected using anti-CD61 that has been labeled with an optically detectable label. Identifying the type of particle can include identifying its origin or source. For example, when the particle is an EV, as indicated in the aforementioned example, the detection of CD61 in the EV can identify the EV as originating from platelets.

In some embodiments, the particles can be stained with both a surface area probe or volume probe for optical detection, and a molecular marker-specific optical label. The concentration of the optically detectable label, the choice of staining buffer, the temperature during staining and/or the staining time can be adjusted to achieve stoichiometric incorporation of the optically detectable label in the interior and/or surface of the particle. Any optically detectable label that shows enhanced intensity (e.g., color, fluorescence, luminescence, bioluminescence, chemiluminescence and light scatter) when bound to the particles relative to the free label can be used in the methods provided herein.

The term "stoichiometric," as used herein, refers to the association or binding of a surface area/volume probe or molecular marker-specific probe to a particle in a manner that is proportional to the surface area/volume of a particle (for a surface area/volume probe) or the number or concentration of molecules of molecular marker-specific probe associated with the particle, whereby, based on the intensity of the signal generated from the optically detectable label associated with the probe, the surface area of the particle or the number/concentration of molecules of marker-specific probe, respectively, can be determined.

The terms "saturable," "saturated,' "saturating," "approaching saturation," as used herein, refer to the amount of probe (surface area or molecular-marker specific) which, when associated with or bound to a particle, generates a signal from an optically detectable label associated with the probe that does not substantially increase when more probe is added to the sample containing the particle. For example, when the optically detectable label associated with the probe is bound to the particle in a saturating amount, adding further amounts of the probe does not substantially increase the signal generated by the optically detectable label by more than 0% 0.05%, 0.1%, 0.2%, 0.3%, 0.4%, 0.5%, 0.6%, 0.75. 0.8%. 0.9%, 1.0%, 1.5%, 2.0%, 2.5%, 3.0%, 3.5%, 4.0%, 4.5%, 5.0%, 5.5%, 6%, 6.5%, 7.0%, 7.5%, 8.0%, 8.5%, 9.0%, 9.5%, 10.0% or more, up to 15% or 20%. In embodiments of the methods provided herein, stoichiometric binding/association of the surface probe or molecular marker-specific probe to a particle is achieved when the binding/association of the probe to/with the particle is in an amount that is saturating for the signal intensity of the optically detectable label associated with the probe. In some embodiments of the methods provided herein, the optically detectable label used in the methods is saturable when bound/associated as a probe to a particle. For example, di-8-ANEPPS is a saturable optically detectable surface area probe.

In lipid-containing particles such as liposomes, EVs or other lipid-containing vesicles, when probe is added to such particles, the probe often becomes associated with the particles by intercalation into the lipid bilayer membranes. In such embodiments, as more probe is added to the particles, the optimal probe to lipid ratio is considered as "approaching saturation" rather than becoming saturated because saturation can lead to self-quenching among the large number of intercalated probe molecules. Thus, as used herein a probe amount "approaching saturation" or that "approaches saturation" can be used interchangeably with "saturable," "saturated,' "saturating" and the like and refers to the amount of probe (surface area or molecular-marker specific) which, when associated with or bound to a particle, generates a signal from an optically detectable label associated with the probe that does not substantially increase when more probe is added to the sample containing the particle.

In some aspects, for analysis of the stained particles, the methods provided herein do not include a physical separation or isolation. As used herein, "physical separation or isolation" means that the non-particle reaction components of the staining reaction are substantially removed from the presence of the stained particles (e.g., the container in which the stained particles are present) by methods such as filtration, precipitation, washing or centrifugation, including ultracentrifugation. As used herein, "non-particle reaction components" or "non-particle components" of the staining reactions refers to all components of the staining reaction other than the particles, some or all of which include bound (particle-associated) optically detectable label; the non-particle components can include buffers, salts, surfactants, unbound (free) optically detectable label and other components that are present in the staining reaction by which one or more optically detectable labels are incorporated into the particles.

Substantial removal of the non-particle components of the staining reaction means that at least about 50, 60, 70, 75, 80, 85, 90, 91, 92, 93, 94, 95, 96, 97, 98, 99 or more percent of the non-particle components of the staining reaction, i.e., substantially all components of the reaction other than the stained particles, are removed by one or more physical separations, e.g., washing or centrifugation. In the methods provided herein, after staining, the resulting stained samples can be diluted by a factor sufficient to reduce the background signals associated with optically detectable labels that are not bound to or associated with the particles, without physical separation or isolation.

Without being bound by theory, the analysis of the stained particles by dilution of the staining reaction mix, without a physical separation or isolation, can provide improved efficiency by reducing the number of steps used to process the particles prior to analysis. In addition, the analysis of microparticles or nanoparticles generally involves handling small volumes of samples containing the particles and the repeated washing or centrifugation/ultracentrifugation of small volumes can lead to loss of a fraction of the particles, thereby reducing the accuracy of analysis. The dilution can be by a factor sufficient to minimize interference from the signal associated with free optically detectable label that is not associated with the particle, while maintaining enhanced signal from the optically detectable label that is bound to or otherwise associated with the particle. Thus, in embodiments of the methods provided herein, particle-associated label is analyzed in the presence of free label, the free label generating a minimal background signal that does not interfere with the detection of signal generated by the particle-associated optically detectable label. The dilution also can be by a factor whereby multiple particles are not detected simultaneously, i.e., there is minimal to no "coincidence." For example, the dilution can be by a factor of anywhere from about 2-fold to about 5, 10, 15, 20, 25, 30, 25, 40, 45, 50, 55, 60, 65, 70, 75, 80, 85, 90, 95, 100, 200, 300, 400, 500, 600, 700, 800, 900, 1000, 5000, 10,000, 20,000, 30,000, 40,000, 50,000, 60,000, 70,000, 80,000, 90,000, 100,000-fold or higher, depending on the sample. In some embodiments, no dilution of the staining reaction solution may be needed. In an exemplary embodiment, when the sample is plasma, the dilution of a sample stained with 500 nM di-8-ANEPPS and 50 nM molecular marker-specific probe can be by a factor of about 1000.

The label-bound particles in the sample that is diluted, post-staining, as described above, can be detected, characterized (e.g., its molecular components identified and/or its origin identified—e.g., if the particle is an EV, its cell/tissue of origin can be identified) and/or quantitated based on detection of the bound optically-detectable label. Any label that can be detected by optical means can be used for analyses of the particles. The sample can be analyzed by visual inspection or can be illuminated by an instrument capable of detecting an optically detectable label associated with a particle. The illumination wavelength can be tailored to detection of a particular particle-associated optically detectable label, whether the label is a surface area probe or volume probe, or a molecular marker-specific probe. The intensity of the signal from the particle-associated optically detectable label can be measured by the instrument detecting such signal or by a separate instrument capable of measuring the intensity of a signal from an optically detectable label associated with a particle. Exemplary optical elements for selecting and dispersing light can include, but are not limited to, band pass filters, dichroic mirrors or optical gratings for filtering or dispersing light onto a detector. Exemplary detectors can include, but are not limited to, a photomultiplier tube (PMT), an avalanche photodiode, an avalanche photodiode array, a silicon-PMT, a hybrid PMT, a photodiode array, a charged cathode device (CCD), an electron multiplied CCD, a CMOS sensor detector, or any suitable photodetector. The measured intensity can be used to characterize the particles in the sample according to presence or absence of the particle, type/identity of the particle, source/origin of the particle, number of molecules of molecular marker on the particle, size of the particle or quantity of the particle.

Samples

Samples that contain particles for analysis according to the methods provided herein generally include particles in a liquid medium. The particles can be analyzed by detection, identification, characterization according to the presence of one or more molecular markers associated with the particles, or characterization according to the size of the particles. Any samples containing particles in a liquid can be analyzed according to the methods provided herein.

Any aqueous or organic liquid medium containing particles, where the particles are not dissolved in the liquid medium, are contemplated for use in the methods herein. The liquid medium can be a solution that includes solutes dissolved in the liquid medium, such as buffers. In some embodiments, the samples include a suspension of particles, or a colloidal suspension of particles, in the liquid medium. Exemplary liquid media containing particles that can be analyzed according to the methods provided herein include, but are not limited to, blood, milk, water, solutions containing particles such as membrane vesicles, lipoproteins, viruses, virus-like particles, apoptotic bodies, synthetic liposomes or extracellular vesicles, and biological fluids other than blood such as plasma, serum, urine, saliva, seminal fluid, lavages (e.g., bronchoalveolar, gastric, peritoneal, ductal, ear, arthroscopic), cervical fluid, cervicovaginal fluid, cerebrospinal fluid, vaginal fluid, breast fluid, breast milk, synovial fluid, semen, seminal fluid, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum or fractions or components thereof.

In some embodiments, the sample containing particles is a biological sample. In embodiments, the biological sample includes a biological fluid. The biological fluid in the biological sample can include, but is not limited to, blood, plasma, serum, urine, saliva, seminal fluid, lavages (e.g., bronchoalveolar, gastric, peritoneal, ductal, ear, arthroscopic), cervical fluid, cervicovaginal fluid, cerebrospinal fluid, vaginal fluid, breast fluid, breast milk, synovial fluid, semen, seminal fluid, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum or fractions or components thereof. In certain embodiments, the biological fluid is blood, plasma or serum. In some embodiments, the biological fluid is cerebrospinal fluid.

In certain embodiments, the biological sample is extracted from a cell or tissue sample of a subject, such as a biopsy sample (e.g., cancer biopsy), or is extracted from normal or cancer cell samples or normal or cancer tissue samples where the cell or tissue samples can be derived, e.g., from the liver, lung, kidney, spleen, pancreas, colon, skin, bladder, eye, brain, esophagus, head, neck, ovary, testes, prostate, the like or combination thereof. In some embodiments, the biological sample that is extracted from a cell or tissues sample of a subject includes a biological fluid.

In some embodiments, the biological sample includes particles derived from a cancer biopsy, a cancer cell or a cancer tissue. Cancer biopsy samples, cancer cell types or cancer tissue types from which particles can be present in the biological sample include, but are not limited to, liver cells (e.g., hepatocytes), lung cells, spleen cells, pancreas cells, colon cells, skin cells, bladder cells, eye cells, brain cells, esophagus cells, cells of the head, cells of the neck, cells of the ovary, cells of the testes, prostate cells, placenta cells, epithelial cells, endothelial cells, adipocyte cells, kidney cells, heart cells, muscle cells, blood cells (e.g., white blood cells, platelets), the like and combinations of the foregoing. In embodiments, the cancer is a glioblastoma. In certain embodiments, the cancer is ovarian, lung, bladder or prostrate cancer. In some embodiments, the biological sample that includes particles derived from a cancer biopsy, a cancer cell or a cancer tissue further includes a biological fluid. In embodiments, the biological fluid is blood, plasma, serum, saliva, urine or cerebrospinal fluid. In some embodiments, the cancer is ovarian, lung, bladder or prostrate cancer and the biological fluid is saliva, urine or serum. In certain embodiments, the cancer is brain cancer. In some embodiments, the cancer is brain cancer and the biological fluid is cerebrospinal fluid. In embodiments, the brain cancer is glioblastoma.

In some embodiments, a sample can be blood and sometimes a blood fraction (e.g., plasma or serum). As used herein, the term "blood" encompasses whole blood or any fractions of blood, such as serum and plasma as conventionally defined, for example. Blood also contains buffy coats. Buffy coats sometimes are isolated by utilizing a ficoll gradient. Buffy coats can comprise white blood cells (e.g., leukocytes, T-cells, B-cells, platelets, and the like) and samples extracted from buffy coats can include particles, e.g., extracellular vesicles (EVs), derived from these cells. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. In some embodiments, a sample obtained from a subject can contain cellular elements or cellular remnants. In some embodiments, cancer cells may be included in the sample. In embodiments, the sample is obtained from a human subject. In certain embodiments, the human subject is a cancer patient and in some embodiments, the human subject does not have cancer.

Particles

Any particles that can bind to or otherwise associate with an optically detectable label are contemplated for analysis according to the methods provided herein. The particles can occur in nature, or can be synthetic or artificially prepared. The particles described herein and elsewhere in this application can be the particles of interest, i.e., the particles that are desired to be analyzed by the methods, or they can be used as optical standard particles for improved accuracy of measurement of the optical intensity.

Inert Particles

In certain embodiments, the particles can be inert particles that can associate with an optically detectable label or can be modified for association with an optically detectable label. Such particles can include metalloids, non-limiting examples of which include boron and silicon, the like and combinations thereof. A particle sometimes can include, consist essentially of, or consist of, silica (e.g., silicon dioxide (i.e., $SiO_2$)). A particle sometimes can include one or more metals including, but not limited to, iron, gold, copper, silver, platinum, aluminum, titanium, tantalum, vanadium, the like, oxides thereof and combinations thereof. A particle sometimes can include glass (e.g. controlled-pore glass (CPG)), nylon, Sephadex®, Sepharose®, cellulose, a magnetic material or a plastic material. A particle sometimes is a polymer or includes more than one polymer. Non-limiting examples of polymers include polypropylene (PP), polyethylene (PE), polyamide, high-density polyethylene (HDPE), low-density polyethylene (LDPE), polyester, polyvinylidenedifluoride (PVDF), polyethylene teraphthalate (PET), polyvinyl chloride (PVC), polytetrafluoroethylene (PTFE), polystyrene (PS), high-density polystyrene, acrylnitrile butadiene styrene copolymers, crosslinked polysiloxanes, polyurethanes, (meth)acrylate-based polymers, cellulose and cellulose derivatives, polycarbonates, ABS, tetrafluoroethylene polymers, poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyorthoesters, polycyanoacrylates, polycaprolactone, the like, copolymers thereof and combinations of the foregoing.

The particles can be solid particles or particles that contain internal voids. The particles can have a regular (e.g., spheroid, ovoid) or irregular shape (e.g., rough, jagged), and sometimes can be non-spherical (e.g., angular, multi-sided).

Membrane Vesicles

In embodiments of the methods provided herein, the particles include membrane vesicles. A membrane vesicle, as used herein, refers to a particle that includes fluid enclosed within a lipid-containing outer shell. The enclosed fluid can include additional components, such as proteins and small molecules. A lipid molecule typically includes at least one hydrophobic chain and at least one polar head. When exposed to an aqueous environment, lipids often will self assemble into structures that minimize the surface area exposed to a polar (e.g., aqueous) medium. Lipids sometimes assemble into structures having a single or monolayer of lipid enclosing a non-aqueous environment, and lipids sometimes assemble into structures comprising a bilayer enclosing an aqueous environment. In a monolayer structure, the polar portion of lipids (e.g., the head of the molecule in the case of phospholipids and other lipids commonly found in cell substrates) often is oriented towards the polar, aqueous environment, allowing the non-polar portion of the lipid to contact the non-polar environment.

A vesicle also can be a lipid bilayer configured as a spherical shell enclosing a small amount of water or aqueous solution and separating it from the water or aqueous solution outside the vesicle. Membrane vesicles also can contain a fluid with, optionally, one or more molecular components, enclosed within a lipid bilayer. Because of the fundamental similarity to a cell wall, vesicles have been used to study the properties of lipid bilayers. Vesicles also are readily manufactured. A sample of dehydrated lipid spontaneously forms vesicles, when exposed to water. Spontaneously formed vesicles can be unilamelar (single-walled) or multilamellar (many-walled) and are of a wide range of sizes from tens of nanometers to several micrometers. A lipid bilayer typically includes a sheet of lipids, generally two molecules thick, arranged so that the hydrophilic phosphate heads point towards a hydrophilic aqueous environment on either side of the bilayer and the hydrophobic tails point towards the hydrophobic core of the bilayer. This arrangement results in two "leaflets" that are each a single molecular layer. Lipids self-assemble into a bilayer structure due to the hydrophobic effect and are held together by non-covalent forces that do not involve formation of chemical bonds between individual molecules.

In some embodiments, lipid bilayers are natural, and in certain embodiments lipid bilayers are artificially generated. Natural bilayers often are made mostly of phospholipids, which have a hydrophilic head and two hydrophobic tails (e.g., lipid tails), and form a two-layered sheet as noted above, when exposed to water or an aqueous environment. The center of this bilayer contains almost no water and also excludes molecules like sugars or salts that dissolve in water, but not in oil. Lipid tails also can affect lipid composition properties, by determining the phase of the bilayers, for example. A bilayer sometimes adopts a solid gel phase state at lower temperatures and undergoes a phase transition to a fluid state at higher temperatures. Artificial bilayers of membrane vesicles can be any bilayers assembled through artificial means, as opposed to bilayers that occur naturally (e.g., cell walls, lipid bilayers that cover various sub-cellular structures).

The presence of certain lipids or proteins sometimes can alter the surface chemistry of bilayers (e.g., viscosity or fluidity of lipid bilayers). Phospholipids with certain head groups can alter the surface chemistry of a bilayer. Non-limiting examples of bilayer constituents that can alter the surface chemistry of bilayers include fats, lecithin, cholesterol, proteins, phospholipids (e.g., phosphatidic acid (phosphatidate), phosphatidylethanolamine (e.g., cephalin), phosphatidylcholine (e.g., lecithin), phosphatidylserine, and phosphoinositides such as phosphatidylinositol (PI), phosphatidylinositol phosphate (PIP), phosphatidylinositol bisphosphate (PIP2) and phosphatidylinositol triphosphate (PIP3), phosphatidylglycerol, ceramide phosphorylcholine, ceramide phosphorylethanolamine, ceramide phosphorylglycerol), phosphosphingolipids, glycolipids including gangliosides, surfactants, the like and combinations thereof.

Different types or forms of lipid compositions (e.g., monolayers and/or bilayers) can be found naturally or generated artificially. Non-limiting examples of lipid compositions include monolayers (e.g., micelles), supported lipid bilayers, linear lipid bilayers and the like.

A protein, glycoprotein, glycolipid, nucleic acid or carbohydrate often is inserted into a structure (e.g., monolayer and/or bilayer) formed by the lipid or amphiphilic material composition, or is encapsulated within the interior of the structure (membrane vesicle or other particle as described herein). A protein that is inserted into the structure can be water soluble, detergent-solubilized or incorporated into a lipid bilayer (e.g., vesicle, liposome) or a lipid monolayer (e.g., micelle) in some embodiments.

Some types of membrane vesicles can include lipoproteins, endosomes, apoptotic bodies, viruses, virus particles and virus-like particles. Endosomes are membrane-bound vesicles, formed via a complex family of processes collectively known as endocytosis, and found in the cytoplasm of virtually every animal cell. The basic mechanism of endocytosis is the reverse of what occurs during exocytosis or cellular secretion or the release of extracellular vesicles (EVs, e.g., ectosomes, exosomes) as it involves the invagination (folding inward) of a cell's plasma membrane to surround macromolecules or other matter diffusing through the extracellular fluid. The encircled foreign materials are then brought into the cell, and following a pinching-off of the membrane (termed budding), are released to the cytoplasm of the cell in a sac-like vesicle. The sizes of the endosomal vesicles can vary and generally are nanoparticles. Endosomes larger than 100 nanometers in diameter typically are referred to as vacuoles.

Viruses, virus particles and virus-like particles can include a lipid bilayer and, in embodiments, carry proteins on their surface, including envelope proteins, coat proteins and cellular membrane proteins. "Naked viruses" generally lack surface proteins and can be modified to include surface proteins (e.g., by insertion of the proteins into the outer lipid bilayer of the virus). Viruses include for example, but are not limited to, retroviruses and DNA viruses. Virus particles can include the fully or partially assembled capsid of a virus. A viral particle may or may not contain nucleic acid. Virus particles generally include one or more of or two or more of the following: genetic material made from either DNA or RNA; a protein coat that protects the genetic material; and in some embodiments an envelope of lipids that surrounds the protein coat when they are outside a cell.

Lipoproteins are globular, micelle-like particles that include a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, which transport dietary lipids from intestine to tissues; very low density lipoproteins (VLDL); intermediate density lipoproteins (IDL); low density lipoproteins (LDL); all of which transport triacylglycerols and cholesterol from the liver to tissues; and high density lipoproteins (HDL), which transport endogenous cholesterol from tissues to the liver. Lipoprotein particles undergo continuous metabolic processing and can have variable properties and compositions. Lipoprotein densities can increase without decreasing particle diameter because the density of their outer coatings is less than that of the inner core. The protein components of lipoproteins are known as apolipoproteins. At least nine apolipoproteins are distributed in significant amounts among the various human lipoproteins.

Apoptotic bodies are released during apoptosis (programmed cell death). When a cell undergoes apoptosis, the structure of the cell breaks down. The breakdown components are packaged into apoptotic bodies, which can include membrane bound "sacs" that contain nucleic acids, proteins and lipids. When the ability of neighboring cells and/or macrophages to clear these breakdown components is overwhelmed by high numbers of apoptotic bodies ("excessive" apoptosis) or defects in clearing the bodies, apoptotic bodies are released into circulation and can be detected in blood plasma or serum (Holdenrieder et al, 2001a; Holdenrieder et al, 2001b; Holdenrieder et al, 2001c; Lichtenstein et al, 2001). Above-average levels of apoptotic bodies in the bloodstream have been correlated, e.g., with the presence tumors and cancers. An "apoptotic body" can contain nucleic acids, proteins, lipids, but no nucleus, although it may contain fragmented nuclei. In general, apoptotic bodies are less than 10 microns in size, generally between about 25 nm, 50 nm, 75 nm or 100 nm to about 150 nm, 200 nm, 250, 300 nm, 350 nm, 400 nm, 400 nm, 500 nm, 1 micron, 1.5 micron, 2 microns, 2.5 microns, 3 microns, 3.5 microns, 4 microns, 4.5 microns or 5 microns in size.

Liposomes

A liposome is an artificially prepared vesicle that includes at least one lipid bilayer and also can be made of naturally occurring or synthetic lipids, including phospholipids. Liposomes can include MLV (multilamellar vesicles), SUV (Small Unilamellar Vesicles), LUV (Large Unilamellar Vesicles) and GUV (Giant Unilamellar Vesicles). Unilamellar vesicles generally contain a single lipid bilayer, while multilamellar vesicles generally include more than one lipid bilayer. As used herein, "multivesicular liposome" refers to man-made, microscopic lipid vesicles containing lipid membranes enclosing multiple concentric or non-concentric aqueous chambers.

Various types of lipids can be used to make liposomes, including neutral lipids and amphipathic lipids. Examples of neutral lipids include diglycerides, such as diolefin, dipalmitolein; propylene glycol esters such as mixed diesters of caprylic/capric acids on propylene glycol; triglycerides such as triolein, tripalmitolein, trilinolein, tricaprylin and trilaurin; vegetable oils, such as soybean oil; lard or beef fat; squalene; tocopherol; and combinations thereof. Examples of amphipathic lipids include those with net negative charge, zero net charge, and net positive charge at pH 7.4. These include zwitterionic, acidic or cationic lipids. Such exemplary amphipathic lipids include, but are not limited to, phosphatidylglycerol (PG), cardiolipin (CL), phosphatidylserine (PS), phosphatidic acid (PA), phosphatidylinositol, phosphatidylcholine (PC), phosphatidylethanolamine (PE), sphingomyelin, diacyl trimethylammonium propane (DI-TAP), DOPC or DC18:1PC=1,2-dioleoyl-sn-glycero-3-phosphocholine; DLPC or DC12:0PC=1,2-dilauroyl-sn-glycero-3-phosphocholine; DMPC or DC14:0PC=1,2-dimyristoyl-sn-glycero-3-phosphocholine; DPPC or DC16:0PC=1,2-dipalmitoyl-sn-glycero-3-phosphocholine; DSPC or DC18:0PC=1,2-distearoyl-sn-glycero-3-phosphocholine; DAPC or DC20:0PC=1,2diarachidoyl-sn-glycero-3-phosphocholine; DBPC or DC22:0PC=1,2-dibehenoyl-sn-glycero-3-phosphocholine; DC14:1PC=1,2-dimyristoleoyl-sn-glycero-3-phosphocholine; DC16:1PC=1,2-dipalmitoleoyl-sn-glycero-3-phosphocholine; DC20: 1PC=1,2-dieicosenoyl-sn-glycero-3-phosphocholine; DC22: 1PC=1,2-dierucoyl-sn-glycero-3-phosphocholine; DPPG=1,2-dipalmitoyl-sn-glycero-3-phosphoglycerol; DOPG=1,2-dioleoyl-sn-glycero-3-phosphoglycerol and combinations thereof. Additionally, lipoproteins, gangliosides, cholesterol or plant sterols can be used to make, or are a part of, liposomes.

Some examples of lipid-polymer conjugates and liposomes are disclosed in U.S. Pat. No. 5,631,018, which is incorporated herein by reference in its entirety. Examples of processes to make multilamellar and unilamellar liposomes are known in the art (see e.g. U.S. Pat. Nos. 4,522,803, 4,310,506, 4,235,871, 4,224,179, 4,078,052, 4,394,372, 4,308,166, 4,485,054 and 4,508,703).

Extracellular Vesicles

In embodiments of the methods provided herein, the particles can be extracellular vesicles (EVs). The term "extracellular vesicles," as used herein, can include membrane vesicles secreted from cell surfaces (ectosomes), internal stores (exosomes), cancer cells (oncosomes), or released as a result of apoptosis and cell death. In addition to lipid membranes, depending on their cell or tissue of origin, EVs can include additional components such as lipoproteins, proteins, nucleic acids, phospholipids, amphipathic lipids, gangliosides and other particles contained within the lipid membrane or encapsulated by the EVs.

All cells likely release EVs, making them attractive clinical diagnostic and therapeutic targets for a range of diseases. Non-limiting examples of normal or cancer cell types that can release EVs include liver cells (e.g., hepatocytes), lung cells, spleen cells, pancreas cells, colon cells, skin cells, bladder cells, eye cells, brain cells, esophagus cells, cells of the head, cells of the neck, cells of the ovary, cells of the testes, prostate cells, placenta cells, epithelial cells, endothelial cells, adipocyte cells, kidney cells, heart cells, muscle cells, blood cells (e.g., white blood cells, platelets), the like and combinations of the foregoing. Because EVs are involved in cell-cell communication, their characterization casts light upon their role in normal physiology and pathology. EVs in biological fluids including saliva, urine and sera are being interrogated as biomarkers of ovarian, lung, bladder and prostate cancers.

Glioblastoma is the most common form of primary brain cancer and is one of the deadliest of human cancers. Glioblastoma cells release extracellular vesicles (EVs) containing amplified and mutated genetic materials derived from the tumor. The circulating EVs significantly exceed tumor-derived circulating tumor cells and tumor derived circulating DNA and RNA. The released EVs appear in the local environment, the sera and cerebrospinal fluid (CSF). Amplification of EGFR is the most frequent genetic abnormality associated with GBM, and EGFR overexpression has been shown in up to 40% of cases. GBM also often expresses EGFRvIII, a genomic deletion variant of EGFR that is constitutively active and oncogenic. Thus, the analyses of GBM EVs offer a potential tool for monitoring tumor presence, phenotypic/genotypic features, and pathophysiology.

EVs are abundant in various biological fluids, including blood, urine, and cerebrospinal fluid, but because they are released by different mechanisms and by many different cells types, EVs in biofluids can be heterogeneous. While multispectral optical methods can detect vesicles that have different molecular markers, the small average size of EVs can result in small optical signals from labels bound to or otherwise associated with these small particles, making it a challenge to analyze the EVs by optical methods.

EVs can be released by all normal and cancer cells. With a mean diameter of ~100-200 nm, however, individual EVs have ~1/10,000 the surface area and ~1/1,000,000 the volume of a whole cell, making them difficult to detect using available single cell analysis tools, including conventional flow cytometry. As a result, most proteomic and genomic analysis is performed in bulk on thousands or millions of EVs. However, EVs in biofluids come from many different cell types, and from different locations from within the cell (exosomes secreted from intracellular multi-vesicular bodies, ectosomes/microvesicles shed from the plasma membrane surface, membrane fragments released as a result of cell apoptosis, necrosis, etc). Thus, in a bulk analysis, the signature from tumor EVs may be lost in the background of vesicles from other sources. Single EV measurement approaches such as nanoparticle tracking analysis (NTA) and resistive pulse sensing (RPS) can report particle concentrations, but provide no information on the cell of origin. Thus, provided herein are methods of analyzing EV particles wherein the EV particles are characterized for their size, quantity, number of associated specific molecular markers and/or cell/tissue of origin.

The size of the particles (e.g., inert particles, liposomes or EVs) analyzed according to the methods provided herein can include particles in the size range (average length, width or diameter) of about or at 10 nm to about or at 5 microns, but generally are in the range of about or at 50 nm to about or at 100, 125, 150, 175, 200, 250, 300, 350, 400, 450, 500, 550, 600, 650, 700, 750, 800, 850, 900 or 950 nm or 1.0 to 1.5, 2.0, 2.5, 3.0, 3.5, 4.0, 4.5 or 5.0 microns.

Optically Detectable Labels and Detection Methods
Optically Detectable Labels

Any method that can detect and analyze optically detectable labels can be used in the methods provided herein. Exemplary optically detectable labels can include, for example, chromophores, chemiluminescent moieties, bioluminescent moieties, fluorescent moieties and metals. Such labels can be detected, for example, by visual inspection, by spectroscopy, by fluorescence spectroscopy, by fluorescence imaging (e.g., using a fluorescent microscope or fluorescence stereomicroscope), by flow cytometry and the like.

Exemplary chromophores include, but are not limited to, 3,3'-diaminobenzidine (DAB); 3-amino-9-ethyl carbazole (AEC); Fast Red; FD&C Yellow 5 (Tartrazine); Malachite Green Carbinol hydrochloride; Crocein Scarlet 7B (Dark Red); Erloglaucine (Dark Blue); Crystal Violet (Dark Purple); Bromophenol Blue; Cobalt(II) Chloride Hexahydrate (Red); Basic Violet 3; Acid Blue 9; Acid Red 71; FD&C Blue 1 (Brilliant Blue FCF); FD&C Red 3 (Erythrozine); and FD&C Red 40 (Allura Red AC). Exemplary fluorophores include, but are not limited to, di-8-ANEPPS, di-4-ANEPPS, a carbocyanine dye (e.g., DiO, DiL), a PKH dye (exemplary of which are PKH-26 and PKH-67), Dylight488, Brilliant Violet, Pacific Blue, Chrome Orange, Brilliant Blue 515, phycoerythrin (PE), rhodamine, fluorescein, FITC, PE-Cy5.5, PE-Cy7, APC, Alexa647, APC-Alexa700 and APC-Alexa750, Oregon Green®, derivatives of rhodamine (e.g., Texas Red and tetrarhodimine isothiocynate (TRITC)), AMCA, Alexa Fluor®, Li-COR®, CyDyes® or DyLight® Fluors); tdTomato, mCherry, mPlum, Neptune, TagRFP, mKate2, TurboRFP and TurboFP635 (Katushka). The fluorescent reagent can be chosen based on desired excitation and emission spectra. Also exemplary of fluorescent reagents are macromolecules that emit an optically detectable signal, including fluorescent proteins, such as a green fluorescent protein (GFP) or a red fluorescent protein (RFP). A variety of DNA sequences encoding proteins that can emit a detectable signal or that can catalyze a detectable reaction, such as luminescent or fluorescent proteins, are known and can be used in the methods provided herein. Exemplary genes encoding light-emitting proteins include, for example, genes from bacterial luciferase from *Vibrio harveyi* (Belas et al., (1982) *Science* 218:791-793), bacterial luciferase from *Vibrio fischerii* (Foran and Brown, (1988) *Nucleic acids Res.* 16:177), firefly luciferase (de Wet et al., (1987) *Mol. Cell. Biol.* 7:725-737), aequorin from *Aequorea victoria* (Prasher et al., (1987) *Biochem.* 26:1326-1332), *Renilla* luciferase from *Renilla renformis* (Lorenz et al, (1991) *Proc Natl Acad Sci USA* 88:4438-4442) and green fluorescent protein from *Aequorea victoria* (Prasher et al., (1987) *Gene* 111:229-233). The luxA and luxB genes of bacterial luciferase can be fused to produce the fusion gene (Fab$_2$), which can be expressed to produce a fully functional luciferase protein (Escher et al., (1989) *PNAS* 86: 6528-6532).

In embodiments, the optically detectable label can be conjugated to a molecule (e.g., a protein, an antibody, a lectin, a peptide, a nucleic acid, a carbohydrate, a glycan and the like) that binds to or otherwise associates with a molecular marker on the particle, or associates with/intercalates into the particle membrane (e.g., when the particle is a vesicle, liposome or EV).

In some embodiments, the particles can be analyzed by Raman flow cytometry using Surface Enhanced Raman Scattering (SERS) from metal nanoparticles (Nolan et al., Methods, 57:272-279 (2012).

Flow Cytometry

In embodiments of the methods provided herein, the particles are analyzed by flow cytometry. Any conventional flow cytometer, including a spectral flow cytometer, a hyperspectral flow cytometer, or an imaging flow cytometer can be used in the methods provided herein. In certain embodiments, the flow cytometry analysis is fluorescence-based rather than light scatter-based. Without being bound by theory, it is believed that when the particles are nanoparticles, e.g., of a size that is less than 1 micron or about 900 nm, 800 nm, 700 nm, 650 nm, 600 nm, 550 nm, 500 nm, 450 nm, 400 nm, 350 nm, 300 nm, 250 nm, 200 nm, 190 nm, 180 nm, 170 nm, 160 nm, 150 nm, 140 nm, 130 nm, 120 nm, 110 nm, 100 nm, 90 nm, 85 nm, 80 nm, 75 nm, 70 nm, 65 nm, 60 nm, 55 nm, 50 nm or less in diameter, light scatter based detection is not as sensitive due to the small size of the particles. In addition, more than one particle can be detected simultaneously ("coincidence"), leading to errors in determining particle size and/or count (concentration).

Fluorescence-based flow cytometry can be useful, for example, in the analysis of nanoparticles. For example, extracellular vesicles (EVs) often are in a size range of between about 100-200 nm, or about 500 nm or less. The analysis of such nanoparticles by fluorescence based flow cytometry, according to the methods provided herein, can quantitatively determine the size of the nanoparticles by stoichiometric staining of the surface area using a fluorescent surface area probe or volume probe, whereby the fluorescent intensity is proportional to the surface area or volume, respectively. In addition, fluorescence-based flow cytometry permits the sensitive detection of the number and type of molecular markers, such as surface antigens, on the nanoparticles, such as EVs, thereby providing information regarding the tissues/cells from which they originate, as well as whether the tissues/cells are cancerous (based on the number of EVs, number of molecules of molecular marker and/or type of molecular markers detected on the EVs).

Exemplary flow cytometers that can be used in the methods provided herein, in addition to any conventional flow cytometer, can include flow cytometers that employ slow flow or signal integration times to allow sufficient time to register the fluorescence intensities of nanoparticles, which are dimmer than microparticles. In some embodiments, the signal integration time of the flow cytometer is between about 0.5 μsec-5000 μsec; about 1 μsec-4000 μsec; about 5 μsec-3000 μsec; about 10 μsec-2000 μsec; about 10 μsec-1000 μsec; about 15 μsec-500 μsec; about 15 μsec-100 μsec; or about 20 μsec-50 μsec. In embodiments, the flow cytometer can have a high laser power and high numerical aperture collection optics for improved sensitivity. For example, in embodiments, the flow cytometer can have a fluorescence resolution (R) of about 10 molecules FITC to about 20, 30, 40, 50, 60, 70, 80, 90, 100, 150, 200, 250, 300, 350, 400, 450 or 500 molecules of FITC, as measured in units of mean equivalent soluble fluorochromes (MESF).

In particular embodiments, the flow cytometer used in the methods provided herein can include instruments such as those described, for example, in Zhu et al., ACS Nano 8:10998-11006 (2014) and Zhang et al., Analytical Chemistry, 84:6421-6428 (2012). Exemplary commercial flow cytometers for use in the methods provided herein include, for example, FACSCalibur (BD Biosciences) and CytoFlex (Beckman Coulter/Danaher Corporation). In embodiments, the sample flow rate setting of the flow cytometer can be the "Low" setting as designated in the instrument. In certain embodiments, the sample flow rate setting can be "Medium" or "High," as designated in the flow cytometer instrument.

An exemplary imaging flow cytometer for use in the methods provided herein is the ImageStream imaging flow cytometer from Amnis.

Detection and Analysis

In particular embodiments of the methods provided herein, a sample containing particles that are membrane vesicles (e.g., liposomes, extracellular vesicles) can be adjusted to a concentration suitable for optimal staining with the optically detectable label (surface area probe, such as di-8-ANEPPS, or molecular marker-specific probe, such as fluorescently labeled annexin V, cholera toxin B subunit or anti-CD61). For example, for a fixed concentration of the optically detectable label, the sample can be serially diluted whereby a final particle concentration of between about $1\text{-}5 \times 10^8$ to about $1\text{-}5 \times 10^{10}$ particles/μL (an average of about $1\text{-}5 \times 10^9$ particles/μL) is obtained. The serial dilution of the sample can be from about 2-fold to about 100,000-fold or more, depending on the sample. For example, when the sample is plasma, the dilution to reach a desired staining optimum is high, about 100-fold to about 10,000-fold, generally about 200-fold, due to the presence of interfering proteins in the plasma that bind to the label (e.g., the fluorescent label di-8-ANEPPS). When the sample is cerebrospinal fluid (CSF), urine or saliva, the dilution factor is less, about 5-fold to about 100-fold, generally about 20-fold, due to lower amounts of interfering protein in these samples.

The samples are diluted in an isotonic buffer, such as PBS or Hanks Balanced Salt Solution (HBSS) and a small amount of surfactant (between about 0.005% to about 0.1%, in some embodiments about 0.01%) is added to facilitate incorporation of the surface area probe into the particle. In embodiments, the surfactant is a poloxamer and in some embodiments, the poloxamer is Pluronic-127.

In embodiments of the method, a surface area probe or volume probe is used to analyze the particles. The surface area probe or volume probe is added at a concentration, generally between about 1 nM to 1 pM, that achieves stoichiometric staining of the particle surface area or volume, respectively, and provides a measurable optical signal that is proportional to the surface area or volume, respectively. For example, when the surface area probe is di-8-ANEPPS, the concentration of added probe is about 500 nM.

In some embodiments of the method, a molecular marker-specific probe is used to analyze the particles. The molecular marker-specific probe can be any ligand that can bind to or otherwise associate with a molecular marker on the particle and includes an optically detectable label. Ligands for exemplary molecular marker-specific probes can include, but are not limited to, proteins, antibodies, lectins, peptides, nucleic acids, carbohydrates or glycans that include an optically detectable label, such as a fluorophore, a fluorescent protein, a fluorescent polymer, a tandem conjugate of a first fluorophore and a second fluorophore, or an epitope, antigen or other moiety that can bind or otherwise associate with a second ligand that can be labeled with an optically detectable label.

The molecular marker-specific probe is added at a concentration, generally between about 1 pM to 100 pM, to produce stoichiometric binding or association with the molecular markers, whereby the optical signal is proportional to the number of molecular markers per particle. For example, when the molecular marker-specific probe is fluorescently labeled annexin V, the concentration of added probe is about 25-100 nM.

In embodiments of the method, more than one probe selected from a surface area probe, a volume probe or a molecular marker-specific probe can be added to the particles for analysis.

Staining of the particles with the probes is performed for an amount of time and at a temperature suitable for effective labeling and can be at ambient temperature (20-25° C.) or any suitable temperature above the phase transition of the particle being detected. The incubation time can be from about 30 seconds to about 1 minute, 2 minutes, 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours or longer, depending on the particles and the optically detectable labels. For example, when the sample is plasma and the labels are di-8-ANEPPS (surface area probe) and fluorescently labeled annexin V (molecular marker-specific probe), the incubation is for 1 hour at ambient temperature.

After staining, the sample is diluted to reduce background signals from free label and adjust the concentration of label-associated/bound particles for optimal measurement and analysis of the signal from the bound/associated label. For example, a plasma sample stained with 500 nM di-8-ANEPPS and 50 nM fluorescently labeled annexin V is diluted 1000-fold, prior to detection of the labels.

The stained particles are illuminated at a wavelength suitable for detection of the surface area/volume probe and/or the molecular marker-specific probe that is bound to or otherwise associated with the particles. In exemplary settings, when the particle analysis is by flow cytometry and the optically detectable labels are di-8-ANEPPS and fluorescently labeled annexin V, a 160 mW, 488 nm laser is used to illuminate the particles. Exemplary wavelengths can include any suitable wavelength for detecting an optically detectable label. Exemplary wavelengths for fluorescent surface area probes or volume probes are, e.g., 457 nm, 472 nm, 488 nm, 492 nm (di-8-ANEPPS) and for fluorescent molecular marker-specific probes are, e.g., 365 nm, 375 nm, 405 nm, 457 nm, 472 nm, 488 nm, 492 nm, 514 nm, 532 nm, 561 nm, 633 nm, 635-642 nm, 660 nm, 785 nm, 800 nm, 1064 nm.

The signals from the particle-associated optically detectable labels can be detected using any detector suitable for effective detection of the signals. Exemplary optical elements for selecting and dispersing light can include, but are not limited to, band pass filters, dichroic mirrors or optical gratings for filtering or dispersing light onto a detector. Exemplary detectors can include, but are not limited to, a photomultiplier tube (PMT), an avalanche photodiode, an avalanche photodiode array, a silicon-PMT, a hybrid PMT, a photodiode array, a charged cathode device (CCD), an electron multiplied CCD, a CMOS sensor detector, or any suitable photodetector. In exemplary settings for a flow cytometer, a 600 nm long pass filter and PMT can be used to detect di-8-ANEPPS and a 525/30 band pass filter and PMT can be used to detect fluorescently labeled annexin V.

In embodiments, when the analysis is by flow cytometry, the signal integration times are adjusted according to the brightness (signal intensity from the particle-associated optically detectable label) of the particles being analyzed and the type of flow cytometer used to perform the analysis. For example, when the particles are small, e.g., nanoparticles, fewer numbers of fluorescent labels becomes associated with the particles, thereby producing dimmer particles. To maximize detection of fluorescent intensity in the measurement volume, signal integration times are extended for smaller particles. In some embodiments, the signal integration time of the flow cytometer is between about 0.5 μsec-5000 μsec; about 500 μsec-5000 μsec; about 1 μsec-4000 μsec; about 5 μsec-3000 μsec; about 10 μsec-2000 μsec; about 10 μsec-1000 μsec; about 15 μsec-500 μsec; about 15 μsec-100 μsec; about 20 μsec-50 μsec; or about 10, 15, 20, 25, 30, 35, 40, 45 or 50 μsec. In an exemplary embodiment, when the sample is plasma, the signal integration time is about 20 μsec.

An "optical standard particle," as used herein, is a particle that can be used as a calibration standard in the optical methods provided herein, for determining characteristics such as the size (e.g., diameter) and/or surface area/volume and/or quantity of particles for which these characteristics are heretofore unknown (and one or more of these characteristics are known for the optical standard particle). For example, an optical standard particle of known size, or a preparation of optical standard particles of a known distribution of sizes (the sizes having been determined by a method not involving use of the optically detectable label, e.g., NTA, TRPS, EM) can be used to calibrate optical intensity in terms of surface area. For example, the diameters of the optical standard particles can be determined using NTA, and the equivalent surface area distribution calculated from the diameters. The optical standard particles can then be labeled with a surface area probe or volume probe and the signal intensities of the probe associated with the particles can be measured and plotted against the surface areas of the particles, thereby obtaining a correlation between optical intensity and surface area or volume, respectively, that can be used to determine the surface area or volume, based on measured optical intensity, of a particle of unknown size.

For calibrating optical intensity in terms of numbers of molecules of molecular markers on the particles, an optical standard particle having a known number of molecular marker molecules can be used, or a preparation of optical standard particles having a distribution of different known numbers of molecular marker molecules associated with the particles can be used. The numbers of molecular marker molecules on the optical standard particles can be determined by labeling the particles with molecular marker-specific probe, then calibrating their intensity against an external standard. For example, if the optical intensity is fluorescence intensity, the external standard can be the fluorophore FITC (fluorescein isothiocyanate) or PE (phycoerythrin) and the intensity is expressed as mean equivalent soluble fluorochromes (MESF). A correlation between MESF values and the fluorescence intensity values of the molecular marker-specific probes associated with the optical standard values can be obtained, and the number of probe molecules/particle determined from the corresponding MESF values. The molecular marker concentration can be determined by dividing the value of probe molecules/particle by the particle surface area.

An optical standard particle, as used herein, also can be a lipid-containing particle including, but not limited to, a liposome, EV or other lipid-containing vesicle, containing a known amount of lipid. Such particles can be stained in one or more known amounts using one or more known amounts of probe, thereby obtaining one or more staining solutions containing optical standard particles associated with probe at one or more known probe to lipid ratios. These staining solutions containing optical standard particles stained at known probe to lipid ratios can then be used, for example, to obtain a correlation between the values of the ratios and the detection of a spectral shift, as determined by a change in optical wavelength at which the maximum optical intensity of the stained optical standard particles is detected, or as determined by the ratio of optical intensities at two optical wavelengths. A probe to lipid ratio at which a spectral shift is detected, or a change in ratio of optical intensities is determined, is identified as a probe to lipid ratio that approaches or is at saturation. The probe to lipid ratio of the optical standard particle that is identified as a probe to lipid ratio that approaches or is at saturation can be used to determine the amount of probe to be added to the sample containing particles to be analyzed, whereby the resulting probe to lipid ratio of the particles to be analyzed approaches or is at saturation. The correlation can be predetermined, or the sample containing particles to be analyzed can be spiked with one or more known amounts of the optical standard particle to determine the amount of probe that results in a probe to lipid ratio that approaches or is at saturation.

EXAMPLES

The examples set forth below illustrate certain embodiments and do not limit the technology. Certain examples set forth below utilize standard recombinant DNA, membrane vesicle/liposome preparation and other biotechnology protocols known in the art.

Example 1: Materials and Methods

This example describes the materials and procedures used in exemplary embodiments of the methods as demonstrated herein.

1. Materials

All lipids, including: L-α-phosphatidylcholine (Egg, Chicken) [PC]; L-α-phosphatidylethanolamine (Egg, Chicken) [PE]; GM1 ganglioside (Brain, Ovine-Ammonium Salt) [GM1]; L-α-phosphatidylserine (Brain, Porcine) (sodium salt) [PS]; Sphingomyelin (Brain, Porcine); Cholesterol (Ovine, wool >98%); 1,2-dipalmitoyl-sn-glycero-3-phosphoethanolamine-N-(biotinyl) (sodium salt) [PE-b]; and 1-palmitoyl-2-(dipyrromethaneboron difluoride)undecanoyl-sn-glycero-3-phosphocholine [Top Fluor PC] were purchased from Avanti Polar Lipids. Di-8-ANEPPS (4-[2-[6-(Dioctylamino)-2-naphthalenyl]ethenyl]-1-(3-sulfopropyl)-pyridinium) was from Biotium; DiOC6(3) iodide (3,3'-Dihexyloxacarbocyanine iodide) and PKH67 were from Sigma. Nile Red fluorescent beads (0.53 μm and 0.11 μm) were from Spherotech.

Recombinant Annexin V and hamster anti-ratCD61 (clone 2C9.G2, BioLegend) were labeled with Dylight488-succinimidyl ester (Pierce) and the F/P ratios determined following the manufacturer's instructions. PPAK (D-Phe-L-Pro-L-Arg-chloromethyl ketone) was from Haematologic Technologies Inc. Phosphate buffered saline (PBS) without $Ca^{++}$ and $Mg^{++}$ was from Corning. All other reagents were from Sigma-Aldrich. Glass tubes were from Fisher and microfuge tube were from Axygen. All buffers, diluents, and sheath fluid was filtered through a 0.1 um pore diameter filter (Pall Corporation) before use.

2. Preparation of Liposomes

Lipids were dissolved in chloroform at concentrations varying between 2.5-100 mg/ml. The composition (mole percent) of lipid vesicles was 47.9% PC, 16% PE, 15% sphingomyelin, 13% cholesterol, 6% PS, 1% GM1, and 1% PE-b. The lipids, prepared at the described molar ratio at a final amount of 10 μmoles total lipid, were added to a 12×75 mm test tube. The chloroform solvent was slowly evaporated in a fume hood under a light stream of N2 gas, until a thin lipid film remained around the bottom of the tube. The thin lipid film was then hydrated with 1 mL of 0.1 μm filtered PBS (no $Ca^{++}$, $Mg^{++}$) buffer and vortexed vigorously. The resulting multi-lamellar vesicles (MLVs) were subjected to three freeze/thaw cycles alternating between an ethanol bath on dry ice and a 40° C. warm water bath. Following the freeze/thaw cycles the solution was incubated for an additional 60 minutes, with vortexing every 15 minutes. MLVs were aliquoted into 100 μL volumes and stored at −20° C. To prepare unilamellar vesicles, an aliquot of MLVs, prepared as described above, was diluted ten-fold in 0.1 μm filtered PBS (no Ca++, Mg++) to a total lipid concentration of 1 mM in preparation for extrusion to unilamellar liposomes. MLVs were extruded through a LipsoFast extrusion device (Avestin) fitted with Nucleopore polycarbonate filter membrane with average pore diameters of 0.4 μm, 0.2 μm, 0.1 μm, 0.08 μm, and 0.05 μm (GE Water & Process Technology) for a total of 21 passes (an odd number so as to minimize contamination with un-extruded particles in final syringe). Liposomes were collected in 1.5 mL microfuge tubes, aliquoted, and stored for up to several weeks at 4° C.

3. Cell-Free Plasma Supernatants Containing Extracellular Vesicles (EVs)

Female Sprague Dawley rats (11 weeks of age) were obtained from Charles River Laboratories (Wilmington, Mass.) and cared for in accordance with the Guide for the Care and Use of Laboratory Animals, 8th Edition (26). All animals were determined to be pathogen free by Charles River Laboratories assessment plus profile testing. Animals were individually housed at an AAALAC, Intl-accredited facility in non-sterile ventilated polycarbonate micro-isolator cages on corncob bedding. All research protocols were approved by Amgen Inc. (Seattle, Wash.) Institutional Animal Care and Use Committee. Animals had ad libitum access to pelleted feed (2020X Teklad; Harlan Laboratories Inc., Madison, Wis.) and water (reverse osmosis-purified) via automatic watering system. Animals were on a 12:12 hr light:dark cycle in rooms with controlled temperature and humidity and had access to enrichment opportunities (enrichment tubes and Nylabones). Blood (~400 μL) was collected into sodium citrate, and centrifuged 10 minutes at 2500×g and the supernatant collected to prepare cell-free plasma which was aliquoted and stored at −80° C.

4. Nanoparticle Tracking Analysis (NTA)

Liposomes were diluted in filtered DPBS and loaded into the chamber of a Nanosight LM-20 equipped with a 532 nm laser and a CCD (charged cathode device) camera. The optimal camera level (setting: 15) and threshold (setting: 2) were established in preliminary experiments. Five movies of 60 seconds each were recorded and analyzed for each sample using the NanoSight software. Average histograms and mean diameters are reported.

5. Flow Cytometry Instrumentation and Operation

Samples were analyzed on a FACSCalibur (BD Biosciences) equipped with stock lasers, filters, and detectors and using the "Low" sample flow rate setting. Samples also were analyzed using a flow cytometer of higher sensitivity constructed using components from commercial instruments. The constructed flow cytometer contained an optical bench (flow cell, excitation laser beam shaping optics, forward angle obscuration bar, orthogonal collection optics, and optical relay fibers) from a FACSCanto flow cytometer (BD Biosciences, San Jose, Calif.), a 488 nm laser (200 mW, Sapphire, Coherent), and a multi-PMT detector assembly from a Beckman Coulter Elite cell sorter.

Green (DyLight 488) and red (di-8-ANEPPS) fluorescence was collected through a 525/40 bandpass or a 600 LP, respectively. Sheath and sample flow was provided by continuous flow pumps (Milligat, GlobalFIA, Fox Island, Wash.) at rates of 20 µL/sec and 0.02 µL/sec respectively, which gave a transit time (pulse width) of ~20 µsec through the probe volume (about 10× longer than a conventional flow cytometer). Data was acquired with a custom data acquisition system that digitized signal pulses from the analogue detectors (PMTs and photodiodes) and recorded pulse height and area from each channel, plus pulse width from the trigger channel. Some histogram data was analyzed using the Kolmogorov-Smirnov (KS) test (27).

6. Vesicle Staining and Size Calibration

Samples (liposomes or cell-free plasma supernatants) were serially diluted into 100 µL of 0.1 µm filtered HEPES buffered saline (HBS; 150 mM NaCl, 10 mM HEPES pH 7.4) containing 500 nM di-8-ANEPPS, 0.01% Pluronic-127, 5 mM $CaCl_2$) and 20 µM PPAK in a row of a 96 well plate, stained for at least 60 minutes, then diluted 1:800 in PBS and analyzed by flow cytometry to determine the dilution of sample that gave optimal staining. For liposomes, this was at a probe to lipid ratio of at least 0.1, which was equivalent to $5 \times 10^{10}$ particles/mL (measured by NTA) in 500 nM di-8-ANEPPS. For EVs in rat plasma, high concentrations of plasma proteins that can also bind di-8-ANEPPS required the use of a higher probe to lipid ratio, achieved at a concentration of $5 \times 10^9$ nanoparticles/mL (as measured by NTA) in 500 nM Di-8-ANEPPPS. In subsequent experiments, EV preps were diluted in staining buffer as above, 50 nM of DyLight488-labeled surface marker added, and the sample stained for at least 60 minutes (determined in preliminary experiments) at ambient temperature, followed by dilution and analysis by HSFC.

To calibrate the di-8-ANEPPS fluorescence in terms of vesicle surface area, the di-8 intensity (channel number) was plotted against surface area (calculated from NTA diameter estimates, assuming sphericity) at frequency intervals of 0.1. The slope and intercept of this line was used to convert channel number to surface area ($nm^2$), and then diameter was calculated with the assumption that the vesicles are spherical.

Example 2: Fluorescence Detection Vs. Light Scatter Based Detection

Conventional flow cytometry on particles ≥1 µm generally use light scatter as a trigger parameter because the scatter intensity of such particles generally is well above background. Scatter intensity however drops off rapidly as particle size decreases and particle refractive index, collection angle, and "cleanliness" of sheath and sample buffers can have large effects on the performance of this method. The resolution by flow cytometry using fluorescence as a trigger was compared to the resolution obtained using light scatter as a trigger. Established fluorescence calibration protocols were used (Nolan J P, Stoner S A. A trigger channel threshold artifact in nanoparticle analysis, Cytometry Part A 2013; 83A:301-305; Hoffman R A, Wood J C S. Characterization of Flow Cytometer Instrument Sensitivity, Current Protocols in Cytometry: John Wley & Sons, Inc.; 2007; Schwartz A, Gaigalas A K, Wang L, Marti G E, Vogt R F, Fernandez-Repollet E. Formalization of the MESF unit of fluorescence intensity, Cytometry Part B: Clinical Cytometry 2004; 57:1-6; Chase E S, Hoffman R A. Resolution of dimly fluorescent particles: A practical measure of fluorescence sensitivity, Cytometry 1998; 33:267-279; Wood J. Fundamental flow cytometer properties governing sensitivity and resolution, Cytometry 1998; 33:260-266; Wood J, Hoffman R A. Evaluating fluorescence sensitivity on flow cytometers: an overview, Cytometry 1998; 33:256-259; Schwartz A, Fernandez Repollet E, Vogt R, Gratama J W. Standardizing flow cytometry: construction of a standardized fluorescence calibration plot using matching spectral calibrators, Cytometry 1996; 26:22-31; Schwartz A, Marti G, Poon R, Gratama J, Fernandez-Repollet E. Standardizing flow cytometry: a classification system of fluorescence standards used for flow cytometry, Cytometry 1998; 33:106-114; Wang L, Gaigalas A K, Abbasi F, Marti G E, Vogt R F, Schwartz A. Quantitating fluorescence intensity from fluorophores: practical use of MESF values. JOURNAL OF RESEARCH-NATIONAL INSTITUTE OF STANDARDS AND TECHNOLOGY 2002; 107:339-354).

A mixture of two Nile Red fluorescent beads, 0.53 µm and 0.11 µm, were analyzed by flow cytometry using either light scatter-based triggering or fluorescence-based triggering, at a concentration adjusted to minimize coincidence (simultaneous detection of more than one particle in the measurement volume, as a single count) to a negligible level ($1 \times 10^7$ particles/mL). FIG. 1 shows side scatter and fluorescence intensity histograms of the particle measurements triggered on fluorescence (A-C) vs. scatter (D-F). The trigger threshold required to minimize the background event rate threshold (dashed line) and the system background signal levels obtained using a software trigger (grey filled histogram) also are shown.

The histograms of FIG. 1 show that the 0.53 µm bead is readily detected using a side scatter trigger or a fluorescence trigger. Single beads are clearly identified on both side scatter and Nile Red fluorescence channels, as are coincident events, which are approximately twice as bright. However, the light scatter from the 0.11 µm bead is much lower and as the trigger threshold is lowered, triggered events from particles in the sheath and sample fluids begin to dominate the histogram, even before the optical background of the system as determined by a software trigger is reached. By contrast, setting the fluorescence trigger threshold just above the software trigger background allows the dim (0.11 µm) fluorescent beads to be detected, while their light scatter is in background range. The population of 0.11 µm beads could be resolved about background in the fluorescence channel (see, e.g., panels B and C), but in the side scatter channel were poorly resolved from noise and below the threshold required for side scatter triggering (see, e.g., panels E and F)

The results show that in this system, with sheath and sample fluid consisting of 0.1 µm filtered nanopure water, fluorescence triggering provides superior resolution. Thus, fluorescence triggering was expected to be even more significant as a tool for the study of lipid membrane vesicles, whose refractive index is significantly lower than the polystyrene Nile Red beads studied in this example and, as a consequence, are expected to scatter less light.

Example 3: Vesicle Staining Using Surface Area Probes

Several lipophilic fluorescent probes were evaluated for their ability to stain membrane vesicles as surface area probes. Surface area probes were assessed for their ability to bind saturably and stoichiometrically with membrane vesicles such that probe-associated fluorescence is proportional to surface area and the fluorescence is enhancement when bound to membrane relative to when the probe is free in solution.

Three blue-excited membrane surface area probes, DiO, PKH67, and di-8-ANEPPS, were evaluated for their suitability in staining lipid vesicles for analysis by flow cytometry. Absorbance and fluorescence emission spectra of each probe were obtained in PBS and in PBS containing 100 nm diameter liposomes. All three probes exhibited an increase in fluorescence upon addition of lipid membrane, with Di-8-ANEPSS having the lowest fluorescence in aqueous buffer and the greatest enhancement in the presence of lipid membrane.

The suitability of these probes for detecting liposomes was evaluated using flow cytometry. Different dilutions of a liposome stock solution were stained using a fixed concentration of probe (100 nM) to give different probe/lipid ratios (P/L) and measured using the custom flow cytometer set for triggering on fluorescence. For all probes, both the number of events per uL of liposome stock solution and the event brightness varied for P/L ratios >0.1. However, for di-8-ANEPPS, both the liposome concentration estimates and the liposome brightness were consistent for P/L >0.1 and up to a P/L of 0.25, indicating that the di-8-ANEPPS staining intensity of liposomes is saturable over this P/L range.

To confirm that single vesicles and not coincident vesicles were being measured (coincidence often is a problem when attempting to measure very dim small particles), a series of two fold dilutions of di-8-ANEPPS-stained liposomes was performed, and it was found that the measured event rate decreased in proportion to the dilution, but the median fluorescence did not change, consistent with the analysis of single particles. The liposome concentration measured by flow cytometry, after accounting for dilutions ($6.2 \times 10^8$ particles/uL), was within a factor of two of the concentration estimated by NTA ($12 \times 10^8$ particles/uL). To confirm that lipid vesicles were being measured, the di-8-ANEPPS-stained liposomes were treated with 0.05% Triton X-100, which solubilized the vesicles and reduced particle counts to background levels.

The extruded liposomes were found to be stable, with stored liposomes (4 months, 4° C.) retaining the same fluorescence staining properties as freshly extruded liposomes. The results demonstrate that liposomes are attractive as possible reference particles to aid in the standardization of EV measurements.

Example 4: Calibration of Vesicle Size Using NTA or Flow Cytometry

The results from Example 3 above suggested that di-8-ANEPPS intercalates into membrane vesicles in a stoichiometric manner, and thus could be useful to estimate vesicle surface area and, therefore, vesicle diameter. To evaluate this possibility, di-8-ANEPPS at a P/L ratio of >0.1 was used to measure liposomes that had been prepared by extrusion through nucleopore filters with different pore sizes. FIGS. 2A-D depict fluorescence intensity histograms of di-8-ANEPPS stained vesicles prepared by extrusion through polycarbonate membrane filters with average pore sizes of 200 nm (A), 100 nm (B), 80 nm (C) and 50 nm (D), as described in Example 1. FIGS. 2E-H depict nanoparticle diameter population histograms from NTA of the same vesicles, with the median diameter of each preparation indicated.

As shown in FIGS. 2A-D, liposomes extruded through increasingly smaller pore sizes and stained with di-8-ANEPPS showed unimodal fluorescence intensity distributions with increasingly lower intensities. For reference, these intensities ranged from ~25-1000 mean equivalent PE-TexasRed molecules (MEPETR), determined using Spherotech Rainbow beads and the manufacturer's calibration values. These same liposome preparations also were analyzed by nanoparticle tracking analysis (NTA), which estimates nanoparticle diameter from its Brownian diffusion and from which diameter can be calculated (FIGS. 2E-H, dashed lines).

To calibrate fluorescence intensity in terms of surface area, the NTA diameter measurements were converted to surface area using the assumption of sphericity, and the resulting distribution plotted against the di-8-ANEPPS intensity distribution at frequency intervals of 0.1 (FIG. 3). The slope and intercept of the line were used to convert di-8-ANEPPS intensity into surface area units, and then to diameter units (FIGS. 2E-H, solid lines). For vesicles ~120 nm and smaller, there was excellent concordance between the fluorescence intensity measurements and NTA. For larger vesicles (larger than ~200 nm), flow cytometry using a fluorogenic membrane surface area probe was found to detect the vesicles more efficiently when compared to NTA.

The light scatter intensity of the events detected using fluorescence triggering also was recorded; it was found that light scatter from low refractive index membrane vesicles was below the detection limit of the flow cytometer instrument. Light scatter measurements also are sensitive to the presence of non-fluorescent particles in the sample and sheath fluids and even when particles can be detected, calibration of these measurements is difficult. Thus, the results demonstrate that fluorescence staining of vesicle membrane surface area is an attractive alternative to light scatter-based approaches for detecting and estimating the size of very small vesicles by flow cytometry.

Example 5: Analysis of Extracellular Vesicles in Plasma

To evaluate flow cytometry for EV detection, plasma from untreated rats was analyzed using the custom flow cytometer described in Example 1. Cell-free plasma was prepared from blood by low speed centrifugation ($2 \times 2500 \times g$, 10 minutes) to remove large cells and analyzed using NTA to determine total nanoparticle concentration and population size distribution. Plasma from three different rats was measured by NTA (FIGS. 4A-C) or by flow cytometry (vesicle flow cytometry or VFC; FIGS. 4D-F).

For flow cytometry, samples were diluted to approximately $1 \times 10^9$ nanoparticles per uL, stained with 100 nM di-8-ANEPPS, further diluted 1000-fold, and analyzed by flow cytometry. FIG. 4 shows NTA (4A-C) and flow cytometry (4D-F) population diameter distributions from the three representative rat plasma samples, estimated using liposomes as a reference particle as described above. Both NTA and flow cytometry reported unimodal particle populations, with a peak (mode) diameter of ~120 nm.

The correlation between NTA nanoparticle concentration estimates and flow cytometry vesicle concentration estimates for eight different animal samples are presented in FIG. 4G. NTA reported total nanoparticle concentrations in untreated rat plasma between $1.54 \times 10^7$/uL and $1.24 \times 10^9$/uL (average $4.87 \times 10^8$/uL, n=8), while flow cytometry reported total vesicle concentrations of $5.12 \times 10^7$/uL to $1.95 \times 10^8$/uL (average $1.03 \times 10^8$/uL, n=8). In general a direct correlation was found between NTA, which measures particles with detectable light scatter, and flow cytometry, which measures particles with detectable fluorescence, with NTA reporting concentrations ~3-5 fold higher than flow cytometry. This difference may be due in part to the selectivity of flow cytometry for membranous particles, as well as uncertainties in the volume of the sample measured by NTA and the limits of detection of the two methods.

To test the ability of flow cytometry to measure high abundance surface markers on EVs, platelet rich plasma (PRP) from rats were prepared and stimulated with the ionophore A23187, which is known to induce platelet EV release. After treatment, samples were centrifuged as above to remove residual cells and platelets and stained with di-8-ANEPPS as a surface area probe, followed by staining with either Dylight488-Annexin V or -CD61 as a membrane molecular marker-specific probe. CD61 is a component of the α2β3 integrin complex found in high abundance on platelets, while annexin V binds to exposed phosphatidylserine (PS) on the outer leaflet of the vesicle membrane.

FIG. 5 depicts the fluorescence measurement of EV surface markers from control plasma (5A, 5B) or ionophore-treated platelet-rich plasma (5C, 5D). As shown in FIG. 5, EVs stained with both di-8-ANEPPS and Dylight 488-Annexin V show a clearly resolved population of EVs, with annexin V binding corresponding to ~28% of total EVs with a median brightness equivalent to ~6400 MESF of fluorescein, as well as a population that was annexin V negative (FIG. 5A). Upon treatment with ionophore, >60% of the EVs were annexin V positive (FIG. 5C). Similarly, ~23% of EVs in control plasma were positive for CD61, with a median brightness equivalent to ~1500 MESF of fluorescein (FIG. 5B), which increased to ~50% CD61 positive in ionophore treated PRP (FIG. 5D). Thus, high sensitivity flow cytometry triggered on the fluorescence of a fluorogenic membrane probe allows detection of individual EVs in plasma, as well as the detection of EV sub-populations expressing cell surface markers.

Example 6: Analysis of Extracellular Vesicles in Cerebrospinal Fluid

Cerebrospinal fluid (CSF) samples from patients diagnosed with five different neurological disorders, and from normal subjects, were analyzed by NTA or by flow cytometry. For flow cytometry, CSF samples were stained using di-8-ANEPPS as a fluorescent surface area probe for the membranes of EVs in CSF, and DyLight488-labeled surface markers (annexin V or anti-CD41) were used as fluorescent molecular marker-specific probes of the EVs. The samples prepared for flow cytometry were analyzed using the custom constructed instrument described in Example 1.

Pools of patient-derived CSF samples from patients having high grade glioma, low grade glioma, Alzheimer's disease, Parkinson's disease or subarachnoid haemorrhage showed 2- to 7-fold increases in the concentration of EVs, compared to samples from normal subjects, with no notable differences in size, indicating that the EV concentrations could have diagnostic value.

Further, while the EV size distributions determined by NTA and by flow cytometry (measuring fluorescence intensity of EV-associated di-8-ANEPPS) were similar, the particle concentrations obtained by flow cytometry were lower than NTA ($2.16\times10^6$ particles/μl with flow cytometry, relative to $4.32\times10^6$ particles/μl with NTA) and the mean size was larger (192 nm with flow cytometry, relative to 118 nm with NTA), indicating that NTA likely measures all scattering particles in the CSF while flow cytometry measures membranous nanoparticles. In addition, the measured intensities of the fluorescent molecular marker-specific probes associated with the EVs revealed variable annexin V—associated EV fractions, with some showing a significant fraction of CD41—associated EVs. Thus, fluorescence measurement based flow cytometry could characterize the EVs in CSF with high sensitivity compared to NTA, with flow cytometry providing fluorescent antibody based speciation of EVs.

Example 7: Antibody-Capture Nanospheres for Compensation and Spectral Reference

Figure 6:
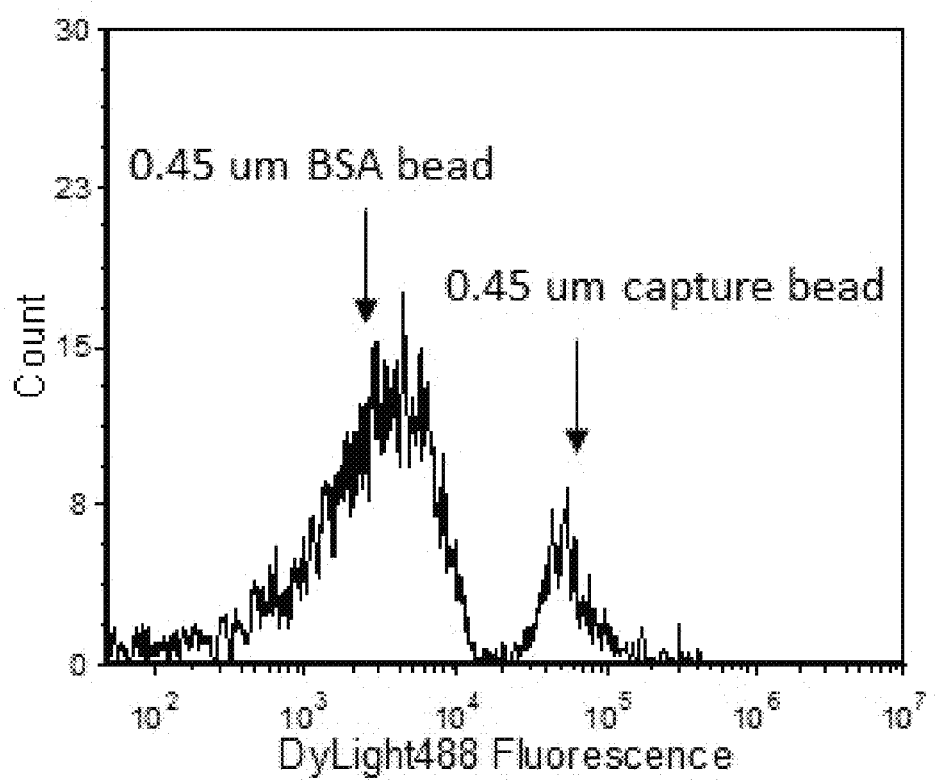
FIG. 6 depicts fluorescence staining of polystyrene antibody capture beads coated with anti-lambda IgG and stained with a DyLight 488 conjugated antibody.

A set of 0.45 um antibody capture beads that each capture about 5000 antibody molecules were developed as positive control nanobeads (optical standard particles) and BSA coated beads were developed as negative control nanobeads (optical standard particles). 450 nm polystyrene beads were coated with either anti-lambda IgG (positive control) or BSA (negative control). Such beads can serve as a spectral reference for use in compensation or spectral unmixing, to obtain a more accurate detection and/or quantitation of the fluorescence intensity of nanoparticles (e.g., EVs) of interest. FIG. 6 depicts histograms from a sample containing both the positive and negative control beads stained with a DyLight488-conjugated antibody. The results show that the antibody capture beads were selectively stained by the fluorescent antibody relative to the BSA beads, as measured by DyLight488 fluorescence, thereby demonstrating that these spectral reference beads can be added to a nanoparticle sample in known amounts to quantitate the relative numbers of molecular marker molecules associated with the nanoparticles (i.e., the molecules associated with the nanoparticles that bind to fluorescent molecular marker-specific probes).

The antibody capture beads can be used as compensation standards for flow cytometry measurements of particle, including nanoparticle, surface markers or in multispectral measurements of particle, including nanoparticle (e.g., EV) surface molecular markers by capturing antibodies labeled with multiple different fluorophores. Such a panel of antibody capture beads can provide efficient analyses of multiple nanoparticle-associated molecular markers, while serving as spectral reference particles to correct for spectral mixing between the different. The spectral data stream can have the background Rayleigh and Raman scatter spectra subtracted in real time and data can be analyzed in the conventional mode, where signals from various spectral bands are plotted as intensity histograms, or as a hyperspectral data set that allows spectral approaches that can produce higher resolution measurements.

Figure 7:
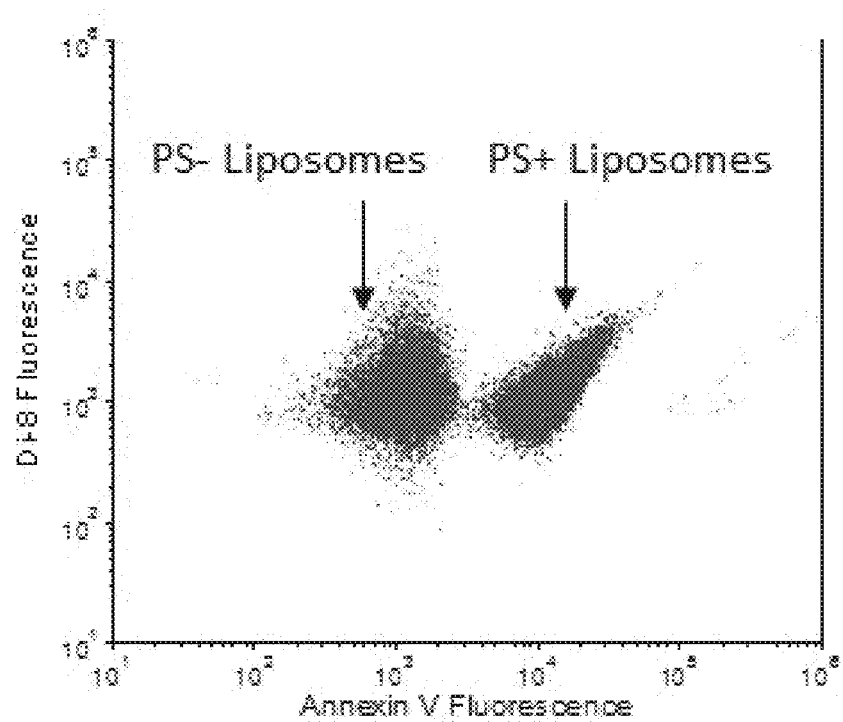
FIG. 7 depicts specific fluorescence staining of synthetic liposomes containing phosphatidylserine (PS) in a population containing a mixture of synthetic liposomes that contain or do not contain PS.

Example 8: Characterized Liposomes for Detection and/or Sizing of Vesicle-Associated Molecular Markers Liposomes, i.e., synthetic lipid vesicles, were prepared with defined compositions and nanoparticle size distributions that can be measured by independent methods (NTA, RPS, TEM), to serve as reference particles for the analysis of EVs. The liposomes were found to be stable for months at 4° C. FIG. 7 depicts flow cytometry bivariate histograms showing di-8-ANEPPS vs. Brilliant Violet-conjugated Annexin V fluorescence of liposomes with or without phosphatidylserine (PS), which binds to annexin V. The liposomes were prepared by extrusion as described in Example 1, resulting in a preparation with a mean diameter of 150 nm, as measured by NTA. While both liposome populations (PS− and PS+) show comparable di-8-ANEPPS fluorescence, the histogram shows enhanced Brilliant Violet-conjugated Annexin V fluorescence in the liposome population containing phosphatidylserine (PS+). Thus, in accordance with the methods provided herein, fluorescence flow cytometry could be used to separate distinct populations of nanoliposomes (size in the nm range), based on the presence or absence of PS as a marker.

Example 9: Supported Bilayer Lipospheres for Standardization of Membrane (Surface Area) Probes Sub-micron sized silica lipospheres bearing a supported lipid bilayer were developed for detection by light scatter or for staining by surface area probe membrane dyes such as Di-8-ANEPPS and annexin V. 500 nm silica nanospheres were coated with a lipid bilayer, generating silica lipospheres. The 500 nm silica beads (nanospheres) were obtained from Duke Scientific (#8050) and sonicated to disperse the beads. 25 µL of a stock solution of the beads ($3\times10^{11}$ bead particles/ml) was pipetted into 1 mL of 10 mM HEPES buffer pH 7.3, 150 mM NaCl. To the resulting diluted solution, 100 µM MLV stock, prepared as described in the section "Preparation of Liposomes" in Example 1 and pre-warmed to 45° C., was added. The mixture was vortexed and incubated at 45° C. for 15 minutes, then overnight at ambient temperature on a rotator. The overnight incubation can be performed at any temperature that is above the lipid phase transition temperature—for example, 20-25° C. for some particle lipid compositions, 30-37° C. for other particle lipid compositions.

The next day, the bilayer coated silica beads (nanospheres) were washed 3 times in buffered saline, followed by centrifugation. The resulting silica liposphere preparation was stored at 4° C., at a concentration of $1\times10^9$ bead particles/ml.

Figure 8:
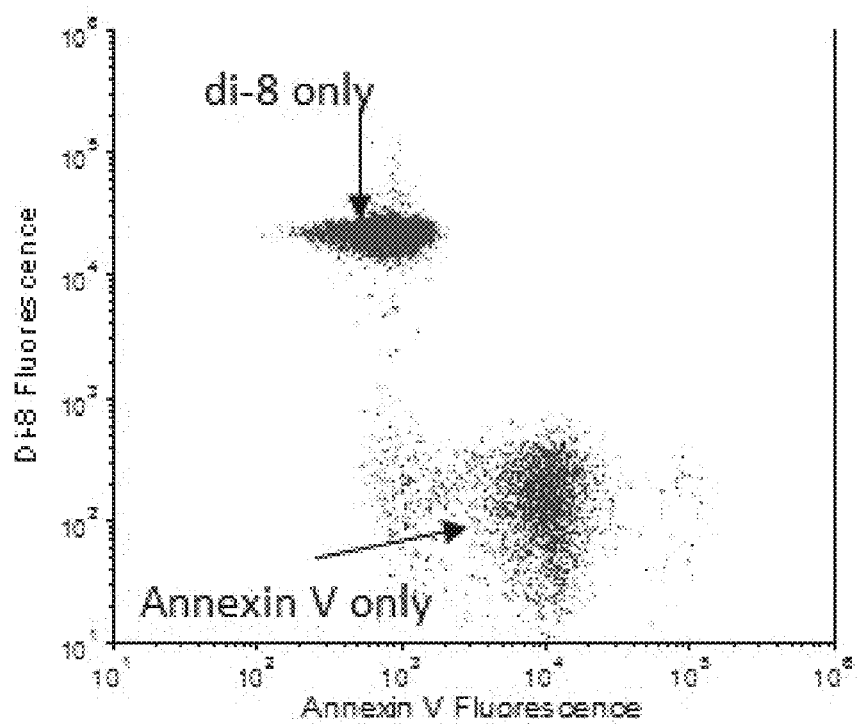
FIG. 8 shows fluorescence staining of silica spheres coated with a lipid bilayer.

The silica lipospheres can serve as both positive staining controls and spectral compensation reference particles. Presented in FIG. 8 are data from lipospheres stained with either Di-8-ANEPPS or DyLight488-annexin V and analyzed on the custom flow cytometer constructed as described in Example 1, using side scatter as a detection trigger. FIG. 8 shows two distinct liposphere populations, the population stained with di-8-ANEPPS showing enhanced di-8-ANEPPS fluorescence and the population stained with DyLight488-Annexin V showing enhanced annexin V fluorescence. The results demonstrate that both dyes are capable of binding to the lipospheres, thereby validating their use as reference particles.

Example 10: Determining Membrane Dye Saturation Using Fluorescence Spectral Shift Estimates of the concentration and size of vesicles is most accurate when the fluorescent probe labeling of the vesicle is close to or at saturation. We have observed that the fluorescence spectrum of di-8-ANEPPS associated with a vesicle undergoes a spectral shift as it approaches saturation in the vesicle membrane. Monitoring the spectral shift can be used to determine when probe saturation is reached.

Figure 9A:
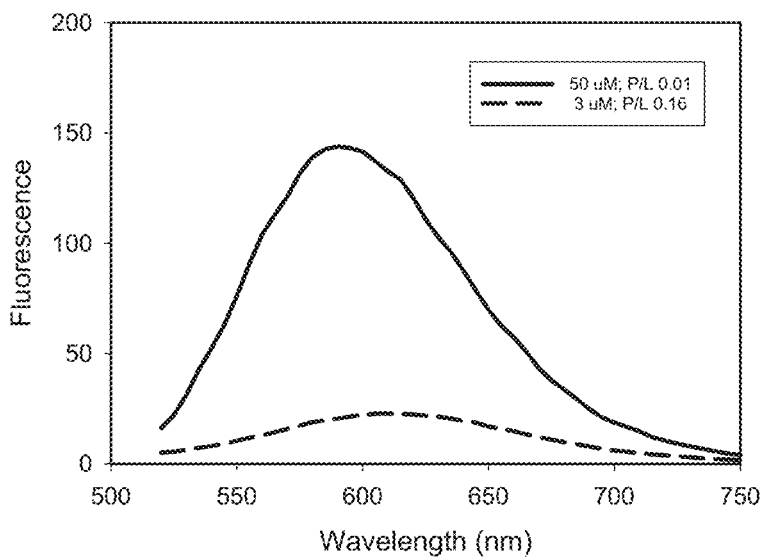
FIGS. 9A to 9F show measurement of a fluorescence spectral shift to measure saturation of a lipid-containing particle using a membrane dye.
Figure 9B:
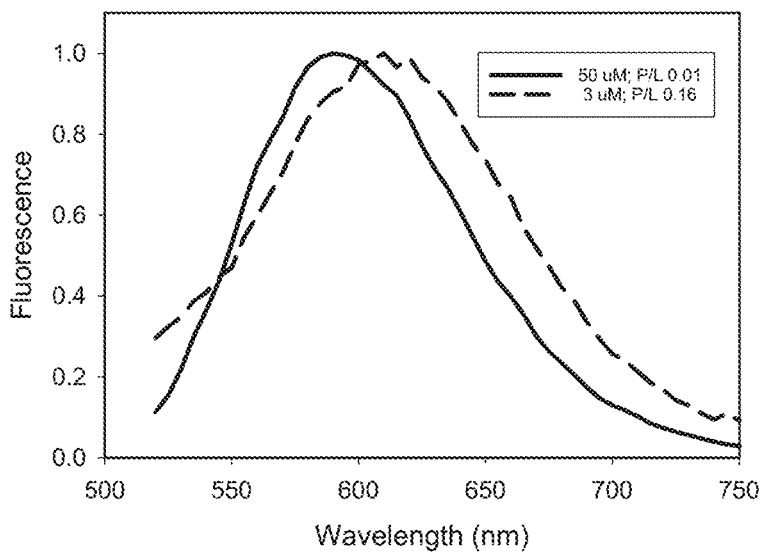
Figure 9C:
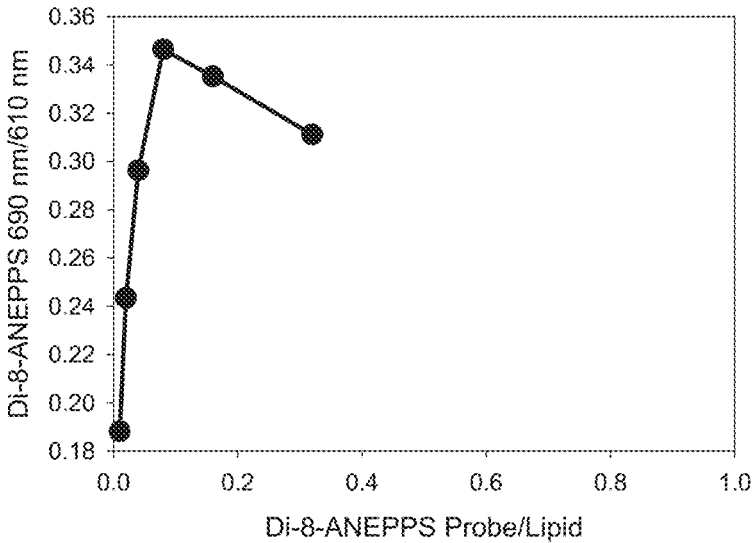

FIGS. 9A and 9B are fluorescence spectra of bulk suspensions of di-8-ANEPPS (500 nM) in buffer alone (HBS; 150 mM NaCl, 10 mM HEPES pH 7.4) or buffer plus two concentrations of synthetic lipid vesicles (50 uM and 3 uM, prepared as in Example 1 above) to produce two different probe to lipid ratios (0.01 and 0.16, respectively). At the lower vesicle concentration, the probe to lipid ratio is higher and the fluorescence emission maximum is shifted shifts towards the red. This spectral shift can be expressed as the ratio of fluorescence intensity at 690 nm to the fluorescence intensity at 610 nm, and can be used to monitor the probe as it approaches saturation in the membrane. FIG. 9B is a normalized representation of the measurements depicted in FIG. 9A. Presented in FIG. 9C is the ratio of intensities at 690 to 610 nm measured at several different probe to lipid ratios. The measurements depicted in FIGS. 9A-C were performed in a fluorimeter on bulk solutions in containers, such as cuvettes.

Figure 9D:
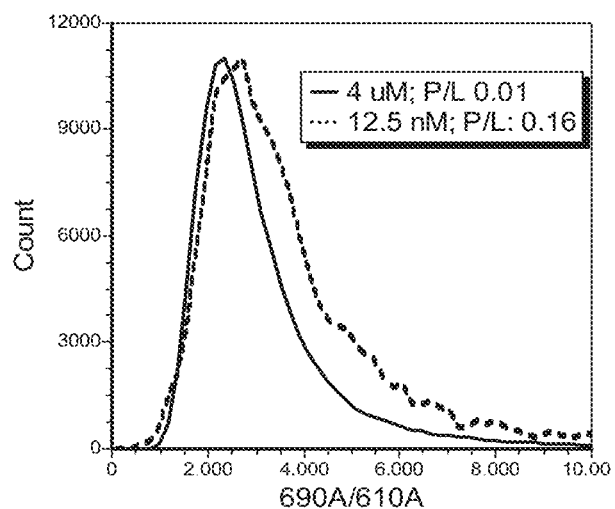
Figure 9E:
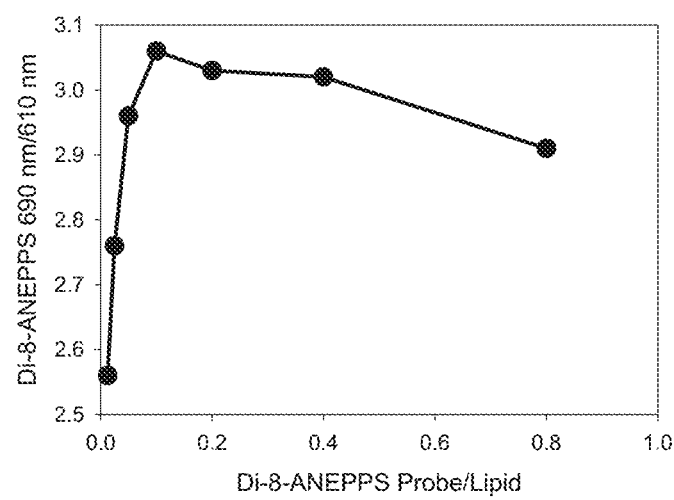

The spectral shift also can be monitored by flow cytometry, using the ratio of fluorescence intensity measured through a 690/50 nm band pass filter to the intensity measured through a 610/20 nm bandpass filter. Flow cytometry permits the analysis of individual particles/vesicles. Presented in FIG. 9D are histograms of the population distributions of the ratio of intensities of the synthetic vesicles measured through the 690/50 nm and 610/20 nm filters (690/610 ratio), for high (0.16) and low (0.01) probe to lipid ratios. The vesicles stained with the higher probe to lipid ratio have a higher 690/610 ratio, which indicates a higher degree of saturation. FIG. 9E presents the ratio of intensities at 690 to 610 nm measured by flow cytometry of synthetic vesicle preparations having several different probe to lipid ratios.

Figure 9F:
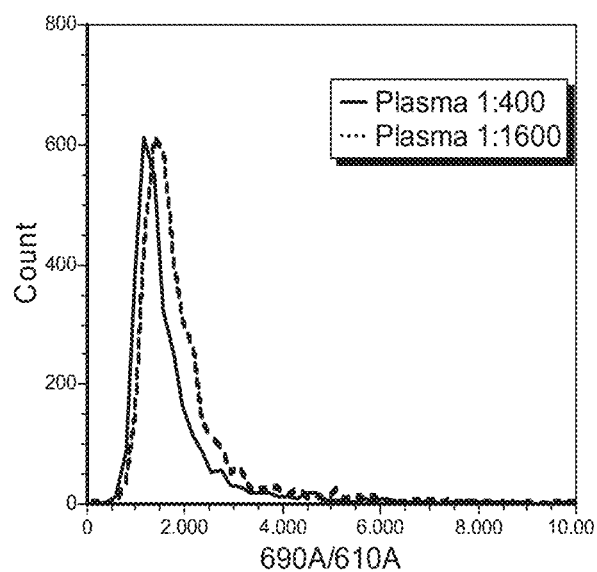

The spectral shift also was shown to occur in EVs in plasma. Serial dilutions of platelet-poor plasma (PPP) in buffer were prepared and stained with 500 nM di-8-ANEPPS, to produce samples with different probe to lipid ratios. FIG. 9F presents the median 690/610 ratio at two dilutions of human PPP. The more diluted PPP preparation (1:1600 dilution), which has a higher amount of probe relative to the plasma particles (higher P/L ratio), showed a spectral shift relative to the less diluted (more concentrated) PPP preparation, as seen by an increase in the 690/610 ratio. Thus, monitoring the 690/610 ratio provides a means to measure when probe saturation is approached in synthetic vesicle staining as well staining of biological vesicular preparations.

Example 11: Detection of Vesicles and Measurement of their Light Scatter

Flow cytometry of cells generally employs light scatter to trigger detection, and most examples of vesicle measurements by flow cytometry also use this approach, which presents a number of difficulties including, but not limited to: 1) the very dim light scatter signals produced by vesicle owing to their small size and low refractive index; 2) background light scatter from particles in sample, reagents, buffers, and sheath fluids as well as scatter from the flow cell and other optical components; 3) differentiation between the dim scatter from vesicles as discussed in 1) and the various sources of background as discussed in 2); and 4) interpreting light scatter intensity given its complex dependence on illumination wavelength, particle size (radius), and refractive index. The fluorescence-based detection approach provided herein, which uses a fluorogenic membrane probe, obviates many of these issues by selectively detecting membrane vesicles with fluorescence intensity that is proportional to vesicle size (surface area) and rendering light scatter a more useful measurement parameter.

Figure 10A:
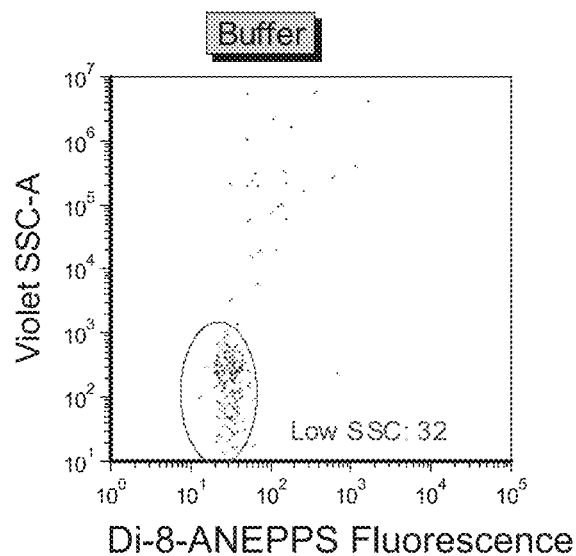
FIGS. 10A to 10E depict measurement of light scatter in samples containing vesicles, using a fluorescence-based detection approach.
Figure 10B:
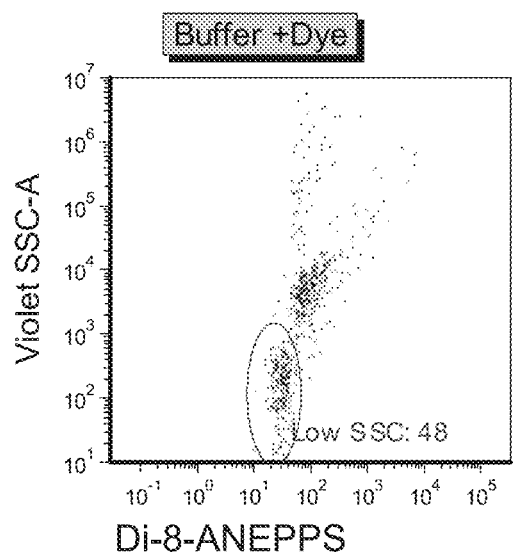
Figure 10C:
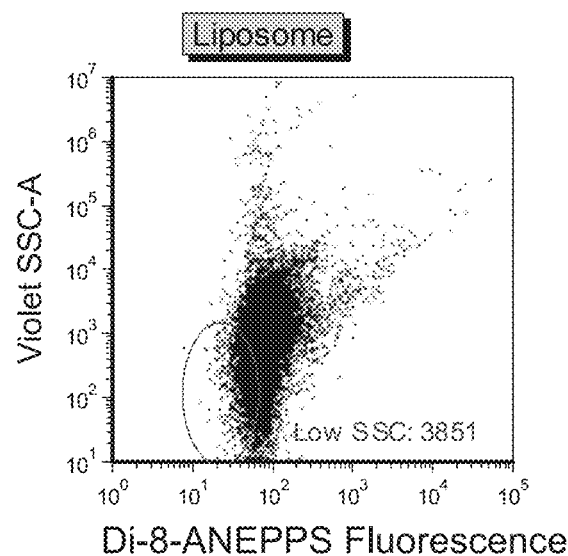
Figure 10D:
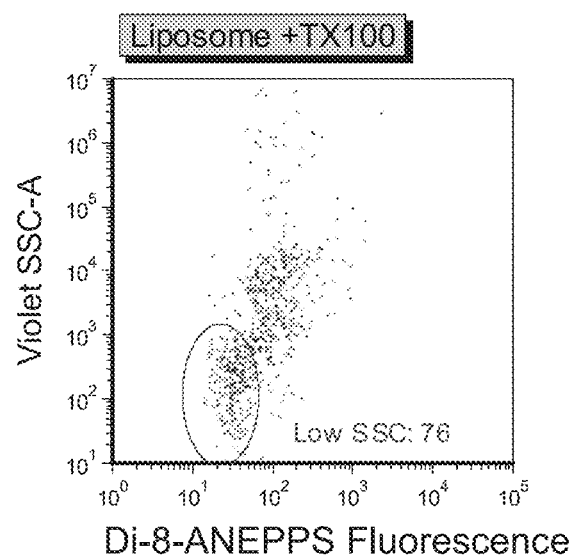

To demonstrate the effectiveness of the fluorescence-based detection approach, we analyzed the di-8-ANEPPS fluorescence and violet (405 nm) light scatter in samples of buffer only (HBS; 150 mM NaCl, 10 mM HEPES pH 7.4), buffer plus fluorogenic membrane probe, and buffer plus probe and synthetic vesicles. As presented in FIG. 10A, analysis of buffer alone only produces a small number of background events, a population of low scattering, low fluorescence events, and a population of higher scatter, higher fluorescence events. Analysis of buffer plus probe produces a similar number and type of events (FIG. 10B). Analysis of stained synthetic vesicles (liposomes) produces a distinct population of fluorescent events that have light scatter that increases with increasing fluorescence intensity and estimated diameter (FIG. 10O). When the sample of stained synthetic vesicles is treated with detergent (0.1% Triton X-100; TX1000) to disrupt the membrane vesicles, the distinct population of fluorescent events is eliminated (FIG. 10D), confirming that this population of events are detected due to the presence of membrane vesicles. Thus, the particle analysis methods provided herein can resolve membrane vesicles.

Figure 10E:
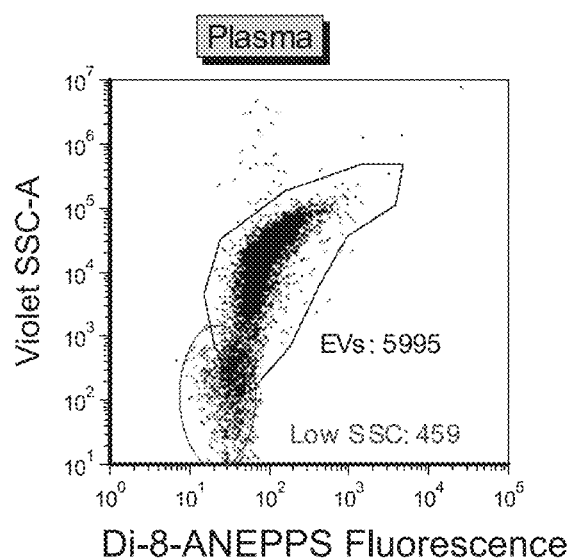
Figure 10F:
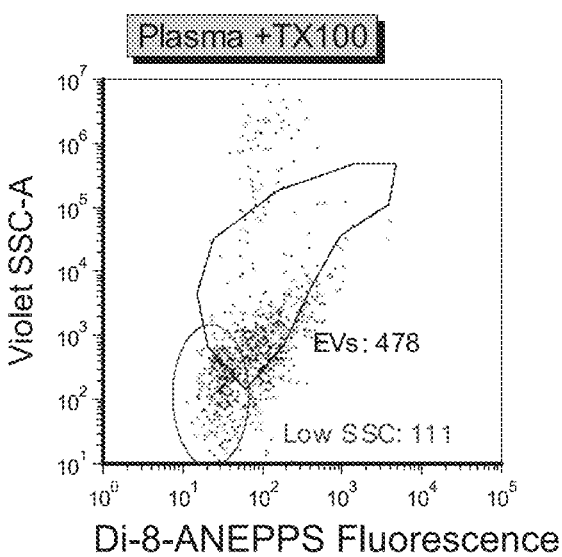
FIG. 10F depicts the sample preparation of FIG. 10E with added detergent (Triton X-100; TX100).

To further demonstrate the effectiveness of the methods provided herein, stained platelet-free plasma was analyzed, which produced a distinct population of events in which the scatter intensity increased with increasing fluorescence and estimated diameter (FIG. 10E). The scatter intensity of this population was higher that the light scatter from the stained vesicles/liposomes demonstrated in FIG. 10O, likely owing to the higher refractive index of cell-derived vesicles in plasma that contain proteins, nucleic acids, and other cellular components compared to synthetic liposomes/vesicles, which are composed only of lipids and buffer. Addition of detergent eliminates the population of events derived from the vesicles in platelet-free plasma (FIG. 10F), confirming that it is vesicular in nature. Thus, vesicle flow cytometry using fluorescence detection addresses many of the difficult issues associated with light scatter-based detection, and renders light scatter measurements more useful for the study of membrane vesicles in complex biological fluids such as plasma.

Example 12: Multimarker Analysis of EVs in Human Plasma

Vesicles in complex biological fluids such as plasma are heterogeneous, originating from different cell types and from different compartments within cells. To demonstrate that the methods provided herein effectively resolve heterogeneity in these vesicles by measuring multiple fluorophores simultaneously on individual particles, we prepared human platelet rich plasma (PRP) by centrifuging blood at 50×g for 15 minutes and collecting the supernatant. The PRP was aged for 24 hours, and then centrifuged twice at 2500×g for 15 minutes to prepare cell free plasma (PRP supernatant), which was then frozen. Aliquots of plasma were thawed and stained with di-8-ANEPPS (500 nM) and three different fluorescence-labeled reagents: PECy7-annexin V (a marker of phosphatidyl serine), PE-anti-CD41 (a marker of CD41 on platelets), and APC-anti-CD235 (a marker of CD235 on erythrocytes). Annexin V has a specific binding affinity for phosphatidyl serine (PS), which is a surface molecular marker of many cell-derived EVs, membrane vesicles and liposomes. Synthetic liposomes (prepared as in Example 1 above) bearing phosphatidylserine were also stained using PECy7-annexin V as a positive control and PE-anti-CD41 and APC-anti-CD235 as negative controls, since they do not contain the CD41 and CD235 antigens. Intensity calibration beads for PE and APC were used to calibrate these signals in units of mean equivalent soluble fluorochromes (MESF).

Figure 11A:
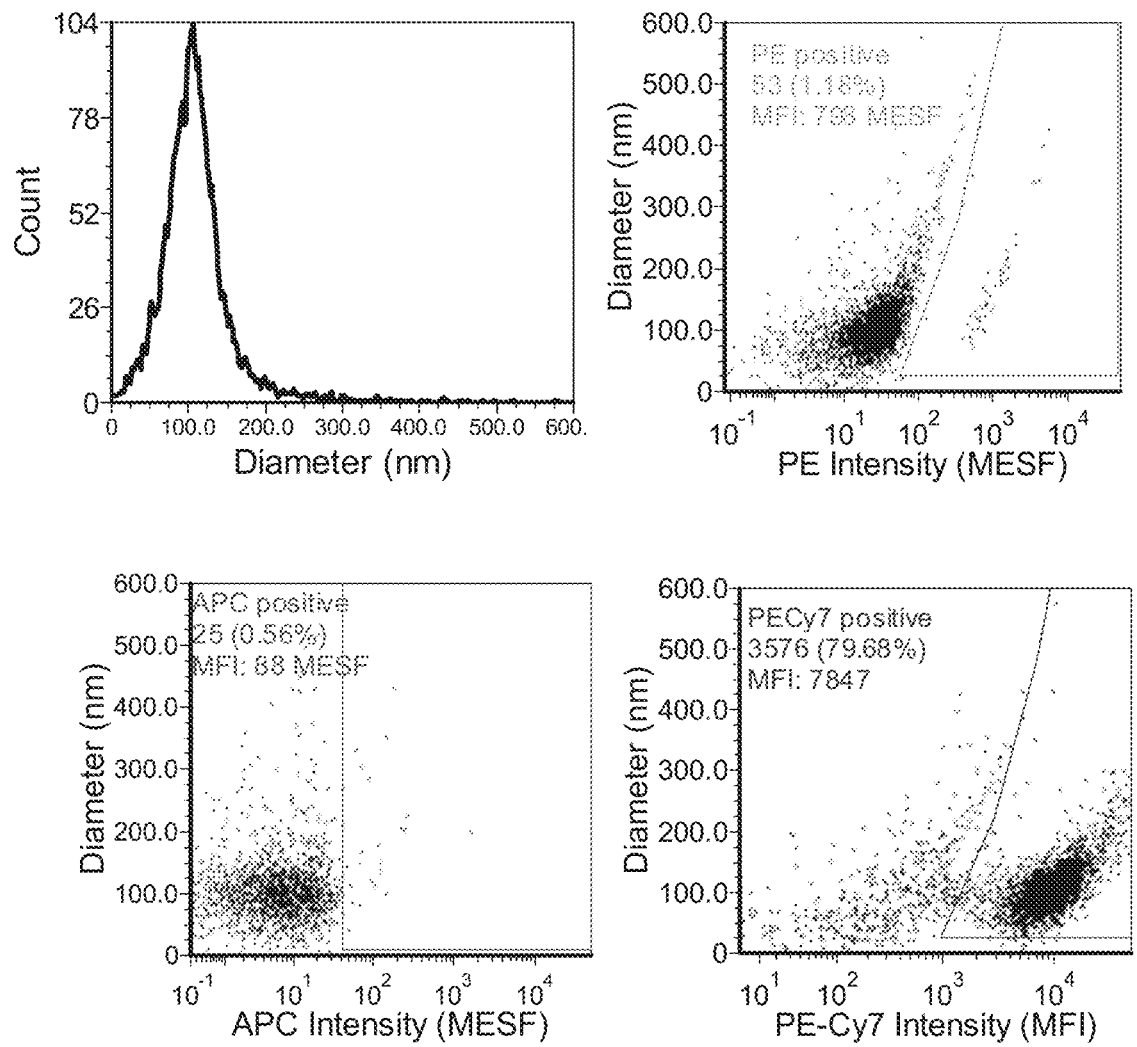
Figure 11B:
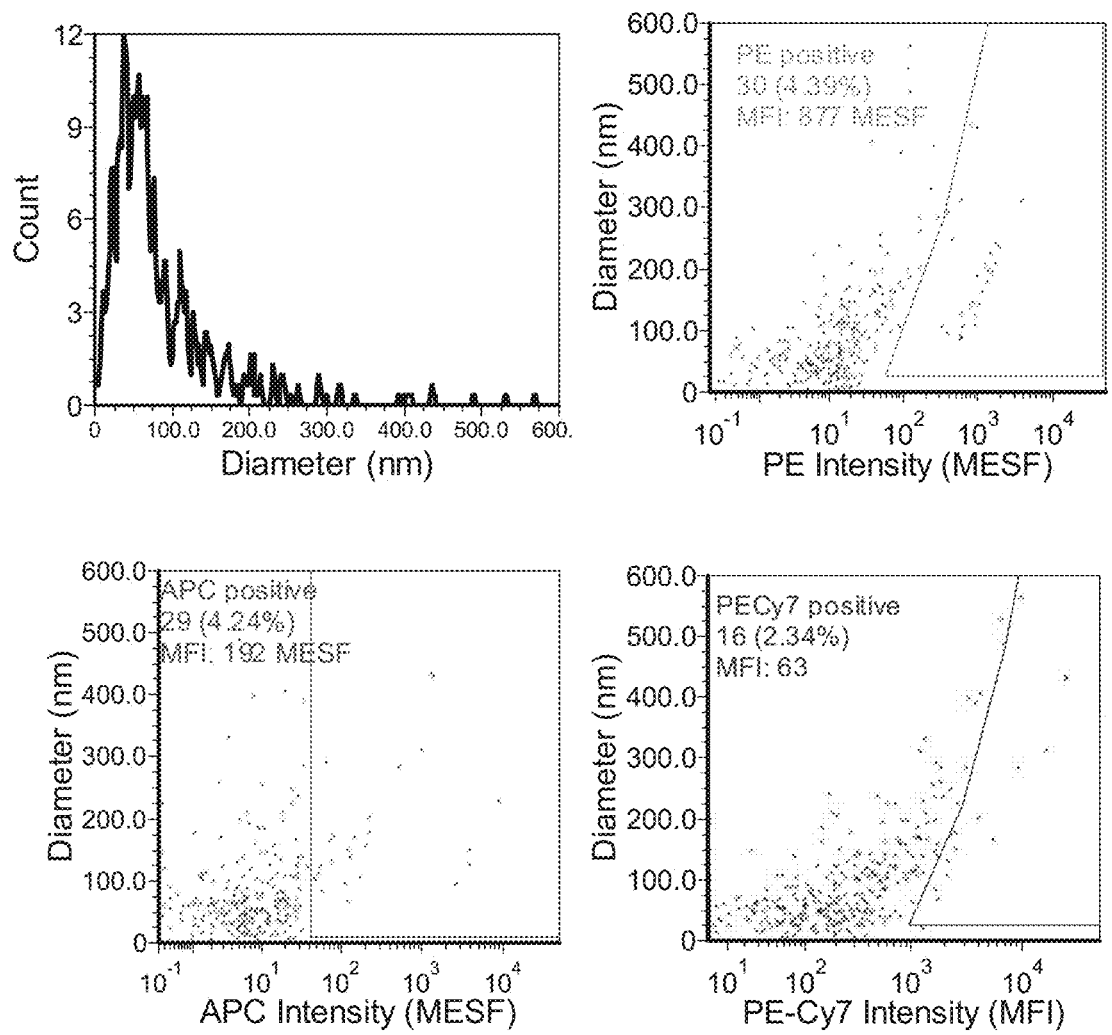
Figure 11D:
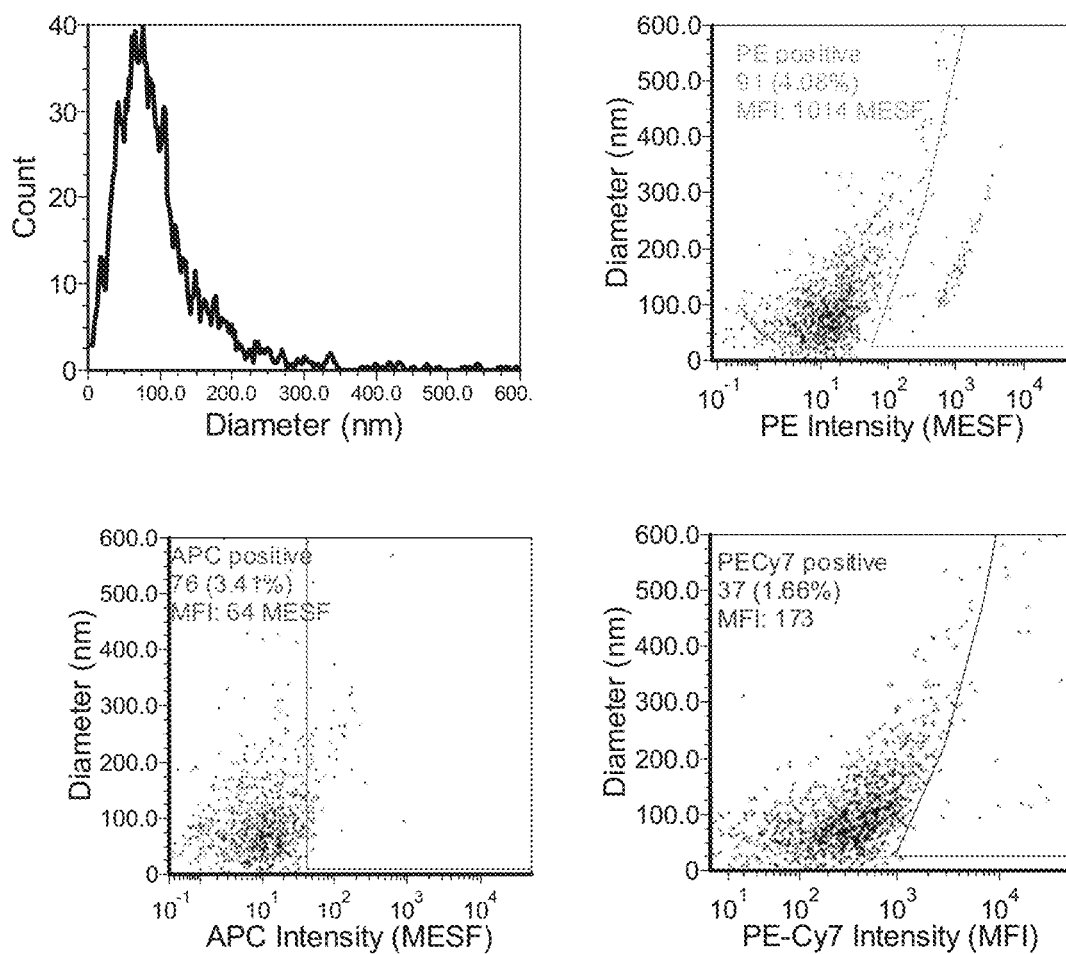

Presented in FIG. 11A is the population size distribution of the synthetic liposomes as estimated from di-8-ANEPPS staining intensity and bivariate histograms of diameter, versus fluorescence intensity of the three different fluorescence-labeled reagents. The liposomes showed strong staining for annexin V (PECy7 Intensity) and low levels of background from the PE-anti-CD41 (PE Intensity) and APC-anti-CD235 (APC Intensity), likely resulting from antibody aggregates. Treatment of the sample with the detergent Triton X-100 (0.05%) eliminates the liposomes, while the antibody aggregates and other non-membrane background events remain (FIG. 11B). Presented in FIG. 11C is the population size distribution of EVs in plasma as estimated from di-8-ANEPPS staining intensity and bivariate histograms of diameter, versus fluorescence intensity of the three different fluorescence-labeled reagents. Subsets of EVs showed staining for CD41 (PE Intensity) and annexin V (PE-Cy7 Intensity). When this sample was treated with 0.05% Triton X-100, the EVs were eliminated leaving behind the detergent-insoluble background particles FIG. 11D). Thus, this method allows the selective detection of membrane vesicles, estimation of their size, and measurement of surface molecule markers directly in plasma.

Example 13: Examples of Certain Non-Limiting Embodiments

Listed hereafter are non-limiting examples of certain embodiments of the technology.

A1. A method of analyzing particles in a sample, the method comprising:
 (a) contacting a sample comprising the particles with one or more optically detectable labels, thereby forming a staining solution, wherein:
  (i) the one or more optically detectable labels comprise a surface area probe or volume probe, wherein the surface area probe or volume probe interacts with the particles stoichiometrically with respect to particle surface area or volume, respectively, thereby forming particles comprising particle-associated surface area probe or volume probe, wherein the optical signal from the particle-associated surface area probe or volume probe is proportional to the surface area or volume, respectively, of the particle, and/or
  (ii) the one or more optically detectable labels comprise a molecular marker-specific probe, wherein the molecular marker-specific probe interacts with a molecular marker of the particle stoichiometrically with respect to the number of molecules of the molecular marker that are associated with the particle, thereby forming particles comprising particle-associated molecular marker-specific probe, wherein the optical signal from the particle-associated molecular marker-specific probe is proportional to the number of molecules of molecular marker associated with the particle; and
 (b) without physical separation or isolation of the particles, detecting the optical signal of the one or more particle-associated optically detectable labels generated in (i) and/or (ii), thereby analyzing the particles in the sample.

A2. The method of embodiment A1, wherein at least one particle in the sample comprises a size of about 500 nm or less in diameter.

A3. The method of embodiment A1 or embodiment A2, wherein at least one particle in the sample comprises a size of between about 10 nm to about 200 nm in diameter.

A4. The method of any one of embodiments A1 to A3, wherein at least one particle in the sample comprises a size of between about 50 nm to about 200 nm in diameter.

A5. The method of any one of embodiments A1 to A4, wherein at least one particle in the sample comprises a size of between about 50 nm to about 150 nm in diameter.

A6. The method of any one of embodiments A1 to A5, wherein the particles in the sample comprise a size range of between about 10 nm to about 500 nm in diameter.

A7. The method of any one of embodiments A1 to A6, wherein the particles in the sample comprise a size range of between about 50 nm to about 200 nm in diameter.

A8. The method of any one of embodiments A1 to A7, wherein the particles in the sample comprise a size range of between about 50 nm to about 150 nm in diameter.

A9. The method of any of embodiments A1 to A8, wherein prior to (a), the concentration of the particles in the sample is, or is adjusted to, between about $1\times10^6$ particles/µL to about $1\times10^{12}$ particles/µL.

A10. The method of embodiment A9, wherein the concentration of the particles in the sample is, or is adjusted to, between about $1\times10^8$ particles/µL to about $1\times10^{10}$ particles/µL.

A11. The method of embodiment A10, wherein the concentration of the particles in the sample is, or is adjusted to, about $1\times10^9$ particles/µL.

A12. The method of any of embodiments A1 to A11, wherein the staining solution comprises an isotonic buffer.

A13. The method of embodiment A11, wherein the isotonic buffer is phosphate buffered saline (PBS), Hanks balanced salt solution (HBSS) or HEPES buffered saline.

A14. The method of any of embodiments A1 to A13, wherein the staining solution comprises a surfactant.

A15. The method of any of embodiments A1 to A14, wherein the concentration of the surfactant in the staining solution is between about 0.005% to about 0.1%.

A16. The method of any of embodiments A1 to A15, wherein analyzing the particles in the sample comprises detecting the particles in the sample.

A16.1 The method of any of embodiments A1 to A16, wherein analyzing the particles in the sample comprises determining the surface area or volume of the particle based on the detected optical signal of the surface area probe or volume probe, respectively.

A16.2 The method of embodiment A16.1, further comprising determining the size of the particle based on the surface area or volume.

A16.3 The method of embodiment A16.2, wherein determining the size of the particle comprises determining the diameter of the particle.

A17. The method of any of embodiments A1 to A16.3, wherein analyzing the particles in the sample comprises determining the type and/or number of molecular markers associated with the particle based on the detected optical signal of the molecular marker-associated probe.

A17.1 The method of embodiment A17, further comprising identifying and/or quantifying the particle based on the type and/or number of molecular markers associated with the particle.

A18. The method of any of embodiments A1 to A17, wherein the surface area probe or volume probe is a fluorescent label.

A19. The method of any of embodiments A1 to A18, wherein the molecular marker-specific probe is a fluorescent label.

A20. The method of embodiment A18 or A19, wherein the fluorescent label is a fluorophore, a tandem conjugate between more than one fluorophore, a fluorescent polymer, a fluorescent protein, or a fluorophore conjugated to a molecule that interacts with the particle.

A21. The method of any of embodiments A18 to A20, wherein the fluorescent label is conjugated to a molecule that interacts with the particle.

A22. The method of embodiment A21, wherein the molecule that interacts with the particle is a protein, an antibody, a lectin, a peptide, a nucleic acid, a carbohydrate or a glycan.

A23. The method of any of embodiments A1 to A22, wherein at least one particle comprises a lipid bilayer.

A24. The method of embodiment A23, wherein the particle comprising a lipid bilayer is a liposome or an extracellular vesicle.

A25. The method of any of embodiments A18 to A24, wherein detection of the optically detectable label is by fluorescence spectroscopy, fluorescence imaging, or flow cytometry.

A26. The method of embodiment A25, wherein detection of the optically detectable label is by flow cytometry.

A27. The method of embodiment A26, wherein the particle is a liposome or an extracellular vesicle.

A28. The method of embodiment A27, wherein the surface area probe is selected from among di-8-ANEPPS, di-4-ANEPPS, a carbocyanine dye or a PKH dye.

A29. The method of embodiment A28, wherein the surface area probe is di-8-ANEPPS.

A30. The method of any of embodiments A27 to A29, wherein the ratio of the amount surface area probe (P) relative to the amount of lipid (L) in the particle, P/L, is adjusted whereby the surface area probe interacts with the particles stoichiometrically with respect to particle surface area or volume.

A31. The method of embodiment A30, wherein the P/L ratio is between about 0.1 to about 0.25.

A32. The method of any of embodiments A27 to A30, wherein the molecular marker-specific probe is a fluorophore conjugated to a protein A32.1 The method of embodiment A32, wherein the protein is selected from among annexin V, cholera toxin B-subunit, anti-CD61, anti-CD171, anti-CD325, anti-CD130, anti-G LAST, anti-EGFRvIII, anti-EGFR, anti-CD133, anti-CD15, anti-CD63, anti-CD9, anti-CD41, anti-CD235, anti-CD54 and anti-CD45.

A33. The method of embodiment A28, A32 or A32.1, wherein the fluorophore conjugated to the protein conjugates is selected from among Dylight488, a Brilliant Violet dye, Pacific Blue, Chrome Orange, Brilliant Blue 515, PE, rhodamine, FITC, PE-Cy5.5, PE-Cy7, APC, Alexa647, APC-Alexa700 and APC-Alexa750.

A34. The method of any of embodiments A1 to A33, wherein physical separation or isolation of the particles comprises washing of the particles.

A35. The method of any of embodiments A1 to A34, wherein physical separation or isolation of the particles comprises centrifugation or ultracentrifugation of the particles.

A36. The method of any of embodiments A26 to A35, wherein the flow cytometer has a configuration whereby light is collected from both sides of the flow cell.

A37. The method of any of embodiments A26 to A36, wherein the detection range of the flow cytometer is between about 500 fluorescent molecules per particle to about 5000 fluorescent molecules per particle.

A38. The method of any of embodiments A26 to A37, wherein the fluorescence resolution (R) of the flow cytometer is about or less than 200 molecules fluorescein isothiocyanate (FITC).

A39. The method of embodiment A38, wherein R is between about 1, 2, 3, 4, 5, 6, 7, 8, 9, 10, 11, 12, 13, 14, 15, 16, 17, 18, 19 or 20 molecules of FITC to about 50, 100 or 150 molecules of FITC.

A40. The method of any of embodiments A1 to A39, wherein:
the particle is an extracellular vesicle; and
based on the detected optical signal of the molecular marker-specific probe, the type of molecular marker associated with the extracellular vesicle is determined.

A40.1 The method of embodiment A40, further comprising identifying the cell and/or tissue of origin of the extracellular vesicle based on the type of molecular marker associated with the extracellular vesicle.

A41. The method of any of embodiments A1 to A40, wherein the sample comprises a plurality of particles and the method is for determining the size distribution of the plurality of particles.

A42. The method of embodiment A41, wherein the particles are extracellular vesicles.

A43. The method of any of embodiments A1 to A42, wherein the interaction of the surface area or volume probe and/or the molecular marker-specific probe with the particle is saturable, whereby the optical signal from the surface area probe or volume probe is proportional to the surface area or volume, respectively, of the particle and/or the optical signal from the molecular marker-specific probe is proportional to the number of molecules of molecular marker associated with the particle.

B1. A method of detecting, identifying, quantifying and/or determining the size of at least a first nanoparticle species in a sample comprising at two distinct nanoparticle species, the method comprising:
(a) contacting a sample comprising at least two distinct nanoparticle species, wherein the distinct nanoparticle species differ from one another by size and/or by least one molecular marker associated with each nanoparticle species, with one or more optically detectable labels comprising a surface area probe or volume probe, wherein the surface area probe or volume probe interacts with at least a first nanoparticle species stoichiometrically with respect to nanoparticle surface area or volume, respectively, thereby forming particles comprising particle-associated surface area probe or volume probe, wherein the optical signal from the particle-associated surface area probe or volume probe is proportional to the surface area or volume, respectively, of the first nanoparticle species; and/or
(b) contacting the sample with one or more optically detectable labels comprising a molecular marker-specific probe, wherein the molecular marker-specific probe interacts with a molecular marker of at least the first nanoparticle species stoichiometrically with respect to the number of molecules of the molecular marker that are associated with the nanoparticle, thereby forming particles comprising particle-associated molecular marker-specific probe, wherein the optical signal from the particle-associated molecular marker-specific probe is proportional to the number of molecules of the molecular marker that are associated with the first nanoparticle species;
(c) detecting an optical signal from the particle-associated surface area probe or volume probe and/or detecting an optical signal from the particle-associated molecular marker-specific probe, thereby obtaining an optical signal intensity from the particle-associated surface area or volume probe and/or the particle-associated molecular marker-specific probe;
(d) based on the optical intensity of the particle-associated surface area or volume probe obtained in (c), determining the surface area or volume, respectively, of at least the first nanoparticle species, thereby detecting and/or determining the size of at least the first nanoparticle species in the sample; and/or
(e) based on the optical intensity of the particle-associated molecular marker-specific probe obtained in (c), determining the type and/or number of molecular markers associated with at least the first nanoparticle species, thereby detecting, identifying and/or quantifying at least the first nanoparticle species in the sample.

B2. The method of embodiment B1, wherein between at least about 2 nanoparticle species to about 5, 6, 7, 8, 9, 10, 15, 20, 25, 30, 35, 40, 45, 50, 55, 60, 65, 70, 75, 85, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1500, 2000, 2500, 3000, 3500, 4000, 4500, 5000, 5500, 6000, 6500, 7000, 7500, 8000, 8500, 9000, 9500, or 10,000 or more different nanoparticle species are detected, identified, quantified and/or their sizes determined.

B3. The method of embodiment B1 or B2, wherein between about 1 to about 25 different optically detectable labels are contacted with the sample in (a) and/or between about 1 to about 5, 6, 7, 8, 9, 10, 15, 20, 25, 30, 35, 40, 45, 50, 55, 60, 65, 70, 75, 85, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 or 1000 or more different optically detectable labels are contacted with the sample in (b).

B4. The method of embodiment B3, wherein between about 2 to about 12 different optically detectable labels are contacted with the sample in (a) and/or between about 2 to about 12 different optically detectable labels are contacted with the sample in (b).

B5. The method of any of embodiments B1 to B4, wherein detection of the optically detectable label is by fluorescence spectroscopy, fluorescence imaging, or flow cytometry.

B6. The method of embodiment B5, wherein detection of the optically detectable label is by flow cytometry.

B7. The method of any of embodiments B1 to B6, wherein the nanoparticle is a liposome or an extracellular vesicle.

B8. The method of embodiment B6 or B7, wherein the surface area probe is selected from among di-8-ANEPPS, di-4-ANEPPS, a carbocyanine dye, a PKH dye or F2N12S.

B9. The method of embodiment B8, wherein the surface area probe is di-8-ANEPPS.

B10. The method of any of embodiments B7 to B9, wherein the ratio of the amount surface area probe (P) relative to the amount of lipid (L) in the particle, P/L, is adjusted whereby the surface area probe or volume probe interacts with the particles stoichiometrically with respect to particle surface area or volume, respectively.

B11. The method of embodiment B10, wherein the P/L ratio is between about 0.1 to about 0.25.

B12. The method of any of embodiments B6 to B11, wherein the molecular marker-specific probe is a fluorophore conjugated to a protein.

B12.1 The method of embodiment B12, wherein the protein is selected from among annexin V, cholera toxin B-subunit, anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54 and anti-CD45.

B13. The method of embodiment B8, B12 or B12.1, wherein the fluorophore conjugated to the protein conjugates is selected from among Dylight488, a Brilliant Violet dye, Pacific Blue, Chrome Orange, Brilliant Blue 515, PE, rhodamine, FITC, PE-Cy5.5, PE-Cy7, APC, Alexa647, APC-Alexa700 and APC-Alexa750.

B14. The method of any of embodiments B1 to B13, further comprising, before (c):
  (i) contacting the sample with an optical standard particle corresponding to at least the first nanoparticle species, wherein the optical standard particle comprises an optically detectable label that is the surface area or volume probe that interacts with the first nanoparticle species in (a) or the optical standard particle comprises an optically detectable label that is the molecular marker-specific probe that interacts with the first nanoparticle species in (b);
  (ii) detecting an optical signal from the optically detectable label associated with the optical standard particle in (c), thereby obtaining an optical signal intensity; and
  (iii) based on the optical signal intensity obtained in (ii), adjusting the optical signal intensity of the corresponding detected optical signal from the particle-associated surface area or volume probe of the first nanoparticle species and/or the molecular marker-specific probe of the first nanoparticle species; and
  (iv) based on the adjusted optical signal intensity obtained in (iii), detecting and/or determining the size, type or identity of the first nanoparticle species in the sample.

B15. The method of any of embodiments B1 to B14, further comprising, before (c):
  (i) contacting the sample with a optical standard particle, wherein the optical standard particle does not comprise an optically detectable label;
  (ii) detecting an optical signal from the optical standard particle, thereby obtaining an optical signal intensity; and
  (iii) based on the optical signal intensity obtained in (ii), adjusting the optical signal intensity of the particle-associated surface area probe or volume probe of the first nanoparticle species and/or the molecular marker-specific probe of the first nanoparticle species; and
  (iv) based on the adjusted optical signal intensity obtained in (iii), detecting and/or determining the size, type or identity of the first nanoparticle species in the sample.

B16. The method of embodiment B14, wherein the optical standard particle comprising the optically detectable label further comprises an antibody, a liposome or a silica particle.

B17. The methods of any of embodiments B14 to B16, wherein the size of the optical standard particle is between about 50 nm to about 500 nm.

B18. The method of embodiment B16 or B17, wherein the optical standard particle comprising the optically detectable label further comprises an antibody.

B18.1 The method of embodiment B18, wherein the antibody is selected from among anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54, anti-CD45 and anti-IgG.

B19. The method of embodiment B18, wherein the antibody is conjugated to an optically detectable label that is a fluorophore.

B20. The method of embodiment B19, wherein the fluorophore is selected from among DyLight488, a Brilliant Violet dye, Pacific Blue, Chrome Orange, Brilliant Blue 515, PE, FITC, PE-Cy5.5, PE-Cy7, APC, Alexa647, APC-Alexa700 and APC-Alexa750.

B21. The method of embodiment B15, wherein the optical standard particle comprises BSA.

B22. The method of any of embodiments B1 to B21, wherein the nanoparticles comprise nanovesicles.

B23. The method of any of embodiments B1 to B22, wherein the nanovesicles are extracellular vesicles.

B24. The method of embodiment B23, wherein identifying the type or identity of the first nanoparticle species comprises determining the cellular origin of the extracellular vesicle.

B25. The method of embodiment B24, wherein the cellular origin of the extracellular vesicle is a cancer cell.

B26. The method of embodiment B25, wherein the cancer cell is a glioblastoma cell.

B27. The method of any of embodiments B1 to B26, wherein the size of the nanoparticle species is between about 25 nm to about 900 nm.

B28. The method of embodiment B27, wherein the size of the nanoparticle species is between about 100 nm to about 500 nm.

B29. The method of any of embodiments B14 to B17 and B22 to B28, wherein the optical standard particle comprising the optically detectable label comprises a silica particle in association with a lipid bilayer.

B30. The method of any of embodiments B14 to B17 and B22 to B28, wherein the optical standard particle comprising the optically detectable label comprises a liposome.

B31. The method of embodiment B29 or B30, wherein the size of the optical standard particle is between about 50 nm to about 500 nm.

B32. The method of embodiment B31, wherein the size of the optical standard particle is between about 100 nm to about 200 nm.

B33. The method of any of embodiments B29 to B32, wherein the optical standard particle comprises an optically detectable label that is a surface area probe.

B34. The method of embodiment B33, wherein the surface area probe is a fluorophore selected from among di-8-ANEPPS, di-4-ANEPPS, a carbocyanine dye and a PKH dye.

B35. The method of embodiment B34, wherein the surface area probe is di-8-ANEPPS.

B36. The method of any of embodiments B6 to B35, wherein the flow cytometer has a configuration whereby light is collected from both sides of the flow cell.

B37. The method of any of embodiments B6 to B36, wherein the detection range of the flow cytometer is between about 500 fluorescent molecules per particle to about 5000 fluorescent molecules per particle.

B38. The method of any of embodiments B6 to B37, wherein the fluorescence resolution (R) of the flow cytometer is about or less than 200 molecules fluorescein isothiocyanate (FITC).

B39. The method of embodiment B38, wherein R is between about 20 molecules FITC to about 150 molecules FITC.

B40. The method of any of embodiments B1 to B39, wherein the interaction of the surface area or volume probe and/or the molecular marker-specific probe with the particle is saturable, whereby the optical signal from the surface area probe or volume probe is proportional to the surface area or volume, respectively, of the particle and/or the optical signal from the molecular marker-specific probe is proportional to the number of molecules of molecular marker associated with the particle.

C1. A method of determining the size of a nanoparticle of interest in a sample using an optically detectable label, the method comprising:

(a) contacting a nanoparticle of interest with an optically detectable label comprising a surface area probe or volume probe, wherein the optically detectable label interacts with the nanoparticle of interest, whereby a nanoparticle of interest comprising nanoparticle of interest-associated optically detectable label is obtained;

(b) detecting the nanoparticle of interest-associated optically detectable label of (a), thereby obtaining an optical signal intensity;

(c) obtaining a predetermined correlation between optical signal intensity and size of each nanoparticle of a preparation of nanoparticles comprising a distribution of sizes, wherein:

(i) the preparation of nanoparticles is contacted with the optically detectable label used in (a);

(ii) the optically detectable label interacts stoichiometrically with each of the nanoparticles of the preparation, whereby nanoparticles comprising nanoparticle-associated optically detectable label are obtained, wherein the optical signal from each nanoparticle-associated optically detectable label is proportional to the surface area or volume of its corresponding associated nanoparticle;

(iii) the optical signals of the nanoparticle-associated optically detectable labels of (ii) are detected, thereby obtaining optical signal intensities corresponding to the nanoparticle-associated optically detectable labels associated with each nanoparticle of the preparation; and (iv) the optical signal intensity of each nanoparticle-associated optically detectable label obtained in (iii) is correlated with the size of its corresponding associated nanoparticle; and (d) based on the predetermined correlation obtained according to (c), and based on the optical signal intensity obtained in (b), determining the size of the nanoparticle of interest.

C2. The method of embodiment C1, wherein obtaining a correlation in (c) comprises:

(1) obtaining a preparation of nanoparticles comprising a distribution of sizes, wherein the preparation does not comprise the nanoparticle of interest;

(2) determining the size distribution of the preparation of nanoparticles without contacting the preparation with an optically detectable label;

(3) contacting the preparation with an optically detectable label, wherein the optically detectable label comprises the surface area probe or volume probe in (a), wherein the surface area probe or volume probe interacts with the nanoparticles stoichiometrically with respect to nanoparticle surface area or volume, respectively, whereby the optical signal from the optically detectable label is proportional to the surface area or volume, respectively, of each nanoparticle in the preparation;

(4) detecting the optical signals obtained by (3), thereby obtaining the optical signal intensities of each nanoparticle in the preparation; and (5) correlating the optical signal intensities obtained in (4) with the size distribution determined in (2).

C3. The method of embodiment C1 or C2, wherein the nanoparticle of interest is an extracellular vesicle.

C4. The method of any of embodiments C1 to C3, wherein the preparation of nanoparticles comprises liposomes.

C5. The method of any of embodiments C1 to C3, wherein the preparation of nanoparticles comprises silica particles, wherein each silica particle comprises a lipid bilayer.

C6. The method of any of embodiments C1 to C5, further comprising adding the preparation of nanoparticles, whose predetermined correlation has been obtained according to (c), to (a), wherein:

(1) the optically detectable label interacts with the nanoparticle of interest and with the preparation of nanoparticles, whereby a nanoparticle of interest comprising nanoparticle of interest-associated optically detectable label and nanoparticles comprising nanoparticle-associated optically detectable label are obtained;

(2) optical signal intensities are obtained from the nanoparticle of interest-associated optically detectable label and the nanoparticle-associated optically detectable label in (b); and (3) the size of the nanoparticle of interest is determined in (d) based on the predetermined correlation obtained according to (c) and based on the optical signal intensities obtained from the nanoparticle of interest-associated optically detectable label and the nanoparticle-associated optically detectable label in (b).

C7. The method of any of embodiments C1 to C5, further comprising:

(1) in the absence of the nanoparticle of interest, contacting the preparation of nanoparticles, whose predetermined correlation has been obtained according to (c), with the optically detectable label used in (a), thereby forming a mixture comprising the preparation of nanoparticles and the optically detectable label, wherein the optically detectable label interacts stoichiometrically with each of the nanoparticles of the preparation, whereby nanoparticles comprising nanoparticle-associated optically detectable label are obtained, wherein the optical signal from each nanoparticle-associated optically detectable label is proportional to the surface area or volume of its corresponding associated nanoparticle;

(2) adding the mixture of (1) to (b), thereby detecting the nanoparticle of interest-associated optically detectable label and the nanoparticle-associated optically detectable label and obtaining optical signal intensities of the nanoparticle of interest-associated optically detectable label and the nanoparticle-associated optically detectable label; and (3) based on the predetermined correlation obtained according to (c) and based on the optical signal intensities obtained from the nanoparticle of interest-associated optically detectable label and the nanoparticle-associated optically detectable label in (b), determining the size of the nanoparticle of interest in (d).

C8. The method of any of embodiments C1 to C7, wherein the interaction of the surface area probe or volume probe with the nanoparticle of interest is saturable, whereby the optical signal from the surface area probe or volume probe is proportional to the surface area or volume of the particle.

D1. A method of identifying and/or quantifying a nanoparticle of interest in a sample using an optically detectable label, the method comprising:

(a) contacting a nanoparticle of interest with an optically detectable label comprising a molecular marker-specific probe, wherein the optically detectable label interacts with a molecular marker associated with the nanoparticle of interest, whereby a nanoparticle of interest comprising nanoparticle of interest-associated optically detectable label is obtained;

(b) detecting the nanoparticle of interest-associated optically detectable label of (a), thereby obtaining an optical signal intensity;

(c) obtaining a predetermined correlation between optical signal intensity and the number of molecular markers associated with each nanoparticle of a preparation of nanoparticles, wherein:
  (i) the preparation of nanoparticles is contacted with the optically detectable label used in (a);
  (ii) the optically detectable label interacts stoichiometrically with each of the nanoparticles of the preparation, whereby nanoparticles comprising nanoparticle-associated optically detectable label are obtained, wherein the optical signal from each nanoparticle-associated optically detectable label is proportional to number of molecules of the molecular marker on the corresponding associated nanoparticle;
  (iii) the optical signals of the nanoparticle-associated optically detectable labels of (ii) are detected, thereby obtaining optical signal intensities corresponding to the nanoparticle-associated optically detectable labels associated with each nanoparticle of the preparation; and
  (iv) the optical signal intensity of each nanoparticle-associated optically detectable label obtained in (iii) is correlated with the identity and/or quantity of its corresponding associated nanoparticle; and
(d) based on the predetermined correlation obtained in (c), and based on the optical signal intensity obtained in (b), identifying and/or quantifying the nanoparticle of interest.

D2. The method of embodiment C1, wherein obtaining a correlation in (c) comprises:
  (1) obtaining a preparation of nanoparticles comprising a distribution of different numbers of molecules of a molecular marker associated with each of the nanoparticles, wherein the molecular marker is the marker associated with the nanoparticle of interest in (a) and the preparation does not comprise the nanoparticle of interest;
  (2) determining the numbers of the molecular markers in each nanoparticle of the preparation, without contacting the preparation with an optically detectable label;
  (3) contacting the preparation with an optically detectable label, wherein the optically detectable label comprises the molecular marker-specific probe in (a), wherein the molecular marker-specific probe interacts with the nanoparticles stoichiometrically with respect to the number of molecules of molecular marker associated with each nanoparticle of them preparation, whereby the optical signal from the optically detectable label is proportional to the number of molecules of molecular marker associated with each nanoparticle of the preparation;
  (4) detecting the optical signals obtained by (3), thereby obtaining the optical signal intensities of each nanoparticle in the preparation; and
  (5) correlating the optical signal intensities obtained in (4) with the numbers of the molecular markers determined in (2).

D3. The method of embodiment D1 or D2, wherein the nanoparticle of interest is an extracellular vesicle.

D4. The method of any of embodiments D1 to D3, wherein the preparation of nanoparticles comprises liposomes.

D5. The method of any of embodiments D1 to D3, wherein the preparation of nanoparticles comprises beads comprising at least one antibody, wherein the antibody is conjugated to an optically detectable label.

D6. The method of any of embodiments D1 to D5, further comprising adding the preparation of nanoparticles, whose predetermined correlation has been obtained according to (c), to (a), wherein:
  (1) the optically detectable label interacts with the nanoparticle of interest and with the preparation of nanoparticles, whereby a nanoparticle of interest comprising nanoparticle of interest-associated optically detectable label and nanoparticles comprising nanoparticle-associated optically detectable label are obtained;
  (2) optical signal intensities are obtained from the nanoparticle of interest-associated optically detectable label and the nanoparticle-associated optically detectable label in (b); and
  (3) the nanoparticle of interest is identified and/or quantified in (d) based on the predetermined correlation obtained according to (c) and based on the optical signal intensities obtained from the nanoparticle of interest-associated optically detectable label and the nanoparticle-associated optically detectable label in (b).

D7. The method of any of embodiments D1 to d5, further comprising:
  (1) in the absence of the nanoparticle of interest, contacting the preparation of nanoparticles, whose predetermined correlation has been obtained according to (c), with the optically detectable label used in (a), thereby forming a mixture comprising the preparation of nanoparticles and the optically detectable label, wherein the optically detectable label interacts stoichiometrically with each of the nanoparticles of the preparation, whereby nanoparticles comprising nanoparticle-associated optically detectable label are obtained, wherein the optical signal from each nanoparticle-associated optically detectable label is proportional to the surface area or volume of its corresponding associated nanoparticle;
  (2) adding the mixture of (1) to (b), thereby detecting the nanoparticle of interest-associated optically detectable label and the nanoparticle-associated optically detectable label and obtaining optical signal intensities of the nanoparticle of interest-associated optically detectable label and the nanoparticle-associated optically detectable label; and
  (3) based on the predetermined correlation obtained according to (c) and based on the optical signal intensities obtained from the nanoparticle of interest-associated optically detectable label and the nanoparticle-associated optically detectable label in (b), identifying and/or quantifying the nanoparticle of interest in (d).

D8. The method of any of embodiments D1 to D7, wherein the interaction of the surface area or volume probe and/or the molecular marker-specific probe with the particle is saturable, whereby the optical signal from the surface area probe or volume probe is proportional to the surface area or volume, respectively, of the particle and/or the optical signal from the molecular marker-specific probe is proportional to the number of molecules of molecular marker associated with the particle.

E1. A preparation of optical standard particles, comprising a silica particle and a lipid bilayer in association with the silica particle, wherein the preparation has a distribution of optical standard particle sizes between about 10 nm to about 900 nm.

E2. The preparation of embodiment E1, wherein the lipid bilayer comprises an outer coating on the silica particle.

E3. The preparation of embodiment E1 or E2, wherein the distribution of optical standard particle sizes is between about 50 nm to about 500 nm.

E4. The preparation of embodiment E3, wherein the distribution of optical standard particle sizes is between about 20 nm to about 200 nm.

E5. A optical standard particle, comprising a silica particle and a lipid bilayer in association with the silica particle.

E6. The optical standard particle of embodiment E5, wherein the lipid bilayer comprises an outer coating on the silica particle.

E7. The optical standard particle of embodiment E5 or E6, wherein the size of the optical standard particle is about 50 nm to about 200 nm.

E8. The optical standard particle of embodiment E7, wherein the size of the optical standard particle is about 100 nm to about 150 nm.

F1. The method of any of embodiments A1 to A43, B1 to B40, C1 to C8 or D1 to D8, wherein the optically detectable label associated with the particle is detected in the presence of free label.

F2. The method of any of embodiments A1 to A43, B1 to B40, C1 to C8, D1 to D8 or F1, wherein the sample is a biological sample.

F3. The method of embodiment F2, wherein the biological sample comprises particles and a biological fluid.

F4. The method of embodiment F3, wherein the biological fluid comprises blood, plasma, serum, urine, saliva, seminal fluid, lavages, cervical fluid, cervicovaginal fluid, cerebrospinal fluid, vaginal fluid, breast fluid, breast milk, synovial fluid, semen, seminal fluid, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum or combinations, fractions or components thereof.

F5. The method of embodiment F4, wherein the biological fluid comprises cerebrospinal fluid.

F6. The method of any of embodiments F2 to F5, wherein the biological sample comprises particles derived from a cell or tissue.

F7. The method of embodiment F6, wherein the cell or tissue is a cancer cell or tissue.

F8. The method of embodiment F6 or F7, wherein the cell or tissue is selected from among liver, lung, spleen, pancreas, colon, skin, bladder, eye, brain, esophagus, head, neck, ovary, testes, prostate, placenta, epithelium, endothelium, adipocyte, kidney, heart, muscle, blood and combinations thereof.

F9. The method of embodiment F7 or F8, wherein the sample comprises a biological fluid.

F10. The method of embodiment F9, wherein the biological fluid is blood, plasma, serum, saliva, urine or cerebrospinal fluid.

F11. The method of embodiment F10, wherein the biological fluid is saliva, urine or serum.

F12. The method of embodiment F11, wherein the biological sample comprises particles derived from a cancer cell or tissue and the cancer is ovarian, lung, bladder or prostate cancer.

F13. The method of embodiment F10, wherein the biological fluid is cerebrospinal fluid.

F14. The method of embodiment F13, wherein the biological sample comprises particles derived from a cancer cell or tissue and the cancer is brain cancer.

F15. The method of embodiment F14, wherein the brain cancer is glioblastoma.

F16. the method of any of embodiments F2 to F15, wherein the particle is selected from among membrane vesicles, liposomes, lipoproteins, apoptotic bodies, viruses, viral particles, virus-like particles, extracellular vesicles or combinations thereof.

F17. The method of embodiment F16, wherein the particle is an extracellular vesicle.

F18. The method of embodiment F17, wherein the sample comprises more than one type of extracellular vesicle, wherein each vesicle originates from a cell or tissue that is different from the cell or tissue of origin of at least one other type of extracellular vesicle in the sample.

G1. The method of any of embodiments A1 to A43, B1 to B40, C1 to C8, D1 to D8 or F1 to F18, wherein large particulates other than the particles, cells, cellular debris or a combination thereof are removed from the sample.

G2. The method of embodiment G1, wherein the large particulates other than the particles, cells, cellular debris or a combination thereof are removed by centrifugation.

X1. The method of any of embodiments A1 to A43, B1 to B40, C1 to C8, D1 to D8, F1 to F18, G1 or G2, wherein the amount or concentration of the optically detectable label approaches or is at saturation.

X2. The method of embodiment X1, wherein approaching saturation or being at saturation is determined by the method of any of embodiments H0 to H54.

H0. A method of determining whether staining of a lipid-containing particle with an optically detectable label selected from among a surface area probe, a volume probe or a molecular marker-specific probe of a particle is approaching saturation or is saturated, the method comprising:
(a) contacting a first amount of a sample comprising one or more of the lipid-containing particles with a first concentration of the probe, thereby forming a first staining solution comprising the probe associated with the particles;
(b) determining the wavelength at which the maximum optical signal intensity of the particle-associated probe is detected, thereby obtaining a first maximum optical signal wavelength;
(c) obtaining a predetermined second maximum optical wavelength corresponding to a second staining solution comprising a second amount of the sample and/or a second concentration of the probe, or performing (a) and (b) using a second amount of the sample and/or a second concentration of the probe, wherein the ratio of the second concentration of the probe relative to the second amount of the sample is less than the ratio of the first concentration of the probe relative to the first amount of the sample; and
(d) analyzing the first maximum optical signal wavelength of (b) and the second maximum optical wavelength of (c), whereby if the first maximum optical signal wavelength is different from the second maximum optical signal wavelength, then the first staining solution comprises one or more lipid-containing particles comprising a ratio of probe to lipid that is approaching saturation or has saturated.

H1. The method of embodiment H0, further comprising:
(i) before (a), contacting the sample with a first amount of an optical standard particle, wherein the optical standard particle comprises a known amount of lipid;
(ii) in (a), contacting the sample comprising the optical standard particle with the first concentration of probe and determining the amount of probe relative to the amount of lipid in the optical standard particle of the first staining solution formed in (a), thereby obtaining a first probe to lipid ratio, P/L, of the optical standard particle in the first staining solution;
(iii) in (c), obtaining a predetermined second maximum optical wavelength corresponding to a second staining solution comprising a second amount of the optical standard particle and/or a second concentration of the probe corresponding to a second probe to lipid ratio, P'/L', of the optical standard particle in the second staining solution, or performing (a) and (b) using a second amount of the optical standard particle and/or a second concentration of the probe, thereby obtaining a second probe to lipid ratio, P'/L', wherein P'/L' is less than P/L;
(iv) in (d), obtaining a correlation between the probe to lipid ratios of the optical standard particle in the first and second staining solutions and the first and second maximum optical signal wavelengths wherein the first maximum optical signal wavelength corresponds to the probe to lipid ratio P/L and the second maximum optical signal wavelength corresponds to the probe to lipid ratio P'/L' whereby, if the first maximum optical signal wavelength is different from the second maximum optical signal wavelength, the probe to lipid ratio P/L is identified as a ratio that approaches saturation or is at saturation; and
(v) if the probe to lipid ratio P/L is identified as a ratio that approaches saturation or is at saturation in (iv), determining that the amount of probe added to the first staining solution approaches saturation or saturates in the lipid-containing particle in the first staining solution.

H2. The method of embodiment H0 or H1 that is performed for a plurality of amounts of sample and/or concentrations of probe, thereby obtaining a plurality of staining solutions each corresponding to a unique ratio of probe concentration to sample amount ranging from a lowest ratio to a highest ratio, or each corresponding to a unique probe to lipid ratio ranging from a lowest ratio to a highest ratio, wherein a staining solution is identified as comprising a concentration of probe that approaches or is at saturation if:
the maximum optical signal wavelength of the staining solution is different from the maximum optical signal wavelength of a second staining solution comprising a lower ratio of probe concentration to sample amount and/or a lower ratio of probe to lipid; and/or
the maximum optical signal wavelength of the staining solution is about the same as the maximum optical signal wavelength of a third staining solution comprising a higher ratio of probe concentration to sample amount and/or a higher ratio of probe to lipid.

H3. A method of determining whether staining of a lipid-containing particle with an optically detectable label selected from among a surface area probe, a volume probe or a molecular marker-specific probe of a particle is approaching saturation or is saturated, the method comprising:
(a) contacting a first amount of a sample comprising one or more of the lipid-containing particles with a first concentration of the probe, thereby forming a first staining solution comprising the probe associated with the particles, wherein the particles comprise a known amount of lipid;
(b) determining the amount of probe relative to the amount of lipid in the particles of the solution formed in (a), thereby obtaining a first probe to lipid ratio, P/L;
(c) determining the wavelength at which the maximum optical signal intensity of the probe associated with the particles in (b) is detected, thereby obtaining a first maximum optical signal wavelength corresponding to the probe to lipid ratio, P/L;
(d) obtaining a predetermined second maximum optical wavelength corresponding to a second staining solution comprising particles that comprise a second probe to lipid ratio, P'/L', or performing (a)-(c) using a second amount of the sample and/or a second concentration of the probe whereby particles comprising a second probe to lipid ratio, P'/L', is obtained, wherein P'/L' is less than P/L; and
(e) analyzing the first maximum optical signal wavelength of (c) and the second maximum optical wavelength of (d), whereby, if the maximum optical signal wavelength of (c) is different from the second maximum optical signal wavelength of (d), staining of the particle with the probe at the ratio P/L is approaching saturation or has saturated.

H4. The method of any of embodiments H0 to H3, wherein the first maximum optical signal wavelength is higher than the second maximum optical signal wavelength.

H5. The method of any of embodiments H0 to H4, wherein the difference between the first maximum optical wavelength and the second maximum optical wavelength is between about 0.5 nm to about 30, 40, 45, 50, 55, 60, 65, 70, 75, 80, 90 or 100 nm.

H6. The method of any of embodiments H0 to H4, wherein the difference between the first maximum optical wavelength and the second maximum optical wavelength is about 0.5 nm, 1 nm, 1.5 nm, 2 nm, 2.5 nm, 3 nm, 4 nm, 5 nm, 6 nm, 7 nm, 8 nm, 9 nm, 10 nm, 12 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 35 nm, 40 nm, 45 nm, 50 nm, 55 nm, 60 nm, 65 nm, 70 nm, 75 nm, 80 nm, 85 nm, 90 nm, 95 nm or 100 nm.

H7. A method of determining whether staining of a lipid-containing particle with an optically detectable label selected from among a surface area probe, a volume probe or a molecular marker-specific probe of a particle is approaching saturation or is saturated, the method comprising:
(a) contacting a first amount of a sample comprising one or more of the lipid-containing particles with a first concentration of the probe, thereby forming a staining solution comprising the probe associated with the particles;
(b) contacting a second amount of the sample comprising one or more of the lipid-containing particles with a second concentration of the probe, thereby forming a second staining solution comprising the probe associated with the particles, wherein the ratio of the second concentration of the probe relative to the second amount of the sample is less than the ratio of the first concentration of the probe relative to the first amount of the sample;
(c) determining the optical signal intensity of the first staining solution at a first optical wavelength (A1) and at a second optical wavelength (A2), thereby obtaining a ratio (C1/C2) of the optical signal intensity at the first optical wavelength relative to the optical signal intensity at the second optical wavelength;
(d) determining the optical signal intensity of the second staining solution at the first optical wavelength (A1) and at the second optical wavelength (A2), thereby obtaining a ratio (C1'/C2') of the optical signal intensity at the first optical wavelength relative to the optical signal intensity at the second optical wavelength; and (e) analyzing the ratios obtained in (c) and (d), whereby:
if C1/C2 is greater than C1'/C2', then the first staining solution comprises one or more lipid-containing particles comprising a ratio of probe to lipid that is approaching saturation or has saturated.

H8. The method of embodiment H7, further comprising:
(i) before (a), contacting the sample with a first amount of an optical standard particle, wherein the optical standard particle comprises a known amount of lipid;
(ii) before (b), contacting the sample with a second amount of the optical standard particle;
(iii) in (a), contacting the sample comprising the optical standard particle with the first concentration of probe and determining the amount of probe relative to the amount of lipid in the optical standard particle of the first staining solution formed in (a), thereby obtaining a first probe to lipid ratio, P/L, of the optical standard particle in the first staining solution;
(iv) in (b), contacting the sample comprising the optical standard particle with the second concentration of probe and determining the amount of probe relative to the amount of lipid in the optical standard particle of the second staining solution formed in (b), thereby obtaining a second probe to lipid ratio, P'/L', of the optical standard particle in the second staining solution, wherein P'/L' is less than P/L;
(v) in (e), obtaining a correlation between the probe to lipid ratios of the optical standard particle in the first and second staining solutions and the ratios of the optical signal intensities at the first optical wavelength relative to the second optical wavelength whereby, if the ratio of the optical signal intensity at the first optical wavelength relative to the optical signal intensity at the second optical wavelength for the first staining solution is greater than the ratio of the optical signal intensity at the first optical wavelength relative to the optical signal intensity at the second optical wavelength for the second staining solution, then the probe to lipid ratio P/L is identified as a ratio that approaches saturation or is at saturation; and
(vi) if the probe to lipid ratio P/L is identified as a ratio that approaches saturation or is at saturation in (v), determining that the amount of probe added to the first staining solution approaches saturation or saturates in the lipid-containing particle in the first staining solution.

H8.1. A method of determining whether staining of a lipid-containing particle with an optically detectable label selected from among a surface area probe, a volume probe or a molecular marker-specific probe of a particle is approaching saturation or is saturated, the method comprising:
(a) contacting a sample comprising one or more of the lipid-containing particles with an optical standard particle, wherein staining of the optical standard particle is predetermined to approach saturation or saturate at a known ratio, C1/C2, of optical signal intensity at a first optical wavelength (A1) relative to the optical signal intensity at a second optical wavelength (A2);
(b) contacting the sample comprising the one or lipid-containing particles and the optical standard particle with the probe, thereby forming a staining solution comprising the probe associated with the lipid-containing particles and the optical standard particle;

(c) determining the optical signal intensity of the staining solution at a first optical wavelength (A1) and at a second optical wavelength (A2), thereby obtaining a ratio (C1'/C2') of the optical signal intensity at the first optical wavelength relative to the optical signal intensity at the second optical wavelength; and
(d) analyzing the ratio obtained in (c), whereby:
if C1'/C2' is equal to or equal to about C1/C2, then the staining solution comprises one or more lipid-containing particles comprising a ratio of probe to lipid that is approaching saturation or has saturated.

H9. The method of embodiment H7 or H8 that is performed for a plurality of amounts of sample and/or concentrations of probe, thereby obtaining a plurality of staining solutions each corresponding to a unique ratio of probe concentration to sample amount ranging from a lowest ration to a highest ratio, or each corresponding to a unique probe to lipid ratio ranging from a lowest ratio to a highest ratio, wherein a staining solution is identified as comprising a concentration of probe that approaches or is at saturation if:
the ratio of optical signal intensity at the first optical wavelength relative to the optical signal intensity at the second optical wavelength of the staining solution is different from the ratio of optical signal intensity at the first optical wavelength relative to the optical signal intensity at the second optical wavelength of a second staining solution comprising a lower ratio of probe concentration to sample amount and/or a lower ratio of probe to lipid; and/or
the ratio of optical signal intensity at the first optical wavelength relative to the optical signal intensity at the second optical wavelength of the staining solution is about the same as or greater than the ratio of optical signal intensity at the first optical wavelength relative to the optical signal intensity at the second optical wavelength of a second staining solution comprising a higher ratio of probe concentration to sample amount and/or a higher ratio of probe to lipid.

H10. The method of embodiment H9, wherein the ratio of optical signal intensity at the first optical wavelength relative to the optical signal intensity at the second optical wavelength of the staining solution is greater than the ratio of optical signal intensity at the first optical wavelength relative to the optical signal intensity at the second optical wavelength of a second staining solution comprising a lower ratio of probe concentration to sample amount and/or a lower ratio of probe to lipid.

H11. The method of embodiment H9 or H10, wherein the ratio of optical signal intensity at the first optical wavelength relative to the optical signal intensity at the second optical wavelength of the staining solution is about the same as or greater than the ratio of optical signal intensity at the first optical wavelength relative to the optical signal intensity at the second optical wavelength of a second staining solution comprising a higher ratio of probe concentration to sample amount and/or a higher ratio of probe to lipid.

H12. A method of determining whether staining of a lipid-containing particle with an optically detectable label selected from among one or more of surface area probe, a volume probe or a molecular marker-specific probe of a particle is approaching saturation or is saturated, wherein the amount of lipid associated with the lipid-containing particle is known, the method comprising:
(a) contacting a sample comprising one or more of the lipid-containing particles with a first amount of the sample comprising one or more of the lipid-containing particles and a first concentration of the probe, thereby forming a first staining solution comprising the probe associated with the particles;

(b) contacting the sample comprising one or more of the lipid-containing particles with a second amount of the sample comprising one or more of the lipid-containing particles and/or a second concentration of the probe, thereby forming a second staining solution comprising the probe associated with the particles;

(c) determining the amount of probe relative to the amount of lipid in the particles in the first staining solution of (a) and in the particles in the second staining solution of (b), thereby obtaining a first probe to lipid ratio, P/L, corresponding to the first staining solution and a second probe to lipid ratio, P'/L', corresponding to the second staining solution;

(d) determining the optical signal intensity of the first staining solution at a first optical wavelength (A1) and at a second optical wavelength (A2), thereby obtaining a ratio (C1/C2) of the optical signal intensity at the first optical wavelength relative to the optical signal intensity at the second optical wavelength;

(e) determining the optical signal intensity of the second staining solution at the first optical wavelength (A1) and at the second optical wavelength (A2), thereby obtaining a ratio (C1'/C2') of the optical signal intensity at the first optical wavelength relative to the optical signal intensity at the second optical wavelength; and (f) analyzing the ratios obtained in (c)-(e), whereby:
if P/L is greater than P'/L' and C1/C2 is greater than C1'/C2', staining of the particle with the probe at the ratio P/L is approaching saturation or has saturated, and P'/L' is greater than P/L and C1'/C2' is greater than C1/C2, staining of the particle with the probe at the ratio P'/L' is approaching saturation or has saturated.

H13. The method of embodiment H12, wherein a plurality of different amounts of probe is contacted with the sample in (a), thereby obtaining a plurality of solutions each comprising a different probe to lipid ratio, and analyzing the ratios in (f) comprises:
analyzing, for each of the plurality of solutions comprising a different probe to lipid ratio, a corresponding ratio of optical signal intensity at the first optical wavelength relative to the optical signal intensity at the second optical wavelength, thereby obtaining a plurality of ratios of optical signal intensities at the first optical wavelength relative to the optical signal intensity at the second optical wavelength; and
from the plurality of ratios, determining the maximum ratio of optical signal intensity at the first optical wavelength relative to the optical signal intensity at the second optical wavelength, whereby the probe to lipid ratio corresponding to the maximum ratio of optical signal intensity at the first optical wavelength relative to the optical signal intensity at the second optical wavelength is the probe to lipid ratio at which staining of the particle is approaching saturation or has saturated.

H14. The method of any of embodiments H7 to H13, wherein the first optical wavelength is greater than the second optical wavelength.

H15. The method of any of embodiments H0 to H6, wherein the first maximum optical wavelength and/or the second maximum optical wavelength are in the range of between 350 to 950 nm, between 400-900 nm, or between 600 to 800 nm.

H16. The method of any of embodiments H7 to H14, wherein the first optical wavelength and/or the second optical wavelength are in the range of between 350 to 950 nm, between 400 to 900 nm, or between 600 to 800 nm.

H17. The method of embodiment H15, wherein the first maximum optical wavelength and/or the second maximum optical wavelength are in the range of between 600 to 750 nm.

H18. The method of any of embodiments H7 to H14, wherein the first optical wavelength is in the range of between 680-700 nm and the second optical wavelength is in the range of between 600 to 720 nm.

H19. The method of embodiment H18, wherein the first optical wavelength is 690 nm and the second optical wavelength is 610 nm.

H20. The method of any of embodiments H0 to H19, wherein at least one lipid-containing particle in the sample comprises a size of about 1000 nm, 950 nm, 900 nm, 850 nm, 800 nm, 750 nm, 700 nm, 650 nm, 600 nm, 550 nm or 500 nm or less in diameter.

H21. The method of embodiment H20, wherein at least one particle in the sample comprises a size of between about 10 nm to about 200 nm in diameter.

H22. The method of embodiment H21, wherein at least one particle in the sample comprises a size of between about 50 nm to about 200 nm in diameter.

H23. The method of embodiment H22, wherein at least one particle in the sample comprises a size of between about 50 nm to about 150 nm in diameter.

H24. The method of any one of embodiments H0 to H19, wherein the lipid-containing particles in the sample comprise a size range of between about 10 nm to about 500 nm in diameter.

H25. The method of embodiment H24, wherein the particles in the sample comprise a size range of between about 50 nm to about 200 nm in diameter.

H26. The method of embodiment H25, wherein the particles in the sample comprise a size range of between about 50 nm to about 150 nm in diameter.

H27. The method of any of embodiments H1, H2, H4-H6, H8-H11 or H14-H26, wherein at least one optical standard particle in the sample comprises a size of about 1000 nm, 950 nm, 900 nm, 850 nm, 800 nm, 750 nm, 700 nm, 650 nm, 600 nm, 550 nm or 500 nm or less in diameter.

H28. The method of embodiment H27, wherein at least one particle in the sample comprises a size of between about 10 nm to about 200 nm in diameter.

H29. The method of embodiment H28, wherein at least one particle in the sample comprises a size of between about 50 nm to about 200 nm in diameter.

H30. The method of embodiment H29, wherein at least one particle in the sample comprises a size of between about 50 nm to about 150 nm in diameter.

H31. The method of any one of embodiments H1, H2, H4-H6, H8-H11 or H14-H26, wherein the lipid-containing particles in the sample comprise a size range of between about 10 nm to about 500 nm in diameter.

H32. The method of embodiment H31, wherein the particles in the sample comprise a size range of between about 50 nm to about 200 nm in diameter.

H33. The method of embodiment H32, wherein the particles in the sample comprise a size range of between about 50 nm to about 150 nm in diameter.

H34. The method of any of embodiments H0 to H33, wherein prior to (a), the concentration of the lipid-containing particles in the sample is, or is adjusted to, between about $1 \times 10^6$ particles/µL to about $1 \times 10^{12}$ particles/µL.

H35. The method of embodiment H34, wherein the concentration of the particles in the sample is, or is adjusted to, between about $1\times10^8$ particles/μL to about $1\times10^{10}$ particles/μL H36. The method of embodiment H35, wherein the concentration of the particles in the sample is, or is adjusted to, about $1\times10^9$ particles/μL.

H37. The method of any of embodiments H0 to H36, wherein the surface area probe or volume probe is a fluorescent label.

H38. The method of any of embodiments H0 to H37, wherein the molecular marker-specific probe is a fluorescent label.

H39. The method of embodiment H37 or embodiment H38, wherein the fluorescent label is a fluorophore, a tandem conjugate between more than one fluorophore, a fluorescent polymer, a fluorescent protein, or a fluorophore conjugated to a molecule that interacts with the particle.

H40. The method of any of embodiments H37 to H39, wherein the fluorescent label is conjugated to a molecule that interacts with the particle.

H41. The method of embodiment H40, wherein the molecule that interacts with the particle is a protein, an antibody, a lectin, a peptide, a nucleic acid, a carbohydrate or a glycan.

H42. The method of any of embodiments H0 to H41, wherein at least one lipid-containing particle comprises a lipid bilayer.

H43. The method of any of embodiments H1, H2, H4-H6, H8-H11 or H14-H42, wherein at least one optical standard particle comprises a lipid bilayer.

H44. The method of embodiment H42 or H43, wherein the particle is a liposome or an extracellular vesicle.

H44.1 The method of any of embodiments H0 to H44, wherein the optical wavelength and/or intensity is obtained by analyzing the sample in bulk.

H44.2 The method of any of embodiments H0 to H44, wherein the optical wavelength and/or intensity is obtained by analyzing individual particles of the sample.

H45. The method of any of embodiments H0 to H44.2, wherein the optical wavelength and/or intensity is determined by fluorescence spectroscopy, fluorescence imaging, or flow cytometry.

H46. The method of embodiment H45, wherein the optical wavelength and/or intensity is determined by flow cytometry.

H47. The method of embodiment H46, wherein individual particles of the sample are analyzed and the lipid-containing particle is a membrane vesicle, liposome, lipoprotein, apoptotic body, virus, viral particle, virus-like particle, extracellular vesicle or a combination thereof.

H48. The method of embodiment H46 or H47, wherein individual particles of the sample are analyzed and the optical standard particle is a membrane vesicle, liposome, lipoprotein, apoptotic body, virus, viral particle, virus-like particle, extracellular vesicle or a combination thereof.

H49. The method of embodiment H48, wherein the probe is a surface area probe selected from among di-8-ANEPPS, di-4-ANEPPS, a carbocyanine dye or a PKH dye.

H50. The method of embodiment H49, wherein the surface area probe is di-8-ANEPPS.

H51. The method of any of embodiments H38 to H48, wherein the probe is a molecular marker-specific probe comprising a fluorophore conjugated to a protein H52. The method of embodiment H51, wherein the protein is selected from among annexin V, cholera toxin B-subunit, anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54 and anti-CD45.

H53. The method of embodiment H51 or H52, wherein the fluorophore conjugated to the protein is selected from among Dylight488, a Brilliant Violet dye, Pacific Blue, Chrome Orange, Brilliant Blue 515, PE, rhodamine, FITC, PE-Cy5.5, PE-Cy7, APC, Alexa647, APC-Alexa700 and APC-Alexa750.

H54. The method of any of embodiments H0 to H53, wherein the optical wavelength and/or intensity is from fluorescence emission, fluorescence excitation, fluorescence absorbance, fluorescence anisotropy, fluorescence polarization, fluorescence lifetime, or a combination thereof.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments disclosed in this application, yet modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claims that follow:

What is claimed is:

1. A preparation comprising a plurality of optical standard particles and one or more optically detectable labels, wherein each of the plurality of optical standard particles comprises:

a silica particle, wherein the silica particle comprises a lipid bilayer and, optionally, at least one molecular marker in association with the silica particle; and the plurality of optical standard particles comprises a range of sizes between about 10 nm to about 900 nm.

2. The preparation of claim 1, wherein the one or more optically detectable labels comprise: (a) a surface area probe that interacts stoichiometrically with the surface area of the optical standard particle, (b) a molecular marker-specific probe that interacts stoichiometrically with the number of molecules of a molecular marker associated with the optical standard particle, or, (c) a combination of (a) and (b).

3. The preparation of claim 2, wherein at least one optically detectable label is a surface area probe.

4. The preparation of claim 2, wherein the only optically detectable label is a surface area probe.

5. The preparation of claim 2, wherein at least one of the optically detectable labels is associated with one or more optical standard particles of the plurality of particles.

6. The preparation of claim 5, wherein the optically detectable label associated with the one or more optical standard particles of the plurality of particles is a surface area probe.

7. The preparation of claim 2, wherein the surface area probe is selected from among di-8-ANEPPS, di-4-ANEPPS, F2N12S, FM-143, Cell Mask Orange, Cell Mask Green, Cell Mask Deep Red, a carbocyanine dye and a PKH dye.

8. The preparation of claim 7, wherein the surface area probe is di-8-ANEPPS.

9. The preparation of claim 2, wherein at least one of the plurality of optical standard particles comprises at least one molecular marker associated with the optical standard particle and at least one optically detectable label is a molecular marker-specific probe.

10. The preparation of claim 9, wherein each of the plurality of optical standard particles comprises a predetermined, unique number of molecules of a molecular marker associated with the optical standard particle, whereby the preparation comprises a distribution of distinct numbers of molecules of the molecular marker associated with each particle in the preparation.

11. The preparation of claim 9, wherein each of the plurality of optical standard particles comprises a unique molecular marker that is different than the molecular markers of the other optical standard particles of the preparation and each of the unique molecular markers is capable of binding to a corresponding unique optically detectable label that is different than the optically detectable labels corresponding to the molecular markers of the other optical standard particles of the preparation.

12. The preparation of claim 9, wherein the molecular marker-specific probe is a protein, a peptide, a lectin, a carbohydrate, a nucleic acid or a glycan.

13. The preparation of claim 12, wherein the molecular marker-specific probe is a protein.

14. The preparation of claim 13, wherein the protein is an antibody.

15. The preparation of claim 13, wherein the protein is selected from among annexin V, cholera toxin B-subunit, anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54 and anti-CD45.

16. The preparation of claim 15, wherein the optically detectable label is a fluorophore.

17. The preparation of claim 16, wherein the fluorophore is selected from among Dylight488, a Brilliant Violet dye, Pacific Blue, Chrome Orange, a Brilliant Blue dye, PE, rhodamine, FITC, PE-Cy5.5, PE-Cy7, APC, Alexa647, APC-Alexa700 and APC-Alexa750.

18. The preparation of claim 17, wherein the molecular marker-specific probe comprises the fluorophore Dylight488 and the protein is annexin V.

19. The preparation of claim 16, wherein the protein is conjugated to the fluorophore.

20. A method of determining the size of a nanoparticle of interest in a sample using an optically detectable label, the method comprising:
(a) contacting a nanoparticle of interest with an optically detectable label comprising a surface area probe, wherein the optically detectable label interacts with the nanoparticle of interest, whereby a nanoparticle of interest comprising nanoparticle of interest-associated optically detectable label is obtained;
(b) detecting the nanoparticle of interest-associated optically detectable label of (a), thereby obtaining an optical signal intensity;
(c) obtaining a predetermined correlation between optical signal intensity and the size of one or more optical standard particles of a preparation of claim 4, wherein the preparation of claim 4 comprises the optically detectable label used in (a); and
(d) based on the predetermined correlation obtained according to (c), and based on the optical signal intensity obtained in (b), determining the size of the nanoparticle of interest.

21. A method of identifying and/or quantifying a nanoparticle of interest in a sample using an optically detectable label, the method comprising:
(a) contacting a nanoparticle of interest with an optically detectable label comprising a molecular marker-specific probe, wherein the optically detectable label interacts with a molecular marker associated with the nanoparticle of interest, whereby a nanoparticle of interest comprising nanoparticle of interest-associated optically detectable label is obtained;
(b) detecting the nanoparticle of interest-associated optically detectable label of (a), thereby obtaining an optical signal intensity;
(c) obtaining a predetermined correlation between optical signal intensity and the number of molecular markers associated with the one or more optical standard particles of the preparation of claim 10, wherein the preparation of claim 10 comprises the optically detectable label used in (a); and
(d) based on the predetermined correlation obtained in (c), and based on the optical signal intensity obtained in (b), identifying and/or quantifying the nanoparticle of interest.

22. The preparation of claim 1, wherein the one or more optically detectable labels is/are selected from among chromophores, chemiluminescent moieties, bioluminescent moieties, fluorescent moieties and metals.

23. The method of claim 20, wherein the size of the nanoparticle of interest is determined by visual inspection, microscopy, spectroscopy, fluorescence spectroscopy, fluorescence imaging, imaging flow cytometry, flow cytometry or surface enhanced Raman scattering (SERS).

24. The method of claim 21, wherein the nanoparticle of interest is identified and/or quantified by visual inspection, microscopy, spectroscopy, fluorescence spectroscopy, fluorescence imaging, imaging flow cytometry, flow cytometry or surface enhanced Raman scattering (SERS).

25. The preparation of claim 1, wherein the plurality of optical standard particles comprises a range of sizes between about 50 nm to about 500 nm.

26. The preparation of claim 1, wherein the plurality of optical standard particles comprises a range of sizes between about 20 nm to about 200 nm.

* * * * *

UNITED STATES PATENT AND TRADEMARK OFFICE
CERTIFICATE OF CORRECTION

PATENT NO. : 11,486,829 B2  
APPLICATION NO. : 16/534854  
DATED : November 1, 2022  
INVENTOR(S) : Nolan et al.

Page 1 of 1

It is certified that error appears in the above-identified patent and that said Letters Patent is hereby corrected as shown below:

In the Claims

In Column 60, Line 26; Column 60, Line 27, delete the number "4" and replace with "3".

In Column 60, Line 49; Column 60, Line 50, delete the number "10" and replace with "9".

Signed and Sealed this
Twenty-sixth Day of September, 2023

Katherine Kelly Vidal
*Director of the United States Patent and Trademark Office*